(12) United States Patent
Smithgall et al.

(10) Patent No.: US 9,695,127 B2
(45) Date of Patent: Jul. 4, 2017

(54) COMPOUNDS FOR TREATING HIV AND METHODS FOR USING THE COMPOUNDS

(71) Applicant: University of Pittsburgh—Of the Commonwealth System of Higher Education, Pittsburgh, PA (US)

(72) Inventors: Thomas E. Smithgall, Wexford, PA (US); Lori Ann Emert-Sedlak, Cranberry Township, PA (US); Billy W. Day, Upper St. Clair, PA (US); Jielu Zhao, Pittsburgh, PA (US); Prema Chandrasekhar Iyer, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 46 days.

(21) Appl. No.: 14/441,475

(22) PCT Filed: Nov. 6, 2013

(86) PCT No.: PCT/US2013/068791
§ 371 (c)(1),
(2) Date: May 7, 2015

(87) PCT Pub. No.: WO2014/074628
PCT Pub. Date: May 15, 2014

(65) Prior Publication Data
US 2015/0291534 A1    Oct. 15, 2015

Related U.S. Application Data

(60) Provisional application No. 61/727,582, filed on Nov. 16, 2012, provisional application No. 61/724,234, filed on Nov. 8, 2012.

(51) Int. Cl.
| | | |
|---|---|---|
| C07D 231/46 | (2006.01) |
| C07D 405/04 | (2006.01) |
| C07D 401/12 | (2006.01) |
| A61K 39/39 | (2006.01) |
| A61K 31/5377 | (2006.01) |
| A61K 31/655 | (2006.01) |
| A61K 31/415 | (2006.01) |
| A61K 45/06 | (2006.01) |
| A61K 31/4155 | (2006.01) |
| A61K 31/4178 | (2006.01) |
| A61K 31/427 | (2006.01) |
| A61K 31/429 | (2006.01) |
| A61K 31/4439 | (2006.01) |
| C07D 231/20 | (2006.01) |
| C07D 403/04 | (2006.01) |
| C07D 401/04 | (2006.01) |
| C07D 417/04 | (2006.01) |

(52) U.S. Cl.
CPC ......... *C07D 231/46* (2013.01); *A61K 31/415* (2013.01); *A61K 31/4155* (2013.01); *A61K 31/4178* (2013.01); *A61K 31/427* (2013.01); *A61K 31/429* (2013.01); *A61K 31/4439* (2013.01); *A61K 31/5377* (2013.01); *A61K 31/655* (2013.01); *A61K 39/39* (2013.01); *A61K 45/06* (2013.01); *C07D 231/20* (2013.01); *C07D 401/04* (2013.01); *C07D 401/12* (2013.01); *C07D 403/04* (2013.01); *C07D 405/04* (2013.01); *C07D 417/04* (2013.01)

(58) Field of Classification Search
None
See application file for complete search history.

(56) References Cited

U.S. PATENT DOCUMENTS

| | | | | |
|---|---|---|---|---|
| 5,672,617 A | * | 9/1997 | Wachtler | ............... A01N 47/38 514/407 |
| 2006/0020012 A1 | | 1/2006 | Jones et al. | |

FOREIGN PATENT DOCUMENTS

| | | |
|---|---|---|
| WO | WO 02-30907 A1 | 4/2002 |
| WO | WO 02-100853 A1 | 12/2002 |

OTHER PUBLICATIONS

Betzi et al., "Protein protein interaction inhibition (2P2I) combining high throughput and virtual screening: Application to the HIV-1 Nef protein," *Proc. Natl. Acad. Sci.* 104(49):19256-19261, Dec. 4, 2007.
Chutiwitoonchai et al., "The identification of a small molecule compound that reduces HIV-1 Nef-mediated viral infectivity enhancement," *PLoS One*, 6(11): Nov. 2011.
Cichero et al., "Docking-based 3D-QSAR analyses of pyrazole derivatives as HIV-1 non-nucleoside reverse transcriptase inhibitors," *J. Mol. Model.*, 18: 1573-1582, Apr. 2012.
International Search Report and Written Opinion from International application No. PCT/US2012/068791, dated Feb. 28, 2014 (12 pages).

\* cited by examiner

*Primary Examiner* — Kamal Saeed
(74) *Attorney, Agent, or Firm* — Klarquist Sparkman, LLP

(57) ABSTRACT

Disclosed herein are embodiments of a compound capable of treating HIV. In particular disclosed embodiments, the compound is capable of inhibiting Nef, such as by acting as antagonists of HIV Nef function. Also disclosed are embodiments of a method of making the compound, embodiments of a method of using the compound, and embodiments of a method of identifying HIV Nef antagonists. The disclosed compound may be used alone or in combination with other pharmacologically active agents in order to promote reducing drug resistance and/or cumulative toxicity.

35 Claims, 25 Drawing Sheets

B9: MW 402.8
SID: 24784551
IC$_{50}$ Nef+Hck: 2.8 µM
IC$_{50}$ Hck alone: > 20 µM

C26: MW 402.8
SID: 24790189
IC$_{50}$ Nef+Hck: 5.4 µM
IC$_{50}$ Hck alone: 20 µM

C27: MW 543.6
SID: 26726147
IC$_{50}$ Nef+Hck: 2.9 µM
IC$_{50}$ Hck alone: > 20 µM

B10: MW 441.5
SID: 24835040
IC$_{50}$ Nef+Hck: 2.7 µM
IC$_{50}$ Hck alone: > 20 µM

C17: MW 383.4
SID: 4252095
IC$_{50}$ Nef+Hck: 4.8 µM
IC$_{50}$ Hck alone: > 20 µM

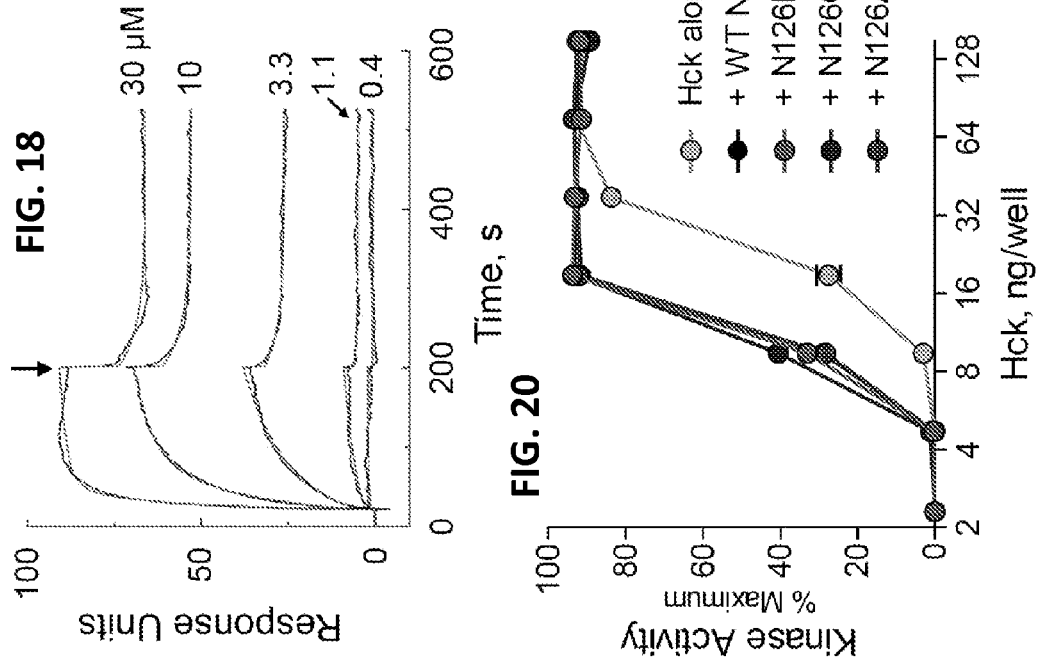
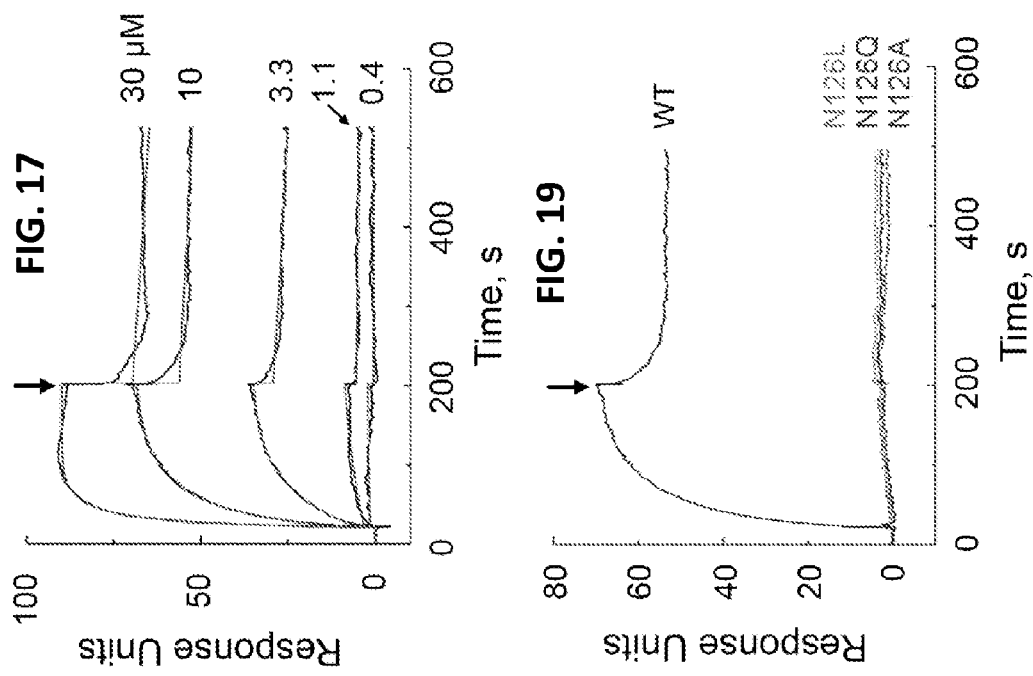
FIG. 17
FIG. 18
FIG. 19
FIG. 20

Azo linkers:

Non-azo linkers:

Untreated

WT Virus

Δ-Nef Virus 88.2%

1 µM JZ-1-97-2-1

91.1%

1 µM B9

87.5%

Untreated

CD4+=83.0%

WT virus 55.3%

Δ-Nef virus 81.9%

1 μM JZ-1-97-2-1

82.1%

1 μM B9

77.6%

COMPOUNDS FOR TREATING HIV AND METHODS FOR USING THE COMPOUNDS

CROSS REFERENCE TO RELATED APPLICATIONS

This application is the U.S. National Stage of International Application No. PCT/US2013/068791, filed Nov. 6, 2013, which was published in English under PCT Article 21(2), which in turn claims the benefit of the earlier filing dates of U.S. Provisional Applications Nos. 61/724,234, filed Nov. 8, 2012, and 61/727,582, filed Nov. 16, 2012, each of which is hereby incorporated by reference in its entirety.

ACKNOWLEDGMENT OF GOVERNMENT SUPPORT

This invention was made with government support under grant numbers AI057083; AI077444; and MH083223, awarded by the National Institutes of Health. The government has certain rights in the invention.

BACKGROUND

The year 2011 marked the 30th anniversary of the HIV/AIDS pandemic with 25 million AIDS-related deaths worldwide and 33 million people currently infected with the virus. The course of the disease changed dramatically with the advent of antiretroviral drugs, which target HIV-1 enzymes critical to the viral life cycle as well as fusion of the virus with the host cell. While cocktails of these drugs have extended the life expectancy of infected individuals, they do not clear the virus and require life-long administration. Chronic drug therapy, coupled with the remarkable mutational capacity of HIV-1, continues to drive drug resistance. The emergence of multi-drug resistant strains of HIV-1, together with uncertain prospects for an effective vaccine, underscores the urgent need for new antiretrovirals with mechanisms of action complementary to existing agents.

SUMMARY

Disclosed herein is a compound of Formula 1, or an ester or pharmaceutically acceptable salt thereof, for treating HIV

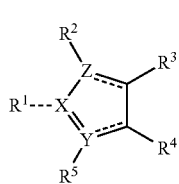

Formula 1 wherein $R^1$ is selected from hydrogen, aliphatic, aryl, heteroaliphatic, oxo, heteroaryl, or combinations thereof; $R^2$ is selected from hydrogen, aliphatic, heteroaliphatic, hydroxyl, alkoxy, thiol, thioether, amine, or combinations thereof; $R^3$ is selected from hydrogen, aliphatic, heteroaliphatic, aryl, heteroaryl, or combinations thereof; $R^4$ is selected from hydrogen, aliphatic, heteroaliphatic, aryl, heteroaryl, and combinations thereof; $R^3$ and $R^4$ can be joined together to form a 5-, 6-, 7-, or 8-membered saturated or unsaturated ring, optionally comprising one or more heteroatoms and optionally substituted with one or more substituents selected from aliphatic, heteroaliphatic, halogen, aryl, or heteroaryl; $R^5$ is selected from hydrogen, aliphatic, heteroaliphatic, aryl, heteroaryl, and combinations thereof; X is selected from nitrogen, oxygen, or carbon; Y is selected from nitrogen or carbon; Z may be selected from carbon, sulfur, and nitrogen; and provided that the compound is not (E)-4-((3-chlorophenyl)diazenyl)-5-hydroxy-3-(4-nitrophenyl)-1H-pyrazole-1-carbothioamide, 2-{(3Z)-3-[3-(1,1-dioxidotetrahydrothiophen-3-yl)-4-oxo-2-thioxo-1,3-thiazolidin-5-ylidene]-2-oxo-2,3-dihydro-1H-indol-1-yl}-N-(4-methoxyphenyl)acetamide, N-(7-methyl[1,3]thiazolo[4,5-γ][1,3]benzothiazol-2-yl)-2,3-dihydro-1,4-benzodioxine-6-carboxamide, (4Z)-4-[(4-chlorophenyl)hydrazinylidene]-3-(4-nitrophenyl)-5-oxopyrazole-1-carbothioamide, or [4-(2-hydroxybenzoyl)pyrazol-1-yl]-(3-morpholin-4-ylsulfonylphenyl)methanone.

In particular disclosed embodiments, $R^1$ is selected from hydrogen, phenyl, pyridyl, amide, ester, carboxyl, guanidino (or derivatives thereof), thioamide (or derivatives thereof), imidazoline, keto, amide, oxo, or combinations thereof. In other embodiments, $R^1$ is phenyl or pyridyl substituted with one or more substituents selected from halogen, alkoxy, cyano, nitro, hydroxyl, thiol, thioether, and combinations thereof.

In certain embodiments, $R^2$ is selected from hydrogen, hydroxyl, substituted exomethylene, or methoxy. $R^3$ is selected from $—(CH_2)_nR^6$, $—N=NR^6R^7$, and $—C=CR^6R^7$, wherein n is zero to ten, and $R^6$ and $R^7$ independently are selected from hydrogen, aliphatic, heteroaliphatic, aryl, heteroaryl, or combinations thereof. In other embodiments, n is zero to five or n is zero to two. Typically, $R^6$ is aliphatic, heteroaliphatic, aryl, heteroaryl and $R^7$ is hydrogen. Even more typically $R^6$ is phenyl or pyridyl and is substituted with one or more substituents selected from halogen, alkoxy, cyano, nitro, hydroxyl, thiol, thioether, or combinations thereof.

$R^4$ may be selected from alkyl, cycloalkyl, furfuryl, phenyl, and pyridyl. Typically, $R^4$ is phenyl or pyridyl substituted with one or more substituents selected from halogen, alkoxy, cyano, nitro, hydroxyl, thiol, thioether, trifluoromethyl, or combinations thereof.

In particular disclosed embodiments, $R^5$ may be hydrogen or $—(CH_2)_nC(O)NR^6R^7$.

In particular disclosed embodiments, the compound may have a formula 2, illustrated below.

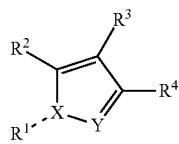

Formula 2

With reference to Formula 2, $R^1$ may be selected from hydrogen, aliphatic, aryl, heteroaliphatic, and heteroaryl, or combinations thereof. Typically, $R^1$ is selected from hydrogen, phenyl, pyridyl, amide, ester, carboxyl, guanidino (or derivatives thereof), thioamide (or derivatives thereof), imidazoline, or combinations thereof. In particular disclosed embodiments, $R^1$ may be phenyl or pyridyl substituted with one or more substituents selected from halogen, alkoxy, cyano, nitro, hydroxyl, thiol, thioether, and combinations thereof.

$R^2$ may be selected from hydrogen, hydroxyl, alkoxy, thiol, thioether, amine, or combinations thereof. In particular disclosed embodiments, $R^2$ may be selected from hydrogen, hydroxyl, or methoxy.

$R^3$ may be selected from hydrogen, aliphatic, aliphatic, heteroaliphatic, heteroaliphatic, aryl, heteroaryl, or combinations thereof. In particular disclosed embodiments, $R^3$ may be selected from —$(CH_2)_nR^6$, —$N$=$NR^6R^7$, and —$C$=$CR^6R^7$, wherein n can range from zero to ten (more typically, from zero to five; even more typically from zero to two), $R^6$ and $R^7$ independently may be selected from hydrogen, aliphatic, heteroaliphatic, aryl, heteroaryl. In particular disclosed embodiments, $R^6$ is aliphatic, heteroaliphatic, aryl, heteroaryl and $R^7$ is hydrogen. More typically, $R^6$ is phenyl or pyridyl and may be substituted with one or more substituents selected from halogen, alkoxy, cyano, nitro, hydroxyl, thiol, thioether, and combinations thereof.

$R^4$ may be selected from aliphatic, heteroaliphatic, aryl, heteroaryl, and combinations thereof. In particular disclosed embodiments, $R^4$ may be selected from alkyl, such as methyl, ethyl, propyl, and butyl; cycloalkyl, such as cyclopropyl, cylcobutyl, cyclopentyl, and cyclohexyl; furfuryl, phenyl, and pyridyl. In particular disclosed embodiments, $R^4$ may be phenyl or pyridyl substituted with one or more substituents selected from halogen, alkoxy, cyano, nitro, hydroxyl, thiol, thioether, trifluoromethyl, and combinations thereof.

X may be selected from nitrogen, oxygen, or carbon. Y may be selected from nitrogen or carbon.

In other embodiments, the compound may have a Formula 3,

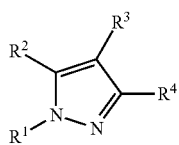

Formula 3 wherein $R^1$, $R^2$, $R^3$, and $R^4$ are as recited herein.

The compound may have a Formula 4

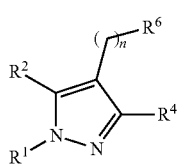

Formula 4 wherein $R^1$, $R^2$, $R^4$, and $R^5$ are as recited herein.

The compound may have a Formula 5

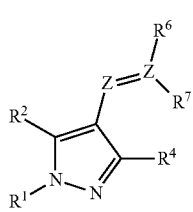

Formula 5 wherein $R^1$, $R^2$, $R^4$, $R^5$, and $R^6$ are as recited herein, and each Z independently may be nitrogen or carbon. More typically, Z is the same and is nitrogen or carbon, $R^5$ is phenyl or pyridyl substituted with one or more halogen, methoxy substituents, or combinations thereof, and $R^6$ is hydrogen.

Also disclosed herein is a pharmaceutical formulation, comprising a compound having any one of Formulas 1-7 as disclosed herein, or a pharmaceutically acceptable salt or ester thereof, and at least one pharmaceutically acceptable carrier, excipient, or combination thereof. The pharmaceutical formulation may further comprise a pharmacologically active agent other than the compound. In particular disclosed embodiments, the pharmacologically active agent is an antiretroviral drug. The antiretroviral drug may be selected from an entry inhibitor, a CCR5 receptor antagonist, a nucleoside reverse transcriptase inhibitor, a non-nucleoside reverse transcriptase inhibitor, a protease inhibitor, an integrase inhibitor, a maturation inhibitor, or combinations thereof. In particular disclosed embodiments, the antiretroviral drug is selected from maraviroc, enfuvirtide, aplaviroc, vicriviroc, zidovudine, didanosine, zalcitabine, stavudine, lamivudine, abacavir, emtricitabine, entecavir, apricitabine, tenofovir, adefovir, efavirenz, nevirapine, delavirdine, etravirine, rilpivirine, saquinavir, ritonavir, indinavir, nelfinavir, amprenavir, lopinavir atazanavir fosamprenavir tipranavir darunavir, MK-2048, elvitegravir, bevirimat, MPC-9055, or combinations thereof.

In particular disclosed embodiments, the pharmaceutical formulation comprises a compound according to any one of Formulas 1-7, as disclosed herein, but not including (E)-4-((3-chlorophenyl)diazenyl)-5-hydroxy-3-(4-nitrophenyl)-1H-pyrazole-1-carbothioamide, 2-{(3Z)-3-[3-(1,1-dioxidotetrahydrothiophen-3-yl)-4-oxo-2-thioxo-1,3-thiazolidin-5-ylidene]-2-oxo-2,3-dihydro-1H-indol-1-yl}-N-(4-methoxyphenyl)acetamide, N-(7-methyl[1,3]thiazolo[4,5-γ][1,3]benzothiazol-2-yl)-2,3-dihydro-1,4-benzodioxine-6-carboxamide, (4Z)-4-[(4-chlorophenyl)hydrazinylidene]-3-(4-nitrophenyl)-5-oxopyrazole-1-carbothioamide, or [4-(2-hydroxybenzoyl)pyrazol-1-yl]-(3-morpholin-4-ylsulfonylphenyl)methanone.

Embodiments of a vaccine adjuvant are also disclosed herein wherein the vaccine adjuvant has a formula according to any one of Formulas 1-7, which are disclosed herein. In particular disclosed embodiments, the vaccine adjuvant is a compound according to any one of Formulas 1-7, as disclosed herein, but not including (E)-4-((3-chlorophenyl)diazenyl)-5-hydroxy-3-(4-nitrophenyl)-1H-pyrazole-1-carbothioamide, 2-{(3Z)-3-[3-(1,1-dioxidotetrahydrothiophen-3-yl)-4-oxo-2-thioxo-1,3-thiazolidin-5-ylidene]-2-oxo-2,3-dihydro-1H-indol-1-yl}-N-(4-methoxyphenyl)acetamide, N-(7-methyl[1,3]thiazolo[4,5-γ][1,3]benzothiazol-2-yl)-2,3-dihydro-1,4-benzodioxine-6-carboxamide, (4Z)-4-[(4-chlorophenyl)hydrazinylidene]-3-(4-nitrophenyl)-5-oxopyrazole-1-carbothioamide, or [4-(2-hydroxybenzoyl)pyrazol-1-yl]-(3-morpholin-4-ylsulfonylphenyl)methanone.

Also disclosed herein is a method for inhibiting a biological function of Nef, comprising contacting Nef with an effective amount of a compound disclosed herein. The biological function of Nef may be selected from HIV infectivity, HIV replication, and AIDS progression. The compound may have a Formula 1, illustrated below,

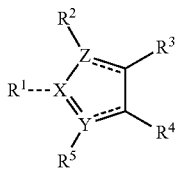

Formula 1 wherein $R^1$ is selected from hydrogen, aliphatic, aryl, heteroaliphatic, oxo, heteroaryl, or combinations thereof; $R^2$ is selected from hydrogen, aliphatic, heteroaliphatic, hydroxyl, alkoxy, thiol, thioether, amine, or combinations thereof; $R^3$ is selected from hydrogen, aliphatic, heteroaliphatic, aryl, heteroaryl, or combinations thereof; $R^4$ is selected from hydrogen, aliphatic, heteroaliphatic, aryl, heteroaryl, and combinations thereof; $R^3$ and $R^4$ can be joined together to form a 5-, 6-, 7-, or 8-membered saturated or unsaturated ring, optionally comprising one or more heteroatoms and optionally substituted with one or more substituents selected from aliphatic, heteroaliphatic, halogen, aryl, or heteroaryl; $R^5$ is selected from hydrogen, aliphatic, heteroaliphatic, aryl, heteroaryl, and combinations thereof; X is selected from nitrogen, oxygen, or carbon; Y is selected from nitrogen or carbon; Z may be selected from carbon, sulfur, and nitrogen. In particular disclosed embodiments, $R^1$ is selected from hydrogen, phenyl, pyridyl, amide, ester, carboxyl, guanidino (or derivatives thereof), thioamide (or derivatives thereof), imidazoline, keto, amide, oxo, or combinations thereof. $R^1$ may be selected from phenyl or pyridyl substituted with one or more substituents selected from halogen, alkoxy, cyano, nitro, hydroxyl, thiol, thioether, and combinations thereof. In other embodiments, $R^1$ is selected from keto or amido substituted with an aromatic substituent selected from ethylenedioxyphenyl, phenyl sulfonyl, phenyl sulfonylamino, and combinations thereof.

Certain embodiments of the method concern a compound wherein $R^2$ may be selected from hydrogen, hydroxyl, substituted exomethylene, or methoxy. $R^3$ may be selected from —$(CH_2)_nR^6$, —N=$NR^6R^7$, and —C=$CR^6R^7$, wherein n can range from zero to ten, and $R^6$ and $R^7$ independently may be selected from hydrogen, aliphatic, heteroaliphatic, aryl, or heteroaryl. In particular disclosed embodiments, $R^6$ is phenyl or pyridyl and is optionally substituted with one or more substituents selected from halogen, alkoxy, cyano, nitro, hydroxyl, thiol, thioether, and combinations thereof. $R^4$ may be selected from alkyl, cycloalkyl, furfuryl, phenyl, and pyridyl. In other disclosed embodiments, $R^3$ and $R^4$ may be joined together to form a phenyl ring optionally substituted with one or more halogen, alkoxy, cyano, nitro, hydroxyl, thiol, thioether, and combinations thereof. $R^5$ may be hydrogen or —$(CH_2)_nC(O)NR^6R^7$.

In particular disclosed embodiments of the method, the compound has a Formula 2,

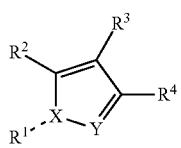

Formula 2 wherein $R^1$, $R^2$, $R^3$, $R^4$, X, and Y are as recited herein.

In further disclosed embodiments, the compound has a Formula 3,

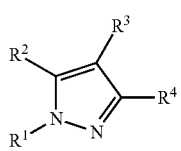

Formula 3 wherein $R^1$, $R^2$, $R^3$, and $R^4$ are as recited herein.

In even further disclosed embodiments, the compound has a Formula 4,

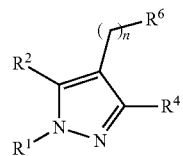

Formula 4 wherein $R^1$, $R^2$, $R^4$, $R^6$, and n are as recited herein.

In yet other embodiments of the method, the compound has a Formula 5,

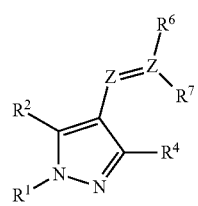

Formula 5 wherein $R^1$, $R^2$, $R^4$, $R^6$, $R^7$, and Z are as recited herein.

In other disclosed embodiments, the compound has a Formula 6,

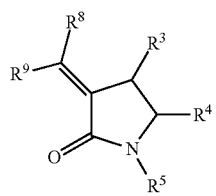

Formula 6 wherein $R^8$ and $R^9$ may be joined together to form a 5-, 6-, 7-, or 8-membered saturated or unsaturated ring optionally comprising one or more heteroatoms, and wherein $R^3$, $R^4$, $R^5$, and n are as recited herein.

Further embodiments of the disclosed method concern a compound having a Formula 7,

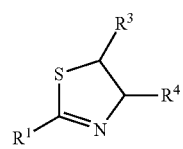

Formula 7 wherein $R^1$, $R^3$, and $R^4$ are as recited herein.

Exemplary compounds that may be used in the disclosed method are provided herein.

A method of inhibiting an activity of a Nef-dependent kinase comprising contacting the Nef-dependent kinase with an effective amount of a compound disclosed herein is also contemplated by the present disclosure. In particular disclosed embodiments, the Nef-dependent kinase is coupled with Nef.

Also disclosed is a method of treating a Nef-mediated disease, comprising administering to a subject an effective amount of a compound disclosed herein. Further embodiments concern a method of treating HIV, comprising administering to a subject an effective amount of a compound disclosed herein.

Particular disclosed embodiments concern a method of treating an HIV-related condition comprising administering to a subject an effective amount of a compound disclosed herein. The HIV-related condition may be selected from HIV replication, HIV-associated CD4+ T-cell loss and immunodeficiency, HIV-induced infection, Kaposi's sarcoma, HIV-associated nephropathy, AIDS dementia complex, and combinations thereof. The subject may be suffering from the HIV-related condition. Also, the subject may be administered the compound prophylactically. In other embodiments, the subject may be administered the compound post-exposure prophylactically.

The effective amount disclosed herein may range from greater than zero to about 1000 mg/kg/day. More typically, the amount ranges from about 1 mg/kg/day to about 100 mg/kg/day.

The compound may also be administered as a formulation. The formulation may comprise the compound and a pharmaceutically acceptable carrier. The formulation also may further comprise at least one antiretroviral drug, as disclosed herein. The subject may be an animal or human, and any one of the disclosed embodiments of the method may be performed in vitro or in vivo.

Also disclosed is a method for identifying antimicrobial agents, comprising coupling Nef with a kinase to form a complex, and exposing the complex to one or more compounds selected from any one of compounds disclosed herein. The kinase may be a Src-family kinase, such as Hck.

Also disclosed herein is a kit comprising a compound as disclosed herein, or a pharmaceutically acceptable salt, or an ester thereof. Also, a kit comprising the pharmaceutical formulation disclosed herein is also contemplated.

The foregoing and other objects, features, and advantages of the invention will become more apparent from the following detailed description, which proceeds with reference to the accompanying figures.

BRIEF DESCRIPTION OF THE DRAWINGS

FIG. 17 is a graph illustrating surface plasmon resonance data obtained from flowing various concentrations of an exemplary embodiment of the disclosed compound past recombinant purified HIV-1 Nef-SF2 immobilized on the surface of a Biacore CM5 chip.

FIG. 18 is a graph illustrating surface plasmon resonance data fit by a two-state model.

FIG. 19 is a graph illustrating surface plasmon resonance data obtained from flowing a constant concentration of an exemplary embodiment of the disclosed compound over wild-type (WT) Nef and three Nef mutants in which Asn126 is replaced with Leu, Gln, or Ala as shown.

FIG. 20 is a graph illustrating results obtained from a Z'-Lyte kinase assay and Tyr2 peptide substrate either alone or in the presence of a 10-fold molar excess of wild-type Nef (WT) or three Asn126 mutants (N126L, N126Q, and N126A).

DETAILED DESCRIPTION

I. Terms

Figure 1:
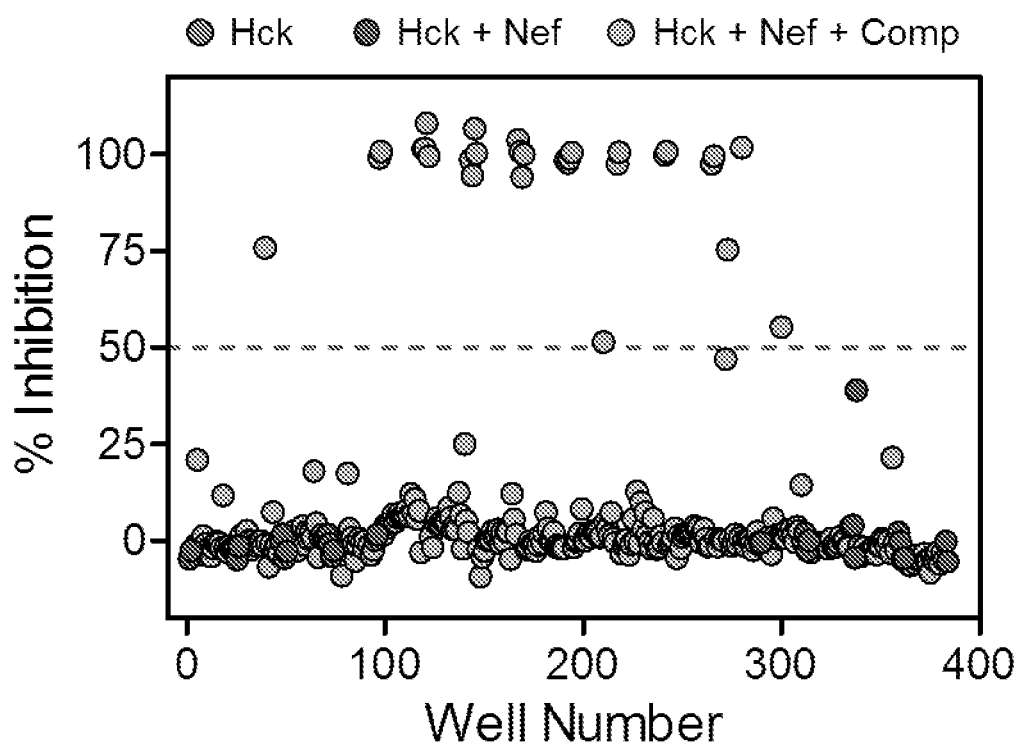
FIG. 1 is a scatterplot of results obtained from using the NIH Molecular Libraries Screen Centers Network (MLSCN) library using the disclosed FRET-based Nef:Hck in vitro kinase assay.

Unless otherwise explained, all technical and scientific terms used herein have the same meaning as commonly understood by one of ordinary skill in the art to which a disclosed technology belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well.

Alkyl: A saturated aliphatic group comprising carbon and hydrogen atoms, typically having from 1 to about 10 carbon atoms, more typically from 1 to about 6 carbon atoms. This term includes straight chain alkyl groups as well as branched alkyl groups. Exemplary alkyl groups include methyl, ethyl, n-propyl, i-propyl, n-butyl, i-butyl, sec-butyl, t-butyl, n-pentyl, neopentyl, and n-hexyl. This term includes substituted alkyl groups, which are alkyl groups having from 1 to 5 hydrogen atoms being replaced with any substituent recited herein.

Alkoxy: This term includes alkyl groups comprising an oxygen atom, such as —OMe, —OEt, and the like. This term also includes oxygen-containing substituted alkyl groups, which are alkyl groups having from 1 to 5 hydrogen atoms being replaced with any substituent recited herein.

Amide: This term refers to the group —C(O)NH$_2$. This term also includes substituted amide groups having a formula —C(O)NR$^7$R$^8$ wherein R$^7$ and R$^8$ may be selected from hydrogen, aliphatic, heteroaliphatic, aryl, and heteroaryl.

Amino: This term refers to the group —NH$_2$. This term also includes substituted amino groups having a formula NR$^7$R$^8$ wherein R$^7$ and R$^8$ may be selected from hydrogen, aliphatic, heteroaliphatic, aryl, and heteroaryl.

Aryl: An aromatic cyclic group comprising from 6 to about 14 carbon atoms. The carbon atoms may comprise a single ring, or one or more fused rings wherein at least one of the fused rings is aromatic. Exemplary embodiments are phenyl, naphthyl or anthryl. This term includes aryl groups having 1 to 5 hydrogen atoms replaced with any substituent provided herein.

Carboxyl: This term refers to the group —C(O)OH, or a salt thereof.

Cyano: This term refers to the group —CN.

Cycloalkyl: This term refers to a cyclic alkyl group comprising from 3 to about 10 carbon atoms having one or more rings.

Ester: This term refers to a carboxyl group substituted with an alkyl group, such as methyl, ethyl, propyl, and the like. Exemplary embodiments are —C(O)OMe and —C(O)OEt.

Guanidino: This term refers to the group —NHC(=NH)NH$_2$ and also encompasses substituted guanidino groups having a formula —NHC(=NH)NR$^7$R$^8$ wherein R$^7$ and R$^8$ may be selected from hydrogen, aliphatic, heteroaliphatic, aryl, and heteroaryl.

Halogen (or Halo): This term includes fluoro, iodo, bromo, and chloro.

Heteroaliphatic: This term refers to an aliphatic group comprising at least one heteroatom selected from oxygen, sulfur, and nitrogen.

Heteroaryl: This term refers to an aromatic group comprising from 5 to about 15 atoms in the ring, wherein at least one of those atoms is a heteroatom selected from oxygen, nitrogen, or sulfur. This term includes single rings and fused ring systems. This term also includes substituted heteroaryl groups comprising from 1 to about 5 substituents selected from the groups provided herein.

Heterocyclic: This term refers to a saturated or unsaturated cyclic group comprising from 1 to about 10 carbon atoms and at least one heteroatom selected from oxygen, nitrogen, or sulfur. This term also includes substituted heterocyclic groups comprising from 1 to about 5 substituents attached to at least one carbon atom of the ring, wherein the substituent may be selected from any substituent disclosed herein.

Hydroxyl: This term refers to the group —OH.

Nitro: This term refers to the group —NO$_2$.

Prodrug: This term refers, typically, to a pharmacologically inactive derivative of the disclosed compound that may be converted to an active form of the disclosed compound by removal of a progroup. The compounds disclosed herein may exist as a prodrug, wherein one or more of the functional groups on the compound is converted into a progroup. In particular disclosed embodiments, the compound may comprise a hydroxyl group, an amine group, a thiol group, or a carboxyl group that is converted into a progroup. Solely by way of example, a hydroxyl group may be functionalized to provide a sulfonate (e.g., mesylate, triflate, tosylate, and the like), an ester group, or an alkyl group. Solely by way of example, an amine may be functionalized to provide an amide group or an ester group. Solely by way of example, a carboxyl group may be functionalized to provide an ester group or an amide group.

Progroup: This term refers to a protecting group that may be attached to a functional group present on the disclosed compound(s) via one or more bonds that may be cleaved under particular conditions, such as acidic conditions, hydrolysis conditions, or enzymatic cleavage conditions.

Pyridyl: This term refers to the aromatic group —C$_5$H$_4$N. As disclosed herein, this group may be substituted with one or more substituents recited herein.

Thio (or Thiol): This term refers to the group —SH.

Thioether: This term refers to a thio group substituted with an aliphatic group, such as an alkyl group, as defined herein. This term also includes substituted thioether groups comprising substituted alkyl groups, as defined herein.

Treat(ing/ed/ment): This term refers to inhibiting a disease, condition, or disorder, such as by preventing it from developing, worsening, progressing, and the like. This term also refers to ameliorating symptoms of, or causing regression of, a disease, condition, or disorder.

II. HIV-Nef Function Antagonist

In addition to viral enzymes and structural proteins, the HIV-1 genome encodes a unique set of accessory factors (Vpr, Vpu, Vif, and Nef) that are essential for viral pathogenesis and represent underexplored targets for new antiretroviral drug discovery. HIV-1 Nef is particularly attractive in this regard, as it enhances HIV infectivity, promotes viral replication, and enables immune escape of HIV-infected cells. Nef lacks known biochemical activity, functioning instead through interactions with a myriad of host cell proteins. These interactions provide a molecular basis for many Nef functions, including downregulation of viral (CD4/CXCR4/CCR5) and immune (MHC-I) receptors from the host cell surface. Nef-mediated receptor internalization is believed to prevent superinfection and enhance viral release, while MHC-I downregulation promotes evasion of immune surveillance by the host.

A critical role for Nef in HIV disease has also been established in animal models as well as AIDS patients. Nef is required for the high-titer replication of both HIV and SIV in vivo, and is essential for the development of AIDS-like disease in non-human primates. Furthermore, targeted expression of Nef in the T-cells and macrophages of transgenic mice induces a severe AIDS-like syndrome, strongly supporting an essential role for this single viral protein in HIV-1 pathogenesis. The phenotype of these Nef-transgenic mice recapitulates many aspects of human AIDS, including profound immunodeficiency, loss of CD4+ T cells, thymic atrophy, persistent T-cell activation, as well as kidney, spleen, and lung pathology. In contrast, HIV strains with defective nef alleles have been isolated from patients with long-term, non-progressive HIV infections. Similarly, CD4+ T-cell depletion and immunosuppression was greatly delayed in a cohort of individuals infected with a Nef-deficient HIV-1 quasispecies, providing strong clinical evidence that Nef is essential for disease progression in humans.

Disclosed herein are embodiments of a compound for treating HIV. In particular disclosed embodiments, the compound is capable of inhibiting Nef, such as by acting as a HIV-Nef function antagonist. The compound is a small molecule compound that is capable of inhibiting both HIV-1 infectivity and replication. The compound may be active against HIV-1 replication supported by Nef alleles representative of all major subtypes of HIV-1. The disclosed compound is capable of binding to Nef and thereby altering or inhibiting its activity. In particular disclosed embodiments, the compound may bind electrostatically, via hydrogen bonding, or covalently.

The compound disclosed herein may be an HIV-Nef function antagonist having a general Formula 1, illustrated below, or a pharmaceutically acceptable salt, or ester thereof. In particular disclosed embodiments, the compound is not (E)-4-((3-chlorophenyl)diazenyl)-5-hydroxy-3-(4-nitrophenyl)-1H-pyrazole-1-carbothioamide, 2-{(3Z)-3-[3-(1,1-dioxidotetrahydrothiophen-3-yl)-4-oxo-2-thioxo-1,3-thiazolidin-5-ylidene]-2-oxo-2,3-dihydro-1H-indol-1-yl}-N-(4-methoxyphenyl)acetamide, N-(7-methyl[1,3]thiazolo[4,5-γ][1,3]benzothiazol-2-yl)-2,3-dihydro-1,4-benzodioxine-6-carboxamide, (4Z)-4-[(4-chlorophenyl)hydrazinylidene]-3-(4-nitrophenyl)-5-oxopyrazole-1-carbothioamide, or [4-(2-hydroxybenzoyl)pyrazol-1-yl]-(3-morpholin-4-ylsulfonylphenyl)methanone.

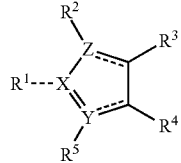

Formula 1

With reference to Formula 1, R$^1$ may be selected from hydrogen, aliphatic, aryl, heteroaliphatic, oxo, heteroaryl, or combinations thereof. In these embodiments, R$^1$ typically is selected from hydrogen, phenyl, pyridyl, amide, ester, carboxyl, guanidino (or derivatives thereof), thioamide (or derivatives thereof), imidazoline, keto, amide, oxo, or combinations thereof. In particular disclosed embodiments, R$^1$ may be phenyl or pyridyl substituted with one or more substituents selected from halogen, alkoxy, cyano, nitro, hydroxyl, thiol, thioether, and combinations thereof. In other disclosed embodiments, $R^1$ may be keto or amido substituted with an aromatic substituent selected from ethylenedioxyphenyl, phenyl sulfonyl, phenyl sulfonylamino, and combinations thereof.

$R^2$ may be selected from hydrogen, aliphatic, heteroaliphatic, hydroxyl, alkoxy, thiol, thioether, amine, or combinations thereof. In particular disclosed embodiments, $R^2$ may be selected from hydrogen, hydroxyl, substituted exomethylene, or methoxy.

$R^3$ may be selected from hydrogen, aliphatic, heteroaliphatic, aryl, heteroaryl, or combinations thereof. In particular disclosed embodiments, $R^3$ may be selected from —$(CH_2)_nR^6$, —$N=NR^6R^7$, and —$C=CR^6R^7$, wherein n can range from zero to ten (more typically, from zero to five; even more typically from zero to two), $R^6$ and $R^7$ independently may be selected from hydrogen, aliphatic, heteroaliphatic, aryl, heteroaryl. In particular disclosed embodiments, $R^6$ is aliphatic, heteroaliphatic, aryl, heteroaryl and $R^7$ is hydrogen. More typically, $R^6$ is phenyl or pyridyl and may be substituted with one or more substituents selected from halogen, alkoxy, cyano, nitro, hydroxyl, thiol, thioether, and combinations thereof. $R^6$ and $R^7$ may be positioned to provide a compound having either Z- or E-olefin geometry.

$R^4$ may be selected from hydrogen, aliphatic, heteroaliphatic, aryl, heteroaryl, and combinations thereof. In particular disclosed embodiments, $R^4$ may be selected from alkyl, such as methyl, ethyl, propyl, and butyl; cycloalkyl, such as cyclopropyl, cyclobutyl, cyclopentyl, and cyclohexyl; furfuryl; phenyl; and pyridyl. In particular disclosed embodiments, $R^4$ may be phenyl or pyridyl substituted with one or more substituents selected from halogen, alkoxy, cyano, nitro, hydroxyl, thiol, thioether, trifluoromethyl, and combinations thereof.

In particular disclosed embodiments, $R^3$ and $R^4$ may be joined together to form a 5-, 6-, 7-, or 8-membered saturated or unsaturated ring, optionally comprising one or more heteroatoms and optionally substituted with one or more substituents selected from aliphatic, heteroaliphatic, halogen, aryl, or heteroaryl. Typically, $R^3$ and $R^4$ are joined together to form an aromatic ring thereby forming a compound having a fused ring system. In particular disclosed embodiments, $R^3$ and $R^4$ are joined together to form a phenyl ring optionally substituted with one or more substituents disclosed herein. Additionally, the phenyl ring may be substituted with two substituents that are joined together to form a ring, thereby providing a fused ring system comprising three rings.

$R^5$ may be selected from hydrogen, aliphatic, heteroaliphatic, aryl, heteroaryl, and combinations thereof. In particular disclosed embodiments, $R^5$ is hydrogen or —$(CH_2)_nC(O)NR^6R^7$ wherein n, $R^6$, and $R^7$ are as previously defined.

X may be selected from nitrogen, oxygen, or carbon. Y may be selected from nitrogen or carbon. Z may be selected from carbon, sulfur, and nitrogen.

In particular disclosed embodiments, if $R^1$ is oxo, then X is carbon and there is no double bond between X and Y. In other disclosed embodiments, if X is oxygen, then the compound does not comprise an $R^1$ substituent and there is no double bond between X and Y. In other embodiments, if X is nitrogen and $R^1$ is present, there is no double bond between X and Y. In particular disclosed embodiments, Y is nitrogen, bound to $R^5$, and there is no double bond between the carbon atom bearing $R^4$ and Y, or between X and Y.

The compound may have a formula 2, illustrated below.

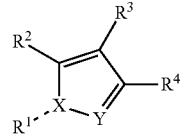

Formula 2

With reference to Formula 2, $R^1$ may be selected from hydrogen, aliphatic, aryl, heteroaliphatic, and heteroaryl, or combinations thereof. Typically, $R^1$ is selected from hydrogen, phenyl, pyridyl, amide, ester, carboxyl, guanidino (or derivatives thereof), thioamide (or derivatives thereof), imidazoline, or combinations thereof. In particular disclosed embodiments, $R^1$ may be phenyl or pyridyl substituted with one or more substituents selected from halogen, alkoxy, cyano, nitro, hydroxyl, thiol, thioether, and combinations thereof.

$R^2$ may be selected from hydrogen, hydroxyl, alkoxy, thiol, thioether, amine, or combinations thereof. In particular disclosed embodiments, $R^2$ may be selected from hydrogen, hydroxyl, or methoxy.

$R^3$ may be selected from hydrogen, aliphatic, aliphatic, heteroaliphatic, heteroaliphatic, aryl, heteroaryl, or combinations thereof. In particular disclosed embodiments, $R^3$ may be selected from —$(CH_2)_nR^6$, —$N=NR^6R^7$, and —$C=CR^6R^7$, wherein n can range from zero to ten (more typically, from zero to five; even more typically from zero to two), $R^6$ and $R^7$ independently may be selected from hydrogen, aliphatic, heteroaliphatic, aryl, heteroaryl. In particular disclosed embodiments, $R^6$ is aliphatic, heteroaliphatic, aryl, heteroaryl and $R^7$ is hydrogen. More typically, $R^6$ is phenyl or pyridyl and may be substituted with one or more substituents selected from halogen, alkoxy, cyano, nitro, hydroxyl, thiol, thioether, and combinations thereof.

$R^4$ may be selected from aliphatic, heteroaliphatic, aryl, heteroaryl, and combinations thereof. In particular disclosed embodiments, $R^4$ may be selected from alkyl, such as methyl, ethyl, propyl, and butyl; cycloalkyl, such as cyclopropyl, cylcobutyl, cyclopentyl, and cyclohexyl; furfuryl, phenyl, and pyridyl. In particular disclosed embodiments, $R^4$ may be phenyl or pyridyl substituted with one or more substituents selected from halogen, alkoxy, cyano, nitro, hydroxyl, thiol, thioether, trifluoromethyl, and combinations thereof.

X may be selected from nitrogen, oxygen, or carbon. Y may be selected from nitrogen or carbon.

In particular disclosed embodiments, the compound may be an HIV-Nef function antagonist having a general Formula 3, illustrated below, or a pharmaceutically acceptable salt, or ester thereof.

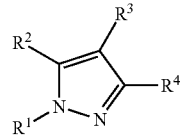

Formula 3

With reference to Formula 3, $R^1$, $R^2$, $R^3$, and $R^4$ may be as described above for Formula 2.

The compound may be an HIV-Nef function antagonist having a general Formula 4, as illustrated below, or a pharmaceutically acceptable salt, or ester thereof.

Formula 4

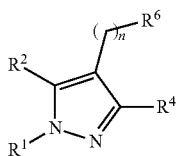

With reference to Formula 4, $R^1$, $R^2$, $R^4$, and $R^5$ may be as previously recited for Formula 2.

In other disclosed embodiments, the compound may be an HIV-Nef function antagonist having a general Formula 5, below, or a pharmaceutically acceptable salt, or ester thereof.

Formula 5

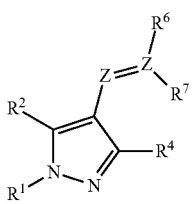

With reference to Formula 5, $R^1$, $R^2$, $R^4$, $R^6$, and $R^7$ may be as previously recited for Formula 2 and each Z independently may be nitrogen or carbon. In particular disclosed embodiments, each Z is nitrogen or carbon, $R^6$ is phenyl or pyridyl substituted with one or more halogen (such as chloro, fluoro, bromo, or iodo), methoxy substituents, or combinations thereof, and $R^7$ is hydrogen.

In other disclosed embodiments, the compound may have a Formula 6, illustrated below.

Formula 6

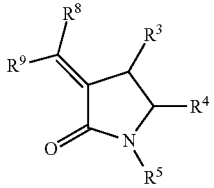

With reference to Formula 6, $R^3$, $R^4$, and $R^5$ may be as previously recited for Formula 1. $R^8$ and $R^9$ may be joined together to form a 5-, 6-, 7-, or 8-membered saturated or unsaturated ring optionally comprising one or more heteroatoms.

In particular disclosed embodiments, the compound may have a Formula 7, illustrated below.

Formula 7

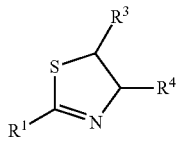

With reference to Formula 7, $R^3$, $R^4$, and $R^5$ may be as previously recited for Formula 1. In particular disclosed embodiments, $R^1$ is an amide optionally substituted with an aromatic group. In exemplary embodiments, $R^1$ is an amide substituted with an ethylenedioxyphenyl group.

Exemplary embodiments of the disclosed HIV-Nef function antagonist are provided below.

B-9

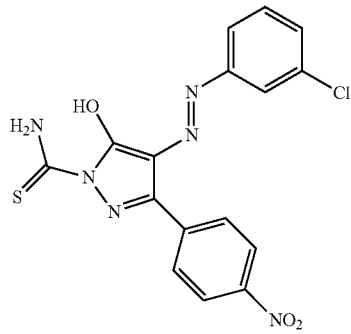

$C_{16}H_{11}ClN_6O_3S$
Exact Mass: 402.0302

PCl-I-30

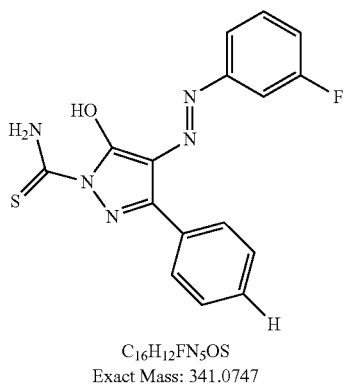

$C_{16}H_{12}FN_5OS$
Exact Mass: 341.0747

PCl-I-23

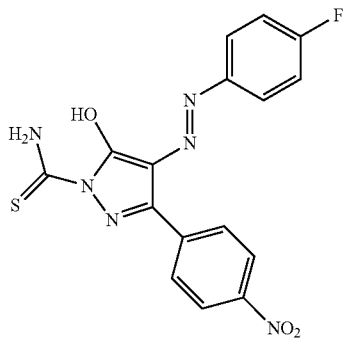

$C_{16}H_{11}FN_6O_3S$
Exact Mass: 386.0597

-continued
PCl-I-29
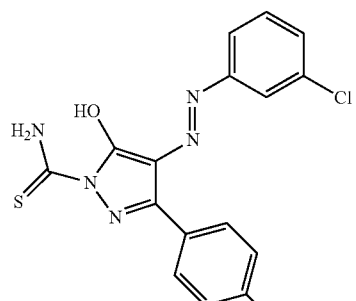
C$_{16}$H$_{12}$ClN$_5$OS
Exact Mass: 357.0451
KM-I-42
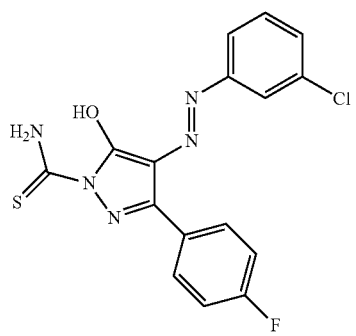
C$_{16}$H$_{11}$ClFN$_5$OS
Exact Mass: 375.0357
PCl-I-06
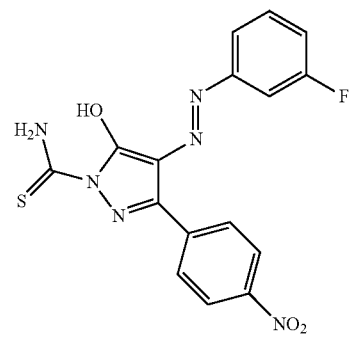
C$_{16}$H$_{11}$FN$_6$O$_3$S
Exact Mass: 386.0597
KM-1-46
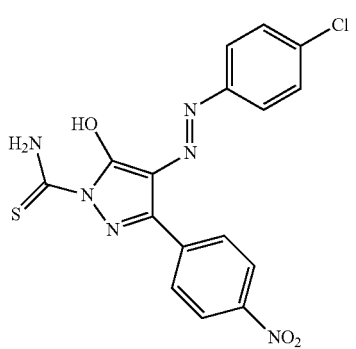
C$_{16}$H$_{11}$ClN$_6$O$_3$S
Exact Mass: 402.0302
-continued
KM-1-48
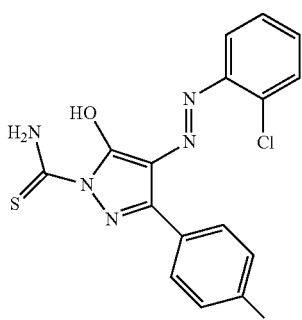
C$_{16}$H$_{11}$ClN$_6$O$_3$S
Exact Mass: 402.0302
PCl-1-25
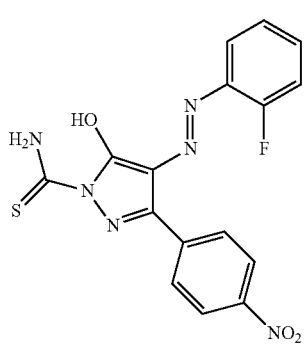
C$_{16}$H$_{11}$FN$_6$O$_3$S
Exact Mass: 386.0597
PCl-1-55
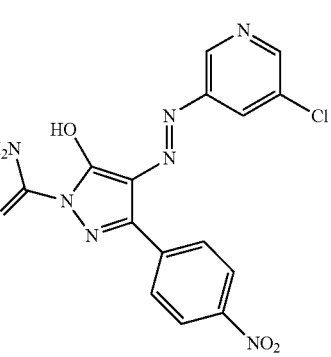
C$_{15}$H$_{10}$ClN$_7$O$_3$S
Exact Mass: 403.0254
PCl-1-50
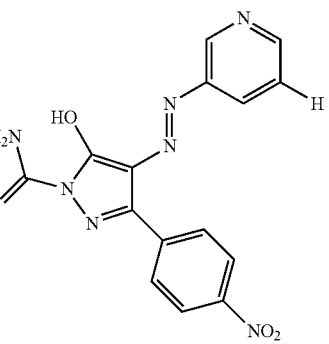
C$_{15}$H$_{11}$N$_7$O$_3$S
Exact Mass: 369.0644

-continued
PCl-1-52
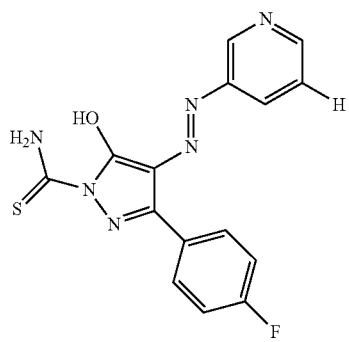
C₁₅H₁₁FN₆OS
Exact Mass: 342.0699
JZ-1-49
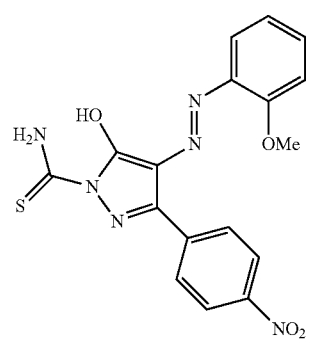
C₁₇H₁₄N₆O₄S
Exact Mass: 398.0797
JZ-1-56
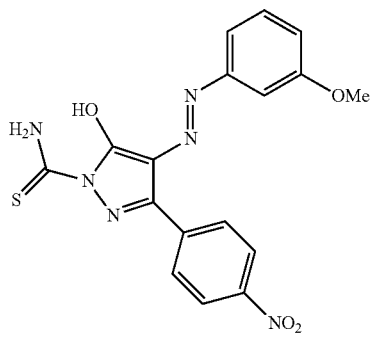
C₁₇H₁₄N₆O₄S
Exact Mass: 398.0797
JZ-1-107
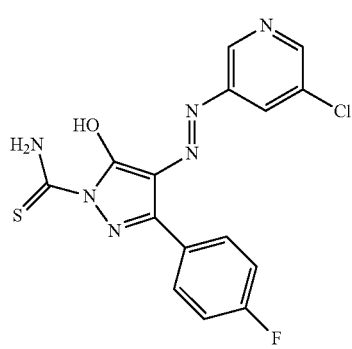
C₁₅H₁₀ClFN₆OS
Exact Mass: 376.0309
-continued
JZ-1-58-3
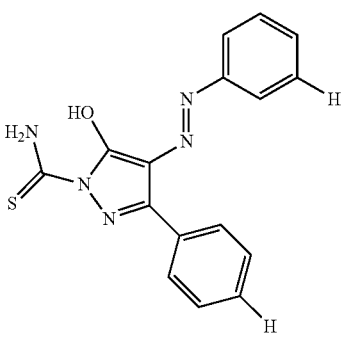
C₁₆H₁₃N₅OS
Exact Mass: 323.0841
JZ-1-62
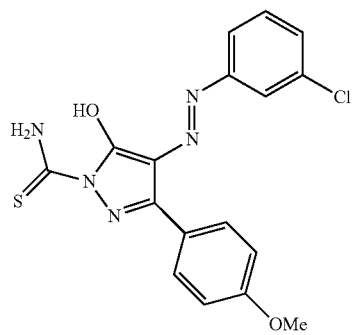
C₁₇H₁₄ClN₅O₂S
Exact Mass: 387.0557
JZ-1-64
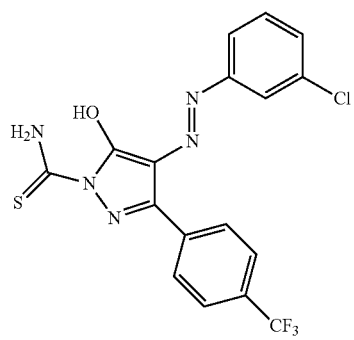
C₁₇H₁₁ClF₃N₅OS
Exact Mass: 425.0325
JZ-1-101
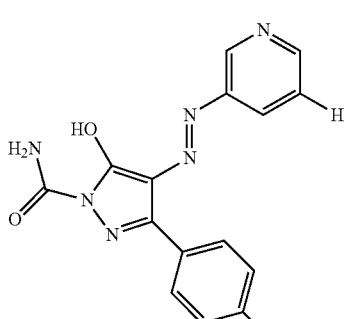
C₁₅H₁₁FN₆O₂
Exact Mass: 326.0928

-continued
JZ-1-106
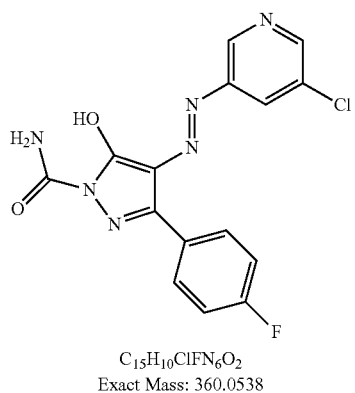
C₁₅H₁₀ClFN₆O₂
Exact Mass: 360.0538
PCl-1-43
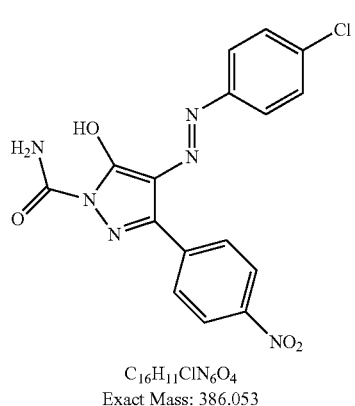
C₁₆H₁₁ClN₆O₄
Exact Mass: 386.053
PCl-1-45
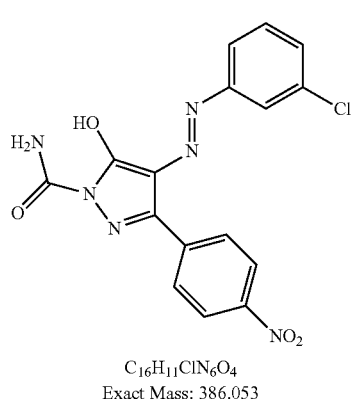
C₁₆H₁₁ClN₆O₄
Exact Mass: 386.053
PCl-1-48
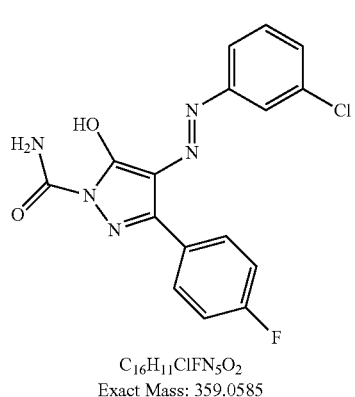
C₁₆H₁₁ClFN₅O₂
Exact Mass: 359.0585
-continued
PCl-1-53
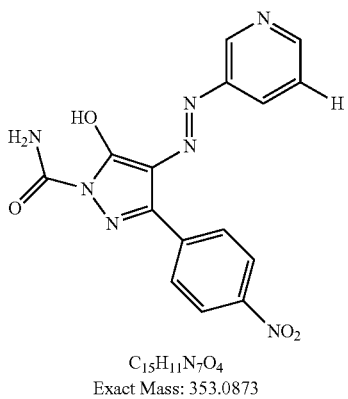
C₁₅H₁₁N₇O₄
Exact Mass: 353.0873
PCl-1-56
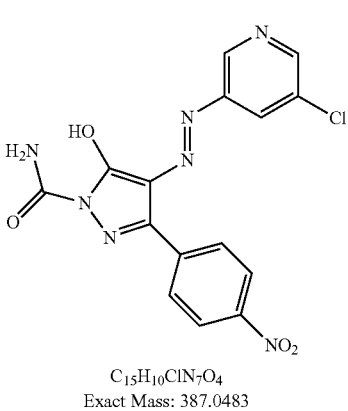
C₁₅H₁₀ClN₇O₄
Exact Mass: 387.0483
JV-2-2
JV-2-21
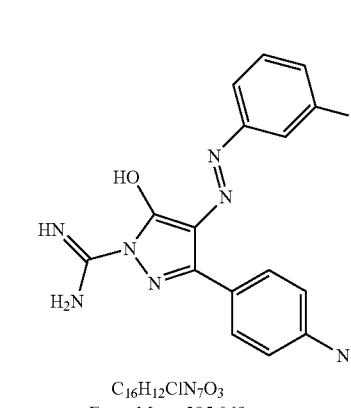
C₁₆H₁₂ClN₇O₃
Exact Mass: 385.069
JZ-1-50
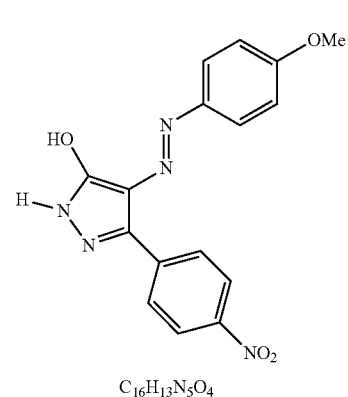
C₁₆H₁₃N₅O₄
Exact Mass: 339.0968

-continued
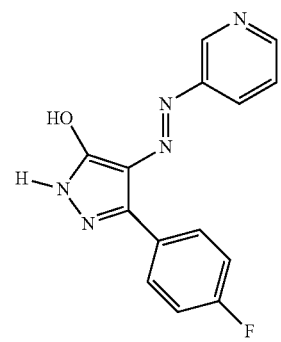
JZ-1-110-1
C₁₄H₁₀FN₅O
Exact Mass: 283.0869
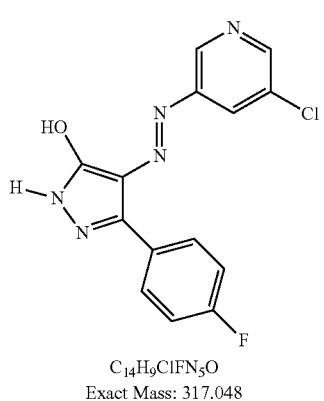
JZ-1-110-2
C₁₄H₉ClFN₅O
Exact Mass: 317.048
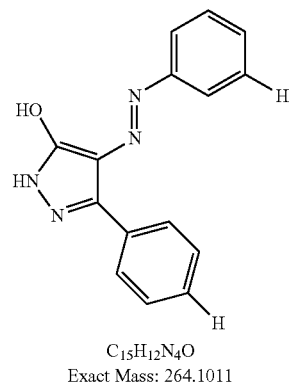
JZ-1-58-2
C₁₅H₁₂N₄O
Exact Mass: 264.1011
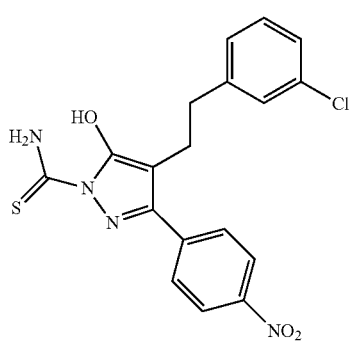
JZ-1-96-2-1
C₁₈H₁₅ClN₄O₃S
Exact Mass: 402.0553
-continued
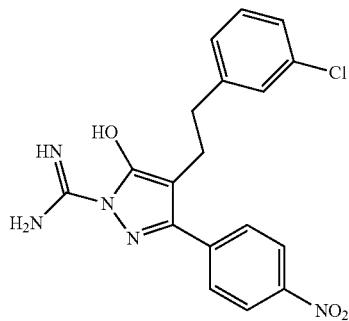
JV-1-62-2-1
C₁₈H₁₆ClN₅O₃
Exact Mass: 385.0942
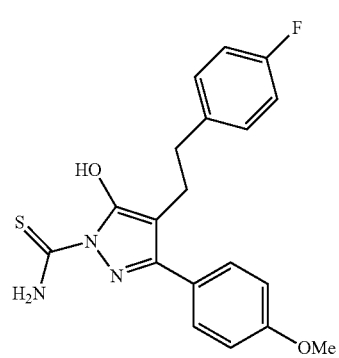
JV-1-94
JZ-1-198
C₁₉H₁₈FN₃O₂S
Exact Mass: 371.1104
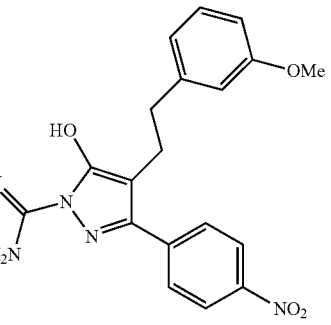
JZ-1-135-1
C₁₉H₁₉N₅O₄
Exact Mass: 381.1437
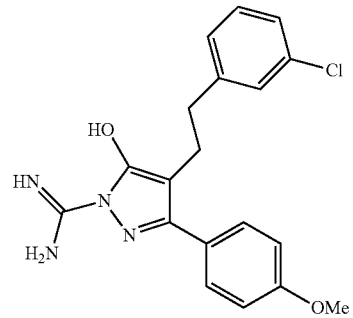
JV-1-62-1
C₁₉H₁₉ClN₄O₂
Exact Mass: 370.1197

-continued
JV-1-67-1
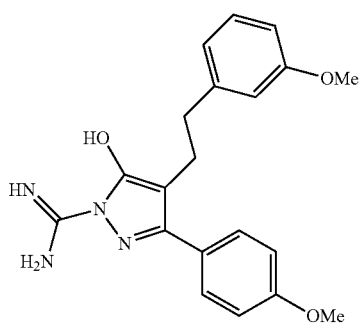
C20H22N4O3
Exact Mass: 366.1692
JV-1-74-1
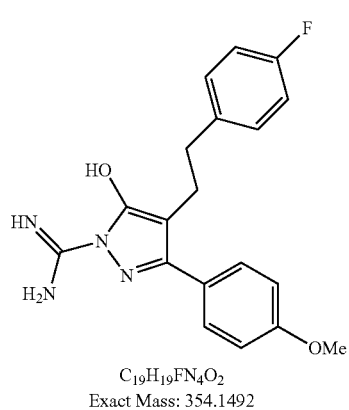
C19H19FN4O2
Exact Mass: 354.1492
JZ-1-135-2
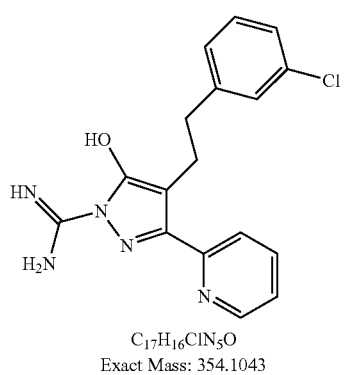
C17H16ClN5O
Exact Mass: 354.1043
JV-1-89
JZ-1-197
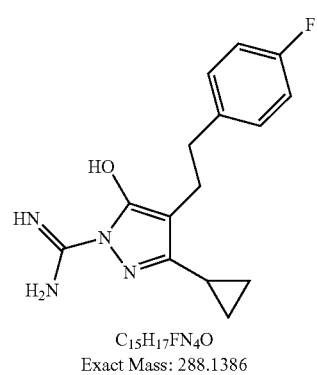
C15H17FN4O
Exact Mass: 288.1386
-continued
JV-1-87
JZ-1-207
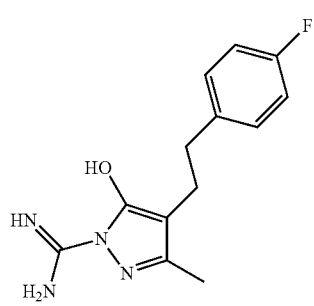
C13H15FN4O
Exact Mass: 262.123
JV-1-96
JZ-1-208
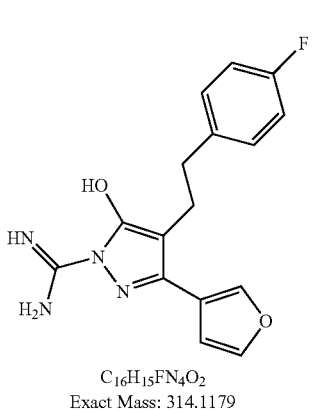
C16H15FN4O2
Exact Mass: 314.1179
JZ-1-154-2-2
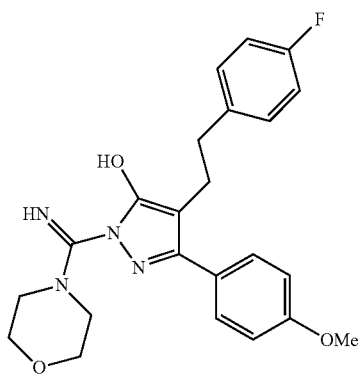
C23H25FN4O3
Exact Mass: 424.1911
JV-1-74-2
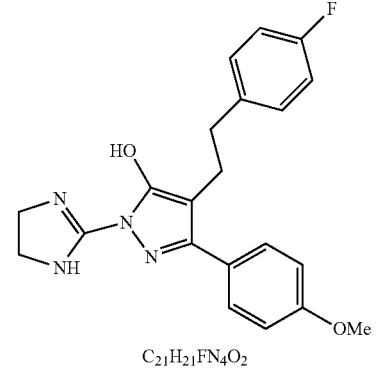
C21H21FN4O2
Exact Mass: 380.1649

-continued
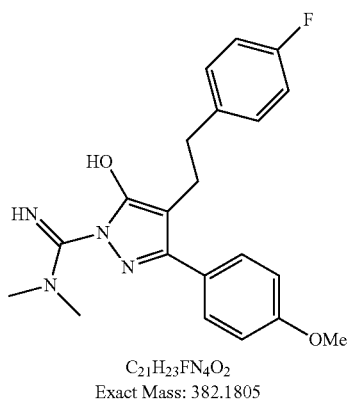
JV-2-3
C₂₁H₂₃FN₄O₂
Exact Mass: 382.1805
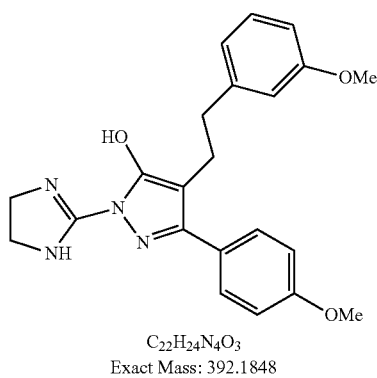
JV-1-71-1
C₂₂H₂₄N₄O₃
Exact Mass: 392.1848
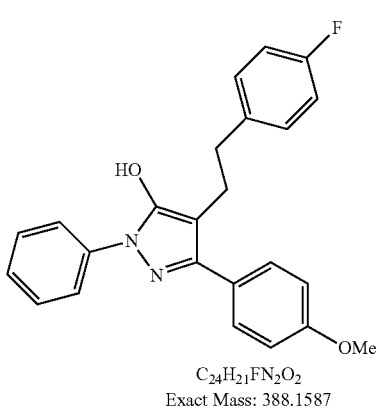
JV-1-79
JZ-1-203
C₂₄H₂₁FN₂O₂
Exact Mass: 388.1587
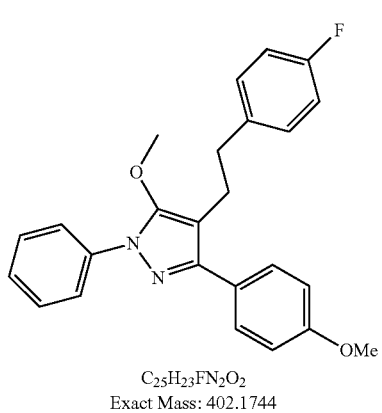
JV-1-81
C₂₅H₂₃FN₂O₂
Exact Mass: 402.1744
-continued
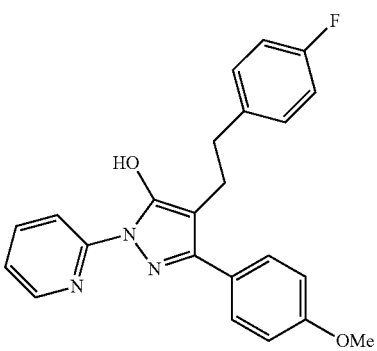
JV-1-80
JZ-1-195
C₂₃H₂₀FN₃O₂
Exact Mass: 389.154
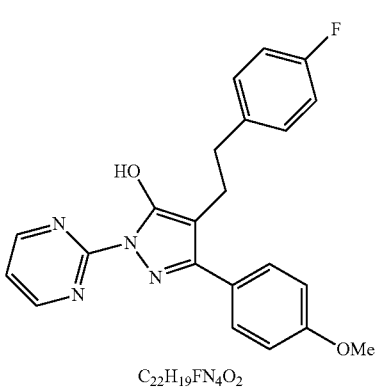
JV-1-97
JZ-1-206
C₂₂H₁₉FN₄O₂
Exact Mass: 390.1492
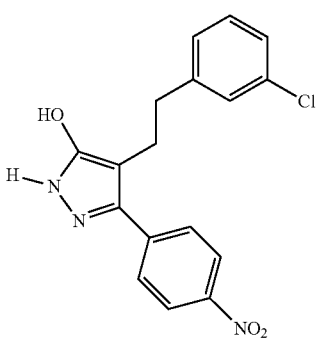
JZ-1-96-2-2
JZ-1-131
C₁₇H₁₄ClN₃O₃
Exact Mass: 343.0724

-continued
JV-1-75-1
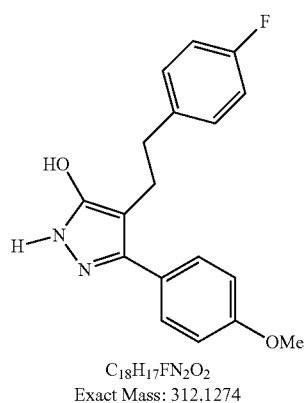
C₁₈H₁₇FN₂O₂
Exact Mass: 312.1274
JV-1-59-1
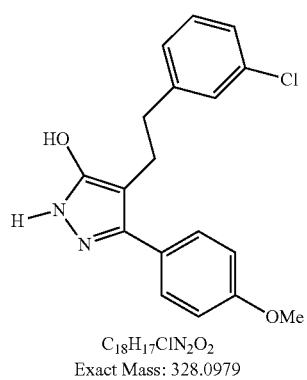
C₁₈H₁₇ClN₂O₂
Exact Mass: 328.0979
JV-1-75-2A
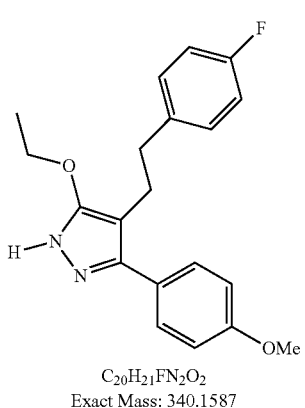
C₂₀H₂₁FN₂O₂
Exact Mass: 340.1587
JZ-1-97-2-1
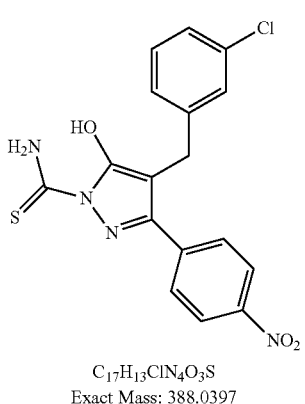
C₁₇H₁₃ClN₄O₃S
Exact Mass: 388.0397
-continued
JV-2-10
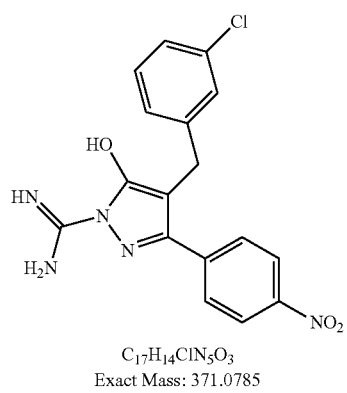
C₁₇H₁₄ClN₅O₃
Exact Mass: 371.0785
JV-2-12
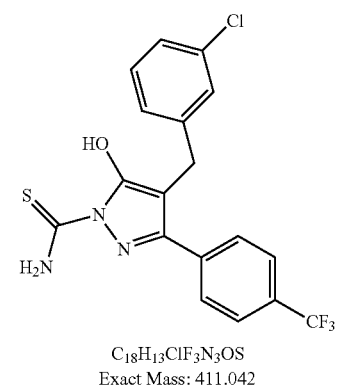
C₁₈H₁₃ClF₃N₃OS
Exact Mass: 411.042
DD-1-34
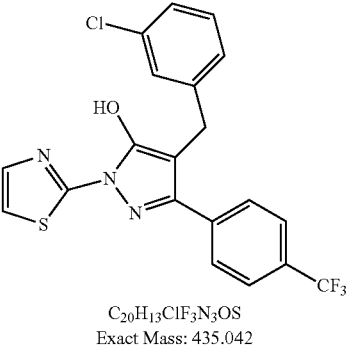
C₂₀H₁₃ClF₃N₃OS
Exact Mass: 435.042
DD-1-33
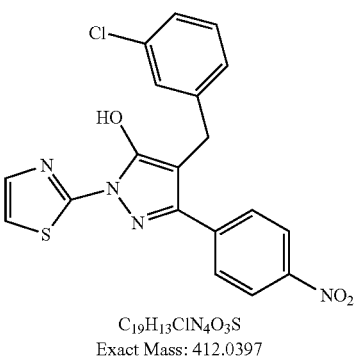
C₁₉H₁₃ClN₄O₃S
Exact Mass: 412.0397

-continued
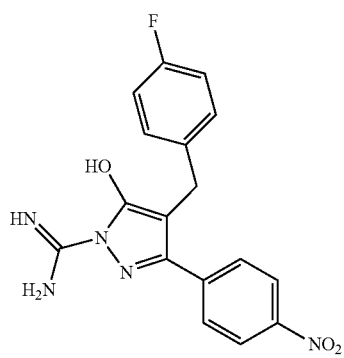
JV-2-8
C$_{17}$H$_{14}$FN$_5$O$_3$
Exact Mass: 355.1081
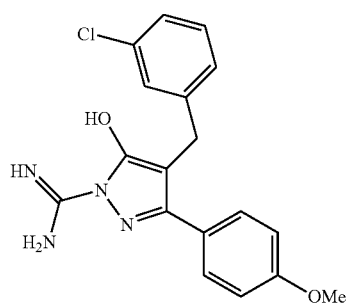
DD-1-27
C$_{18}$H$_{17}$ClN$_4$O$_2$
Exact Mass: 356.104
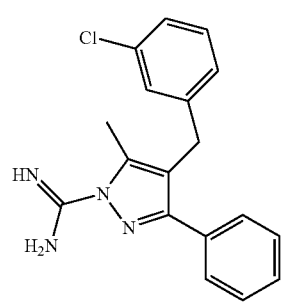
DD-1-26
C$_{18}$H$_{17}$ClN$_4$
Exact Mass: 324.1142
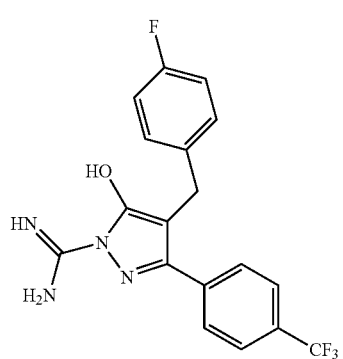
JZ-1-177
C$_{18}$H$_{14}$F$_4$N$_4$O
Exact Mass: 378.1104
-continued
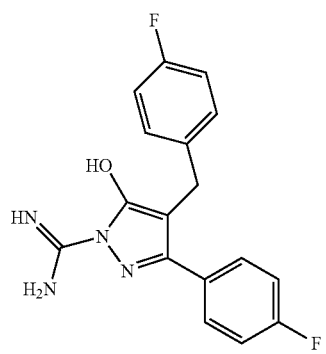
JZ-1-175
C$_{17}$H$_{14}$F$_2$N$_4$O
Exact Mass: 328.1136
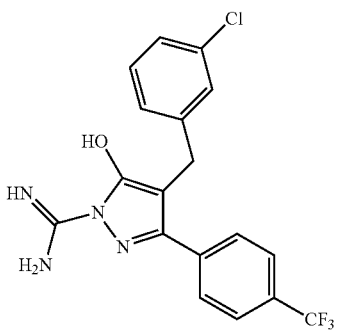
JV-2-9-1
C$_{18}$H$_{14}$ClF$_3$N$_4$O
Exact Mass: 394.0808
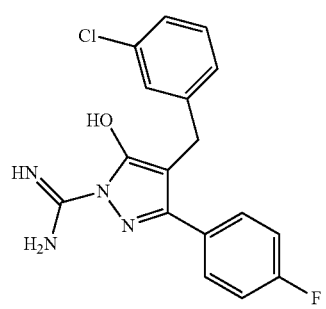
DD-1-21
C$_{17}$H$_{14}$ClFN$_4$O
Exact Mass: 344.084
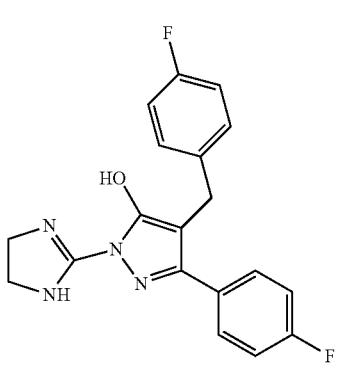
Jz-1-176
C$_{19}$H$_{16}$F$_2$N$_4$O
Exact Mass: 354.1292

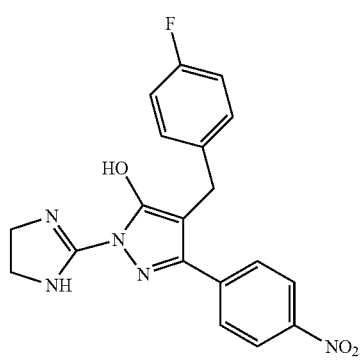
JZ-1-171
C₁₉H₁₆FN₅O₃
Exact Mass: 381.1237
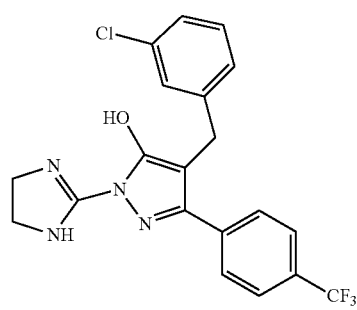
JV-2-14
C₂₀H₁₆ClF₃N₄O
Exact Mass: 420.0965
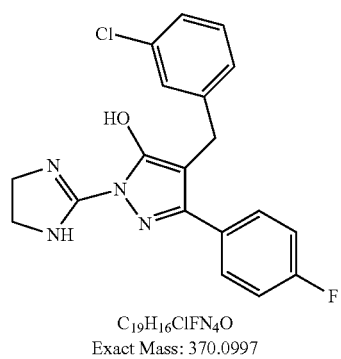
DD-1-22
C₁₉H₁₆ClFN₄O
Exact Mass: 370.0997
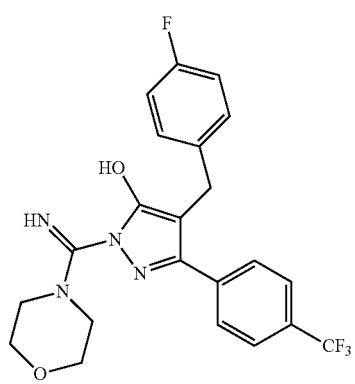
JZ-1-180
C₂₂H₂₀F₄N₄O₂
Exact Mass: 448.1522
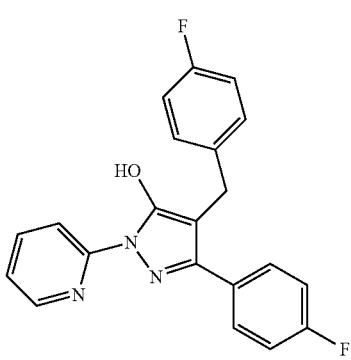
JZ-1-178
C₂₁H₁₅F₂N₃O
Exact Mass: 363.1183
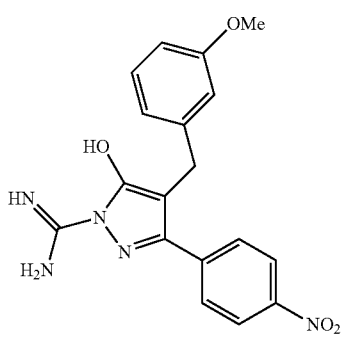
EAF-1-21
C₁₈H₁₇N₅O₄
Exact Mass: 367.1281
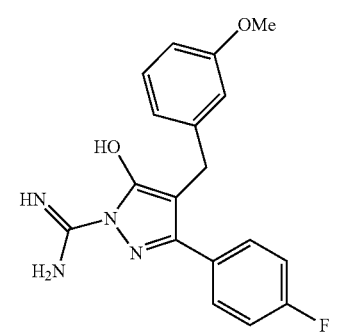
EAF-1-22
C₁₈H₁₇FN₄O₂
Exact Mass: 340.1336
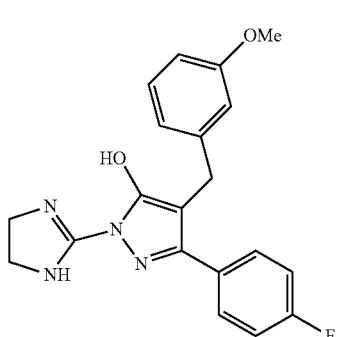
PCl-II-125
C₂₀H₁₉FN₄O₂
Exact Mass: 366.1492

-continued
PCI-II-123
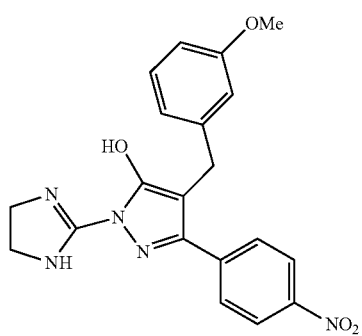
C$_{20}$H$_{19}$N$_5$O$_4$
Exact Mass: 393.1437
JV-2-16
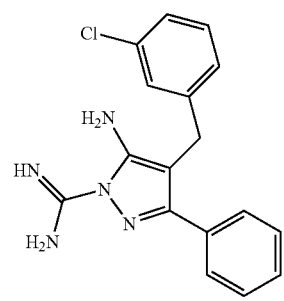
C$_{17}$H$_{16}$ClN$_5$
Exact Mass: 325.1094
JV-2-19
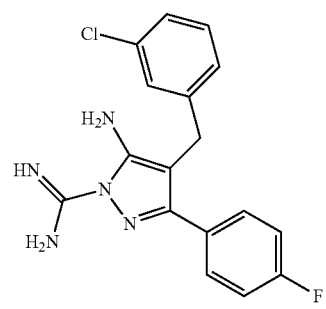
C$_{17}$H$_{15}$ClFN$_5$
Exact Mass: 343.1
DD-1-30
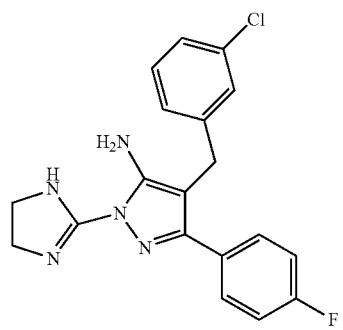
C$_{19}$H$_{17}$ClFN$_5$
Exact Mass: 369.1157
-continued
JZ-1-97-2-2
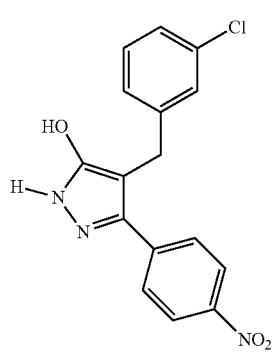
C$_{16}$H$_{12}$ClN$_3$O$_3$
Exact Mass: 329.0567
JV-2-13
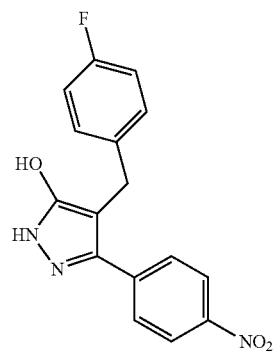
C$_{16}$H$_{12}$FN$_3$O$_3$
Exact Mass: 313.0863
JZ-1-179-2
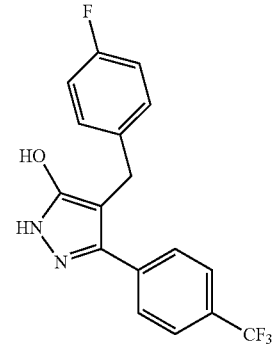
C$_{17}$H$_{12}$F$_4$N$_2$O
Exact Mass: 336.0886
JV-1-62-2-2
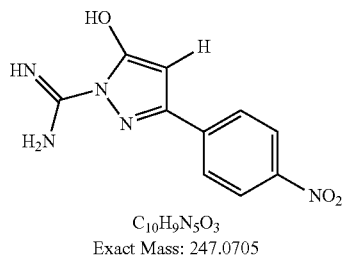
C$_{10}$H$_9$N$_5$O$_3$
Exact Mass: 247.0705

-continued
JZ-1-94
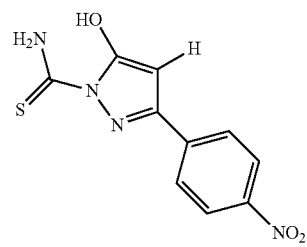
C₁₀H₈N₄O₃S
Exact Mass: 264.0317
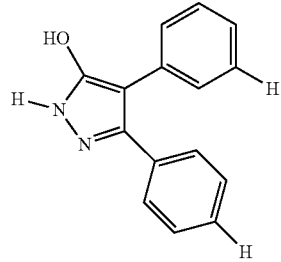
C₁₅H₁₂N₂O
Exact Mass: 236.095
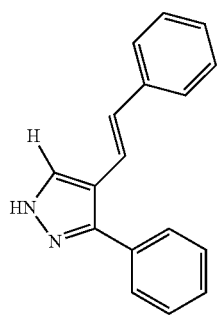
C₁₇H₁₄N₂
Exact Mass: 146.1157
JZ-1-145-1
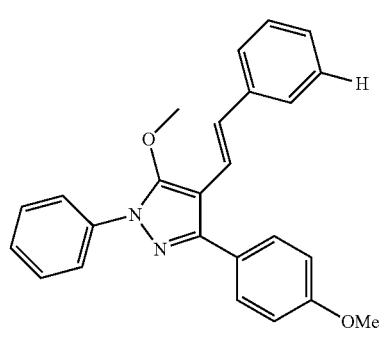
C₂₅H₂₂N₂O₂
Exact Mass: 382.1681
-continued
JZ-1-146-1
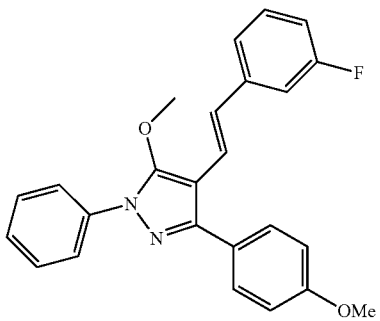
C₂₅H₂₁FN₂O₂
Exact Mass: 400.1587
JZ-1-78
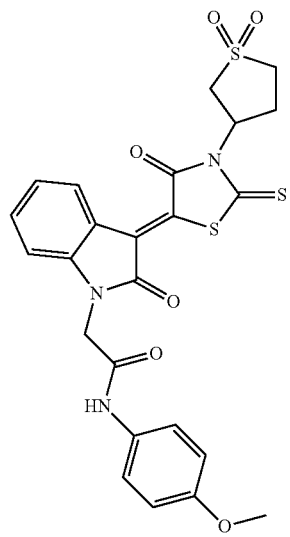
Vit-3f
C27: MW 543.6
SID: 26726147
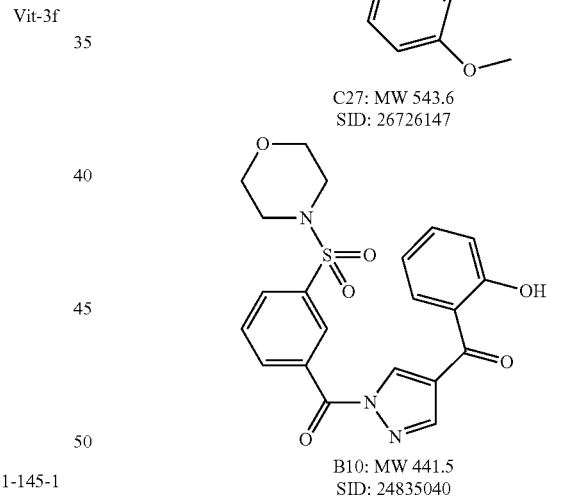
B10: MW 441.5
SID: 24835040
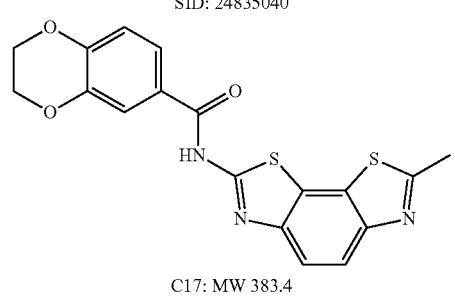
C17: MW 383.4
SID: 4252095
The compound disclosed herein also may exist as a pharmaceutically acceptable salt. In particular disclosed embodiments, the compound may be a salt derived from a variety of counter ions, both organic or inorganic, selected from, but not limited to ammonium, calcium, magnesium, potassium, sodium, and tetraalkylammonium. In particular disclosed embodiments, the compound may be a pharmaceutically acceptable salt selected from a hydrochloride, hydrobromide, tartrate, mesylate, acetate, and the like. The pharmaceutically acceptable salts disclosed herein may either be formed by replacing an acidic proton of the parent compound with a metal ion, or when the acidic proton of the parent compound coordinates with an organic base (e.g., an amine-containing base, such as dimethylamine, di- or tri-ethylamine, ammonia, and the like).

Certain embodiments of the compound disclosed herein exhibit sufficient aqueous solubility necessary for in vitro and/or in vivo applications. Also, embodiments of the disclosed compound exhibit pharmacologically significant early-stage metabolic profiles. Preferred compounds are those that are potent, but are suitable for administering at low dosages.

The compound disclosed herein may be administered alone or in combination with one or more other components. In particular disclosed embodiments, the compound may be administered with one or more pharmacologically active agents. The disclosed compound may function additively or synergistically with the one or more pharmacologically active agents. In particular disclosed embodiments, the compound may be used in combination with one or more of these pharmacologically active agents in order to lower the effective dose needed for treatment. The ability to reduce effective doses of the pharmacologically active agent may aid in reducing drug resistance and/or cumulative toxicity. In particular disclosed embodiments, the compound and the pharmacologically active agent are administered sequentially. In other disclosed embodiments, the compound and the pharmacologically active agent may be administered simultaneously in the same or separate mode of administration.

Examples of the pharmacologically active agent include, but are not limited to, antiretroviral agents. In particular disclosed embodiments, the antiretroviral agent is selected from an entry inhibitor, a CCR5 receptor antagonist, a nucleoside reverse transcriptase inhibitor, a non-nucleoside reverse transcriptase inhibitor, a protease inhibitor, an integrase inhibitor, a maturation inhibitor, or combinations thereof. Exemplary antiretroviral agents include, but are not limited to, maraviroc, enfuvirtide, aplaviroc, vicriviroc, zidovudine, didanosine, zalcitabine, stavudine, lamivudine, abacavir, emtricitabine, entecavir, apricitabine, tenofovir, adefovir, efavirenz, nevirapine, delavirdine, etravirine, rilpivirine, saquinavir, ritonavir, indinavir, nelfinavir, amprenavir, lopinavir atazanavir fosamprenavir tipranavir darunavir, MK-2048, elvitegravir, bevirimat, MPC-9055, or combinations thereof.

The compound may also be administered with one or more conventional non-toxic pharmaceutically acceptable carriers, and excipients appropriate for each route of administration. Non-limiting examples of pharmaceutically acceptable carriers include sterile solutions, tablets, capsules, buffers, saline, and the like. Non-limiting examples of excipients include anti-adherents (e.g., magnesium stearate), binders (e.g., saccharides, such as sucrose, lactose, starches, cellulose, xylitol, sorbitol, and maltitol; gelatin; and synthetic polymers), coatings (e.g., hydroxypropyl methylcellulose, gelatin, and the like), disintegrants (e.g., potato starch, sodium starch glycolate, and the like), fillers (e.g., lactose, sucrose, glucose mannitol, sorbitol, calcium carbonate, and magnesium stearate), flavors (e.g., mint, cherry, anise, vanilla, and the like), colors (e.g., any color that improves the appearance of a formulation of the compound), lubricants (talc, silica, fat, stearic acid, and the like), glidants (e.g., magnesium carbonate, talc, and the like), sorbents (e.g., fatty acids, waxes, plastics, and plant fibers), preservatives (e.g., antioxidants, cysteine, methionine, citric acid, and the like), sweeteners (e.g., corn syrup, sugar, and the like), or combinations thereof.

In particular disclosed embodiments, the compound may be administered using methods known to those of ordinary skill in the art as being suitable for exposing a patient to sufficient dosages of the disclosed compound. Certain modes of administration are contemplated by the present disclosure, including, but not limited to oral (e.g., capsule, tablet, lozenge, syrup, or powder); intramuscular, intraperitoneal, intravenous, intracisternal injection or infusion (e.g., sterile suspensions, solutions, or emulsions); subcutaneous injection (e.g., sterile suspensions, solutions, or emulsions); implant; nasal inhalation (e.g., aerosol spray administered via inhaler, liquid nebulizer, sprayer, or thermal vaporizer); vaginal (e.g., solution, suppository, or ointment); rectal (e.g., solution, suppository, or ointment); or topically (e.g., gel, ointment, cream, aerosol, etc.).

In particular disclosed embodiments, the compound is administered to a patient medically diagnosed with HIV or exhibiting symptoms associated with HIV. The patient may be identified using any method known to those of ordinary skill in the art, such as rapid or standard enzyme immunoassay screening, a confirmatory test, such as a Western blot, or an HIV antigen/antibody test. In other disclosed embodiments, the patient may be selected based on physical symptoms, such fever, fatigue, rash, headache, swollen lymph nodes, and sore throat. The compound may also be administered to a patient prophylactically or post-exposure prophylactically. Solely by way of example, the patient may be administered the compound after occupational exposure, non-occupational exposure, or if the patient anticipates exposure.

III. Method of Making the HIV-Nef Function Antagonist

Disclosed herein are embodiments of a method for making the disclosed HIV-Nef function antagonist.

Embodiments of a compound having a general Formula 1 may be synthesized using any of the following synthetic procedures. Particular embodiments of the compound may be made using the following synthetic reaction scheme.

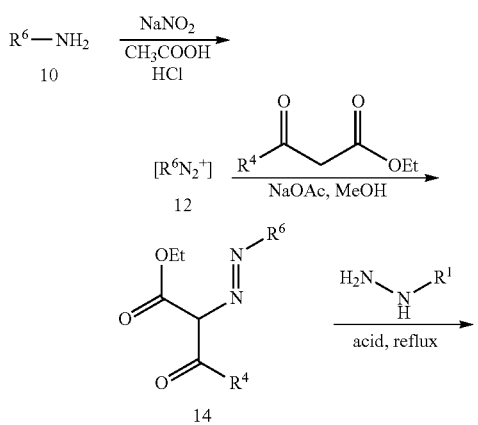

-continued

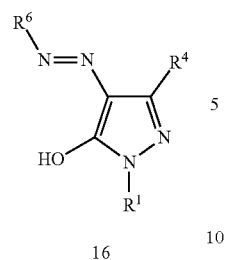
16

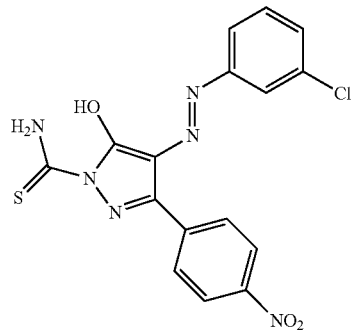
B-9

According to Scheme 1, a functionalized amine compound 10 is converted to the diazo compound 12, which may then be reacted with a β-keto ester compound to give the α-substituted azo compound 14. α-Substituted azo compound 6 was then converted to pyrazole compound 16. An exemplary embodiment is provided below in Scheme 2, and exemplary compounds made using this method also being provided below. With reference to Scheme 2, $R^{10}$ may be selected from halogen, alkoxy, cyano, nitro, hydroxyl, thiol, or thioether; and $R^{11}$ may be selected from halogen, alkoxy, cyano, nitro, hydroxyl, thiol, thioether, or trifluoromethyl.

Scheme 2

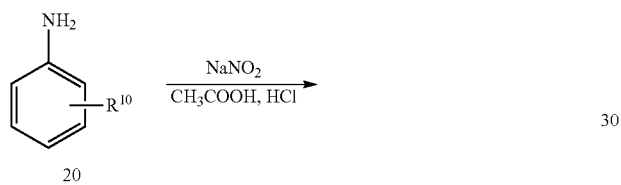
20

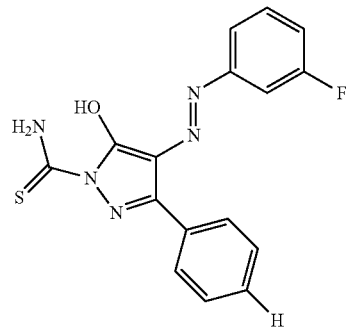
PCI-I-30

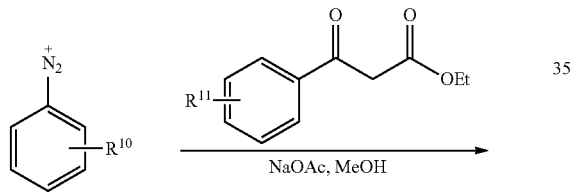
22

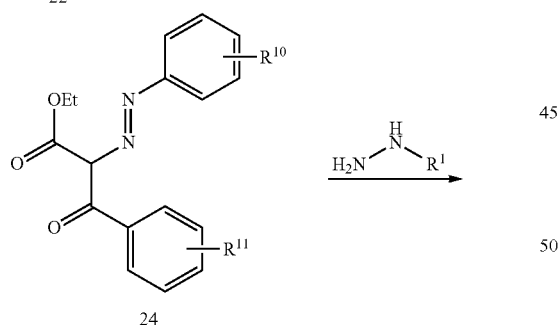
24

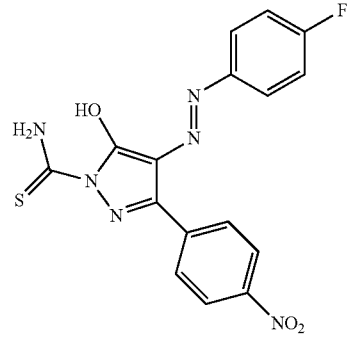
PCI-I-23

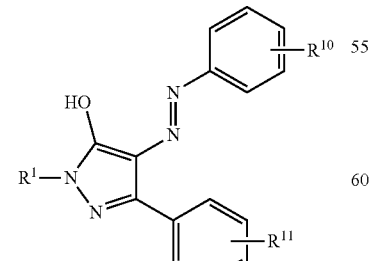
26

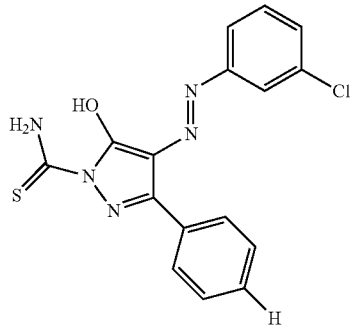
PCI-I-29

-continued
KM-I-42
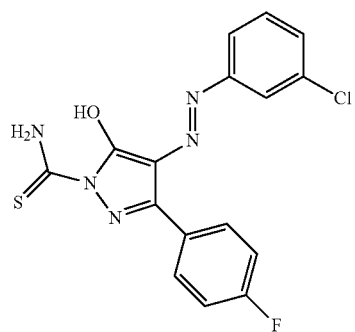
PCl-I-06
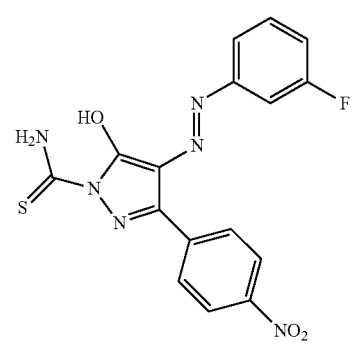
KM-1-46
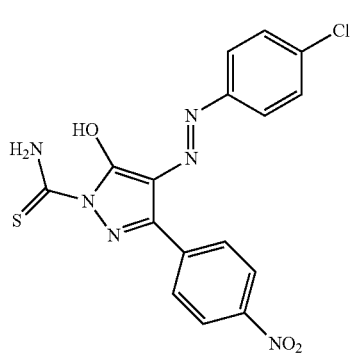
KM-1-48
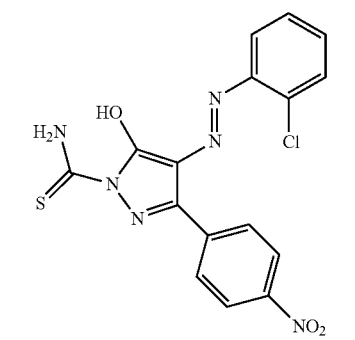
-continued
PCl-1-25
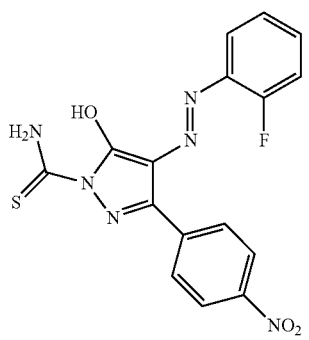
PCl-1-55
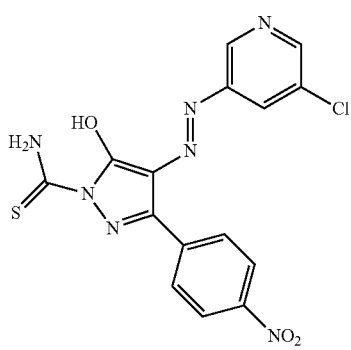
PCl-1-50
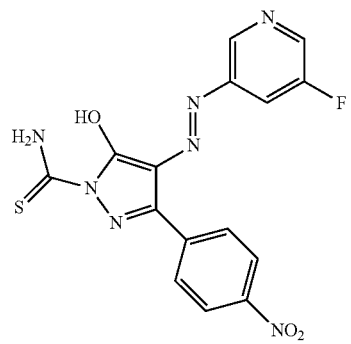
PCl-1-52
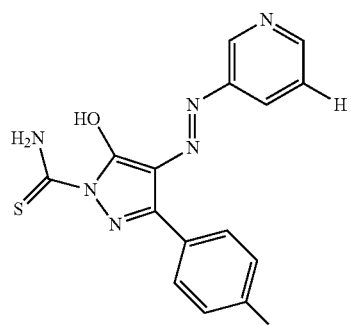

JZ-1-49
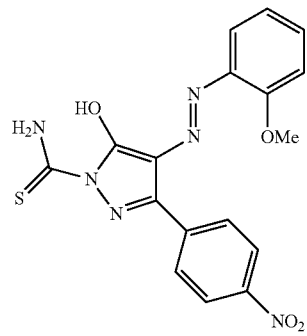
JZ-1-62
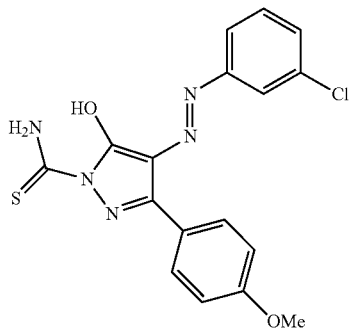
JZ-1-56
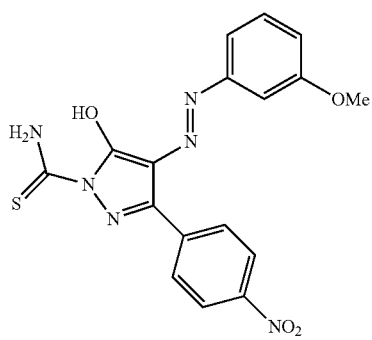
JZ-1-64
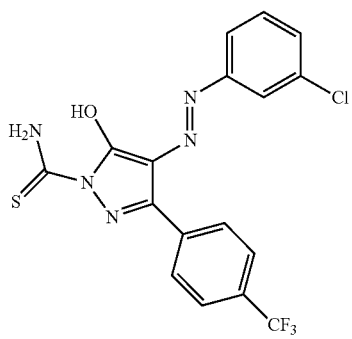
JZ-1-107
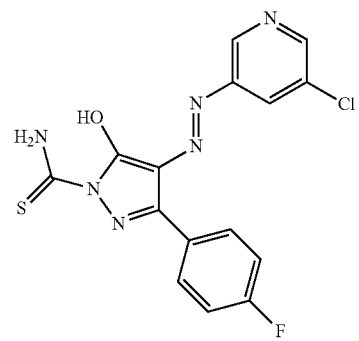
JZ-1-101
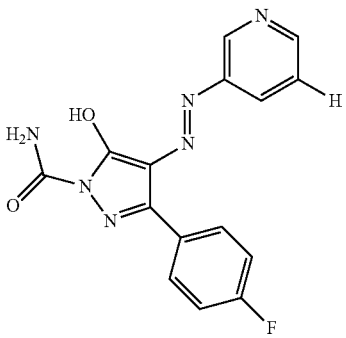
JZ-1-58-3
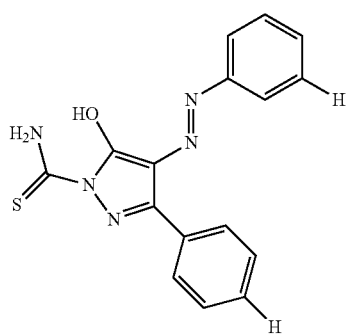
JZ-1-106
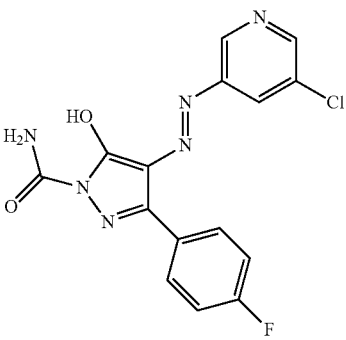

PCl-1-43
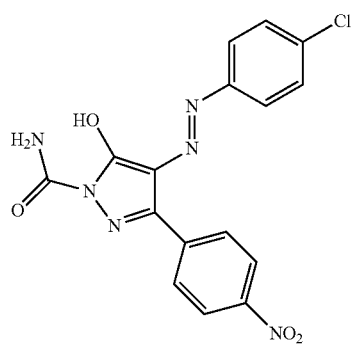
PCl-1-45
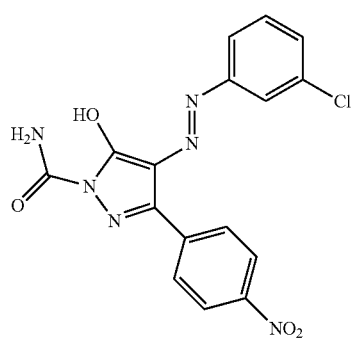
PCl-1-48
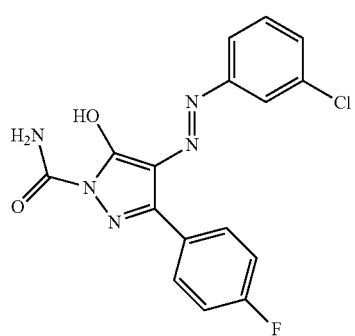
PCl-1-53
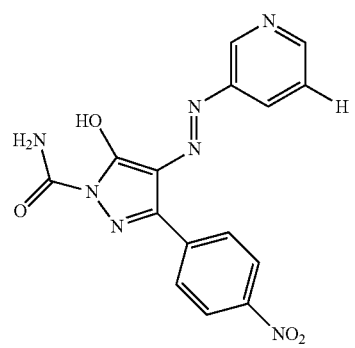
PCl-1-56
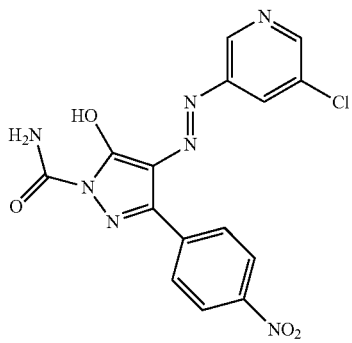
JV-2-2
JV-2-21
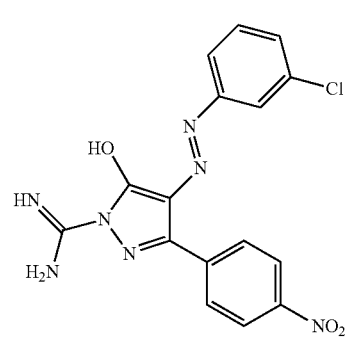
JZ-1-50
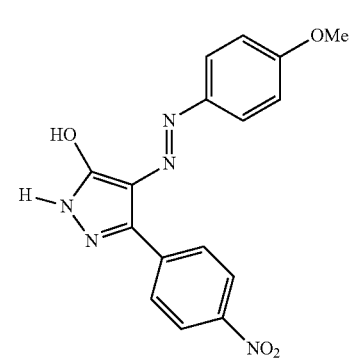
JZ-1-110-1
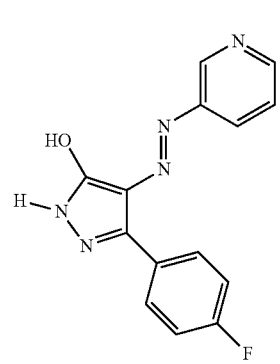

JZ-1-110-2

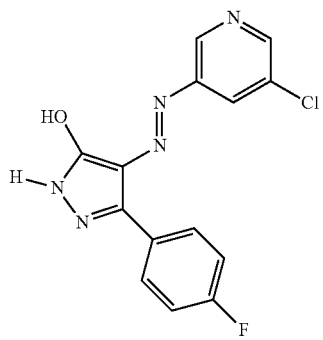

JZ-1-58-2

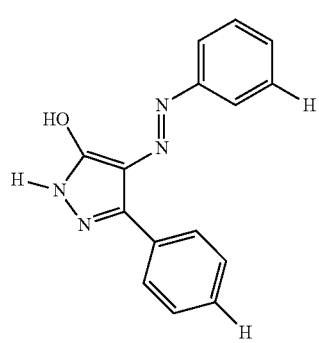

Embodiments of a compound having a Formula 4 may also be synthesized using the reaction conditions illustrated in Scheme 3.

Scheme 3

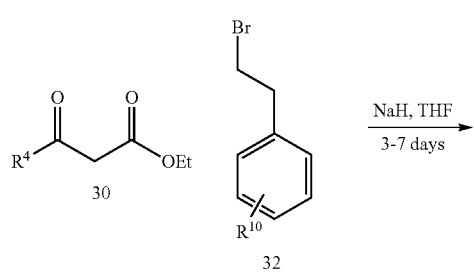

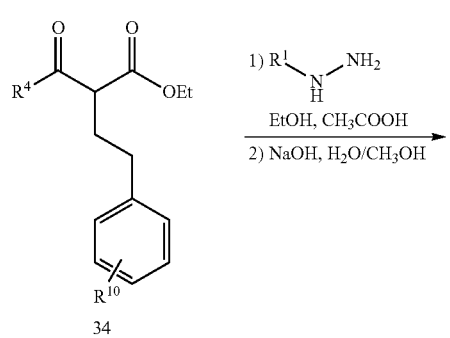

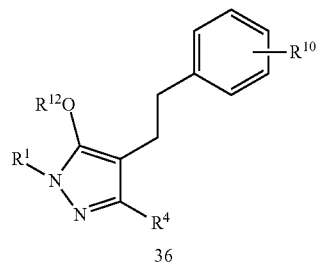

36

According to Scheme 3, β-keto ester compound 30 is reacted with aryl compound 32 in the presence of sodium hydride in order to make the α-substituted compound 34. This compound is then reacted with a hydrazine derivative followed by sodium hydroxide to make pyrazole compound 36. With reference to Scheme 3, $R^{10}$ may be selected from halogen, alkoxy, cyano, nitro, hydroxyl, thiol, or, thioether; and $R^{12}$ may be selected from hydrogen, methyl, ethyl, propyl, butyl, and the like. Exemplary compounds made using the method provided in Scheme 3 are provided below.

JZ-1-96-2-1

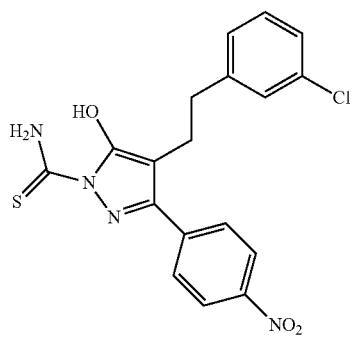

JV-1-62-2-1

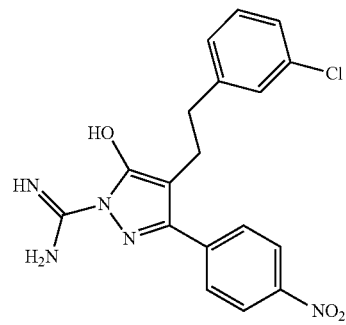

JV-1-94
JZ-1-198

JZ-1-135-1
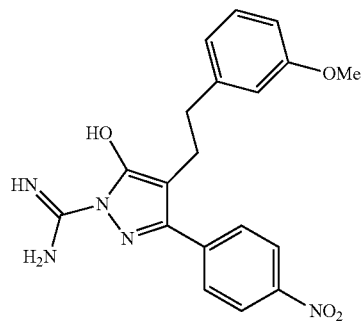
JV-1-62-1
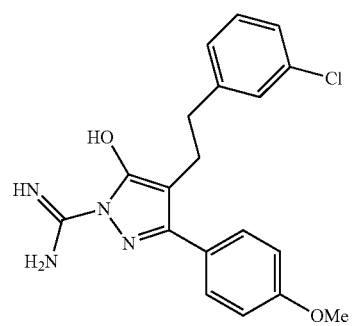
JV-1-67-1
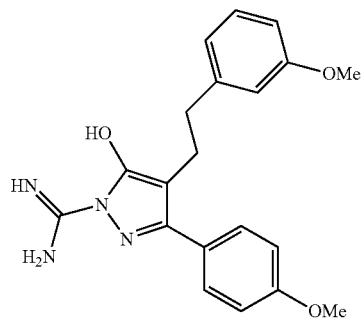
JV-1-74-1
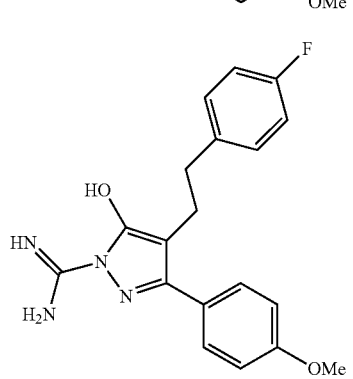
JZ-1-135-2
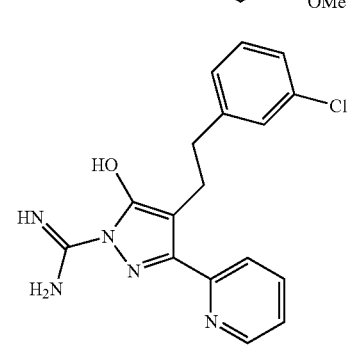
JV-1-89
JZ-1-197
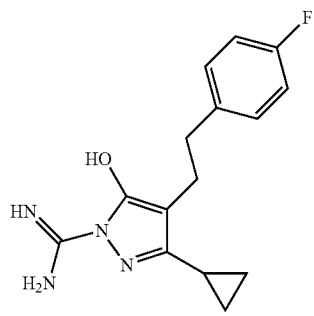
JV-1-87
JZ-1-207
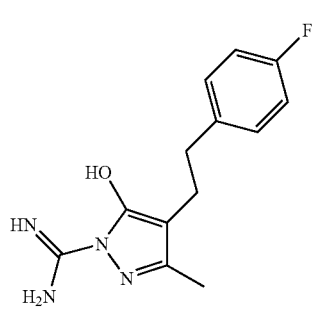
JV-1-96
JZ-1-208
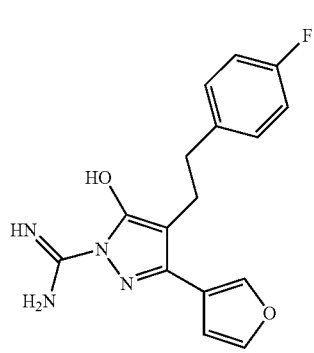
JZ-1-154-2-2
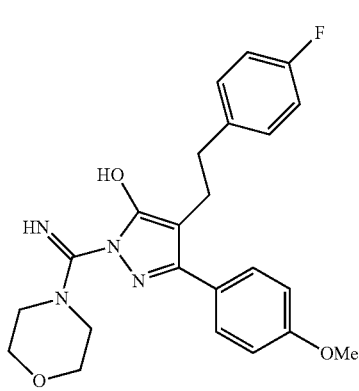

JV-1-74-2
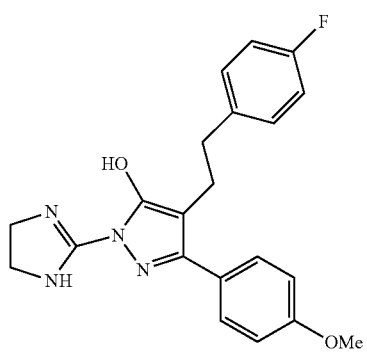
JV-2-3
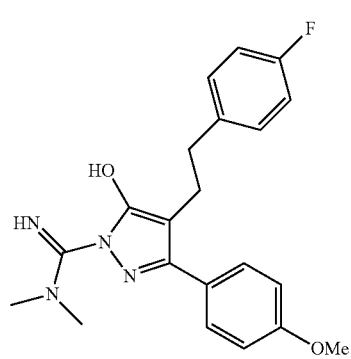
JV-1-71-1
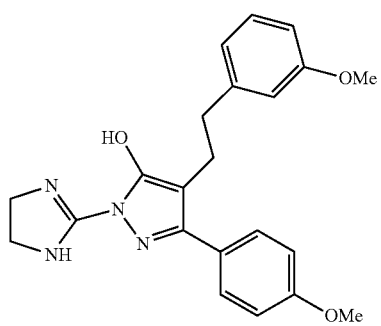
JV-1-79
JZ-1-203
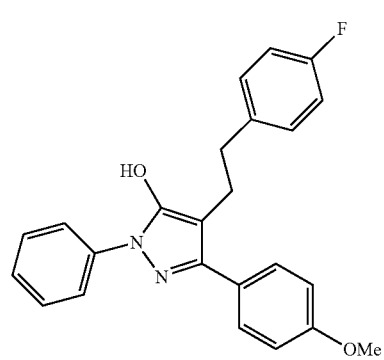
JV-1-80
JZ-1-195
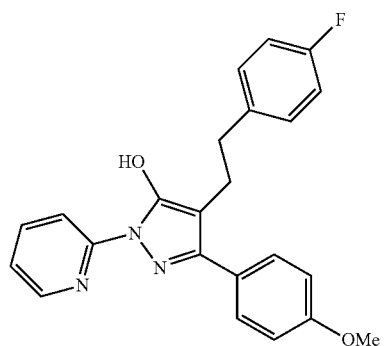
JV-1-97
JZ-1-206
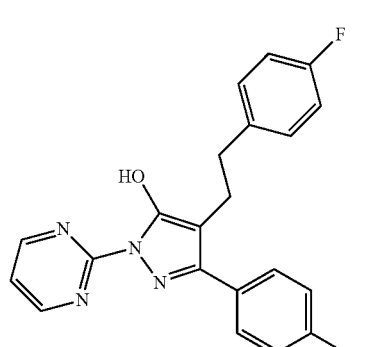
JV-1-96-2-2
JZ-1-131
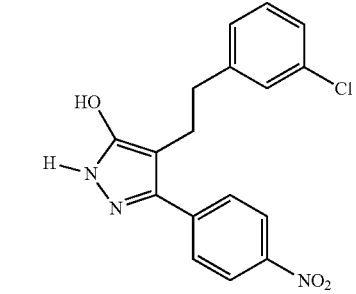
JV-1-75-1
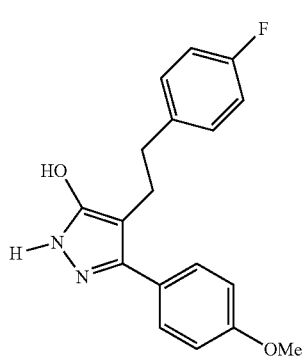

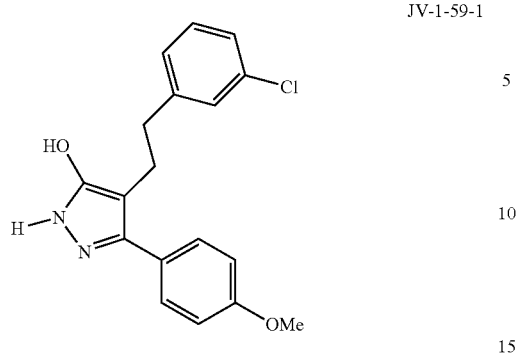
JV-1-59-1

Other embodiments of the disclosed compound may be made using the method illustrated in Scheme 4, with particular embodiments illustrated below. With reference to Scheme 4, $R^{10}$ may be selected from halogen, alkoxy, cyano, nitro, hydroxyl, thiol, or, thioether; and $R^{11}$ may be selected from halogen, alkoxy, cyano, nitro, hydroxyl, thiol, thioether, or trifluoromethyl.

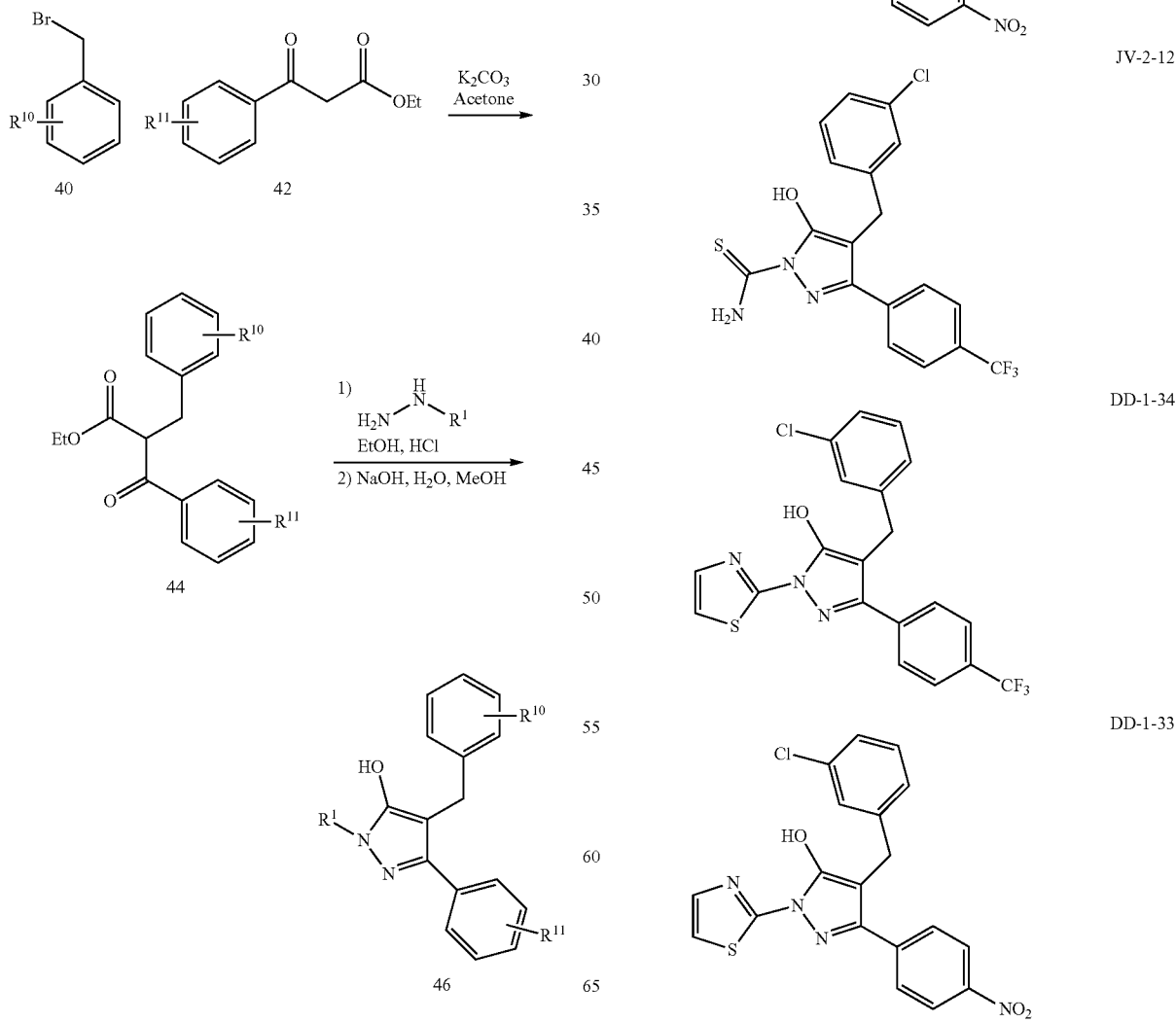

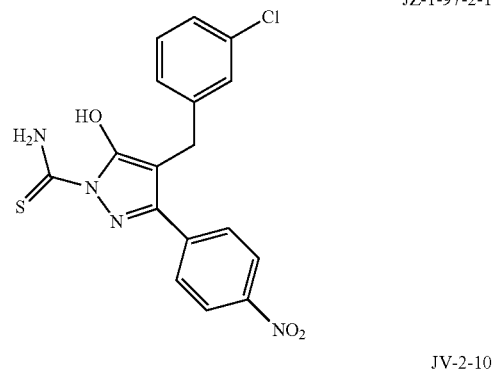
JZ-1-97-2-1

JV-2-10

JV-2-12

DD-1-34

DD-1-33

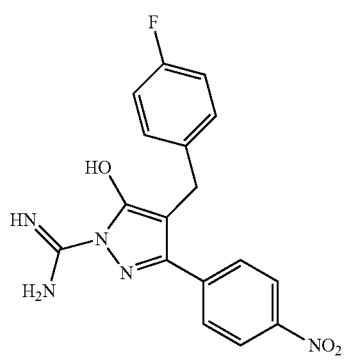
JV-2-8
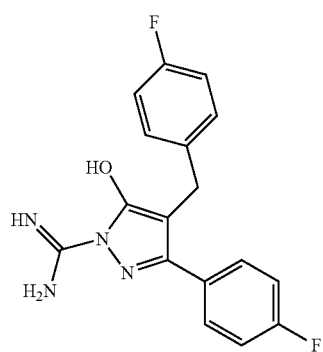
JZ-1-175
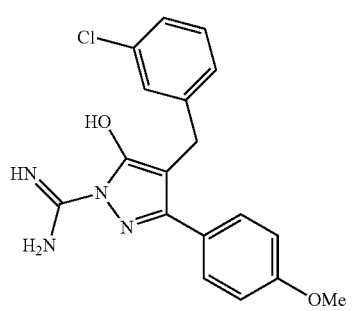
DD-1-27
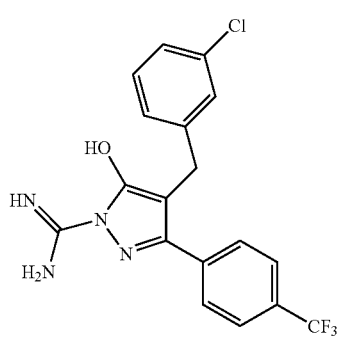
JV-2-9-1
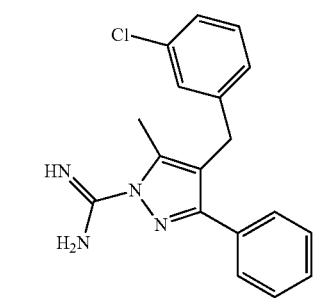
DD-1-26
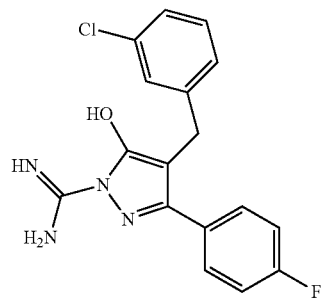
DD-1-21
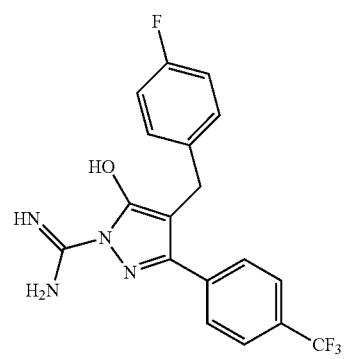
JZ-1-177
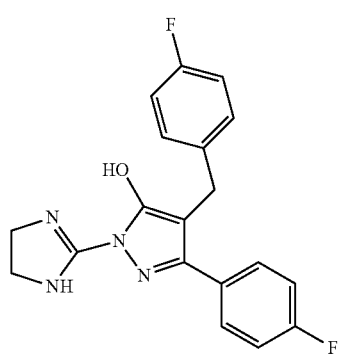
Jz-1-176

JZ-1-171
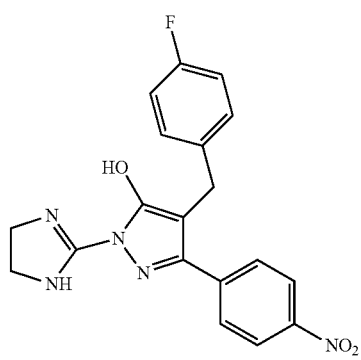
JV-2-14
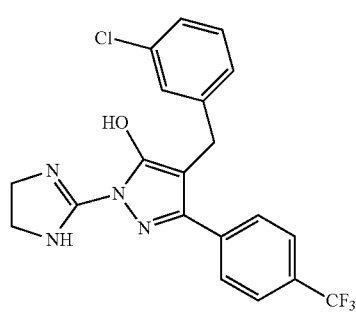
DD-1-22
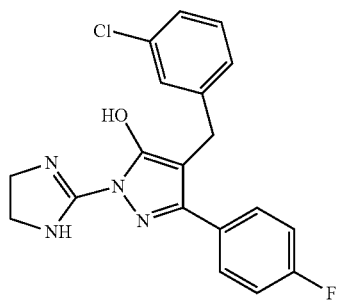
JZ-1-180
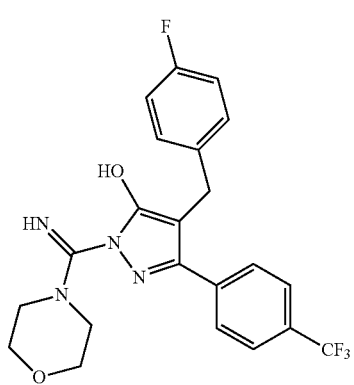
JZ-1-178
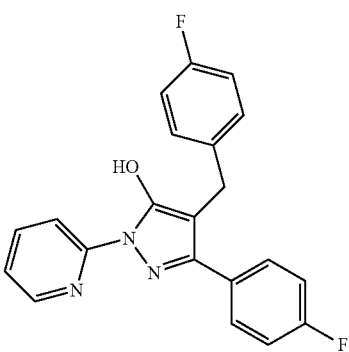
EAF-1-21
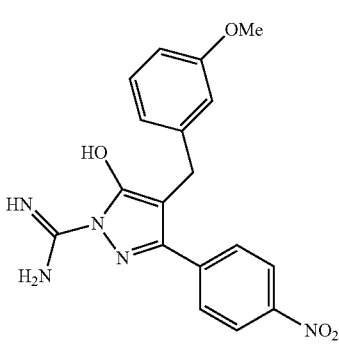
EAF-1-22
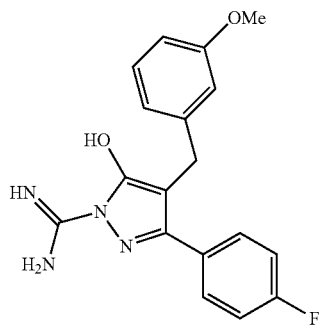
PCl-II-125
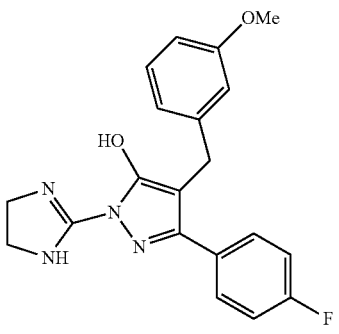

61

-continued

PCl-II-123

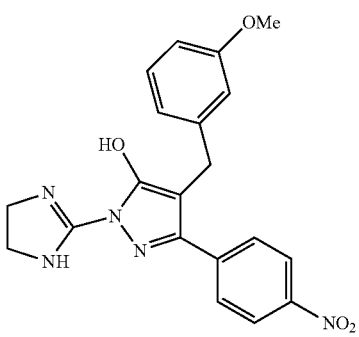

JZ-1-97-2-2

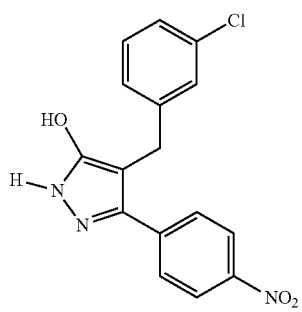

JV-2-13

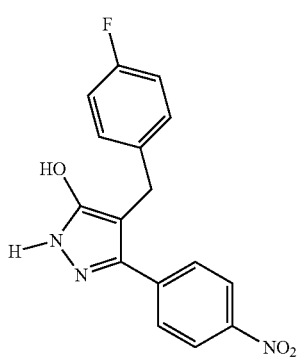

JZ-1-179-2

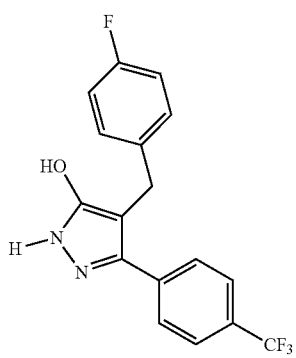

Exemplary embodiments of the compound may be made according to the synthetic methods illustrated in Scheme 5.

62

Scheme 5

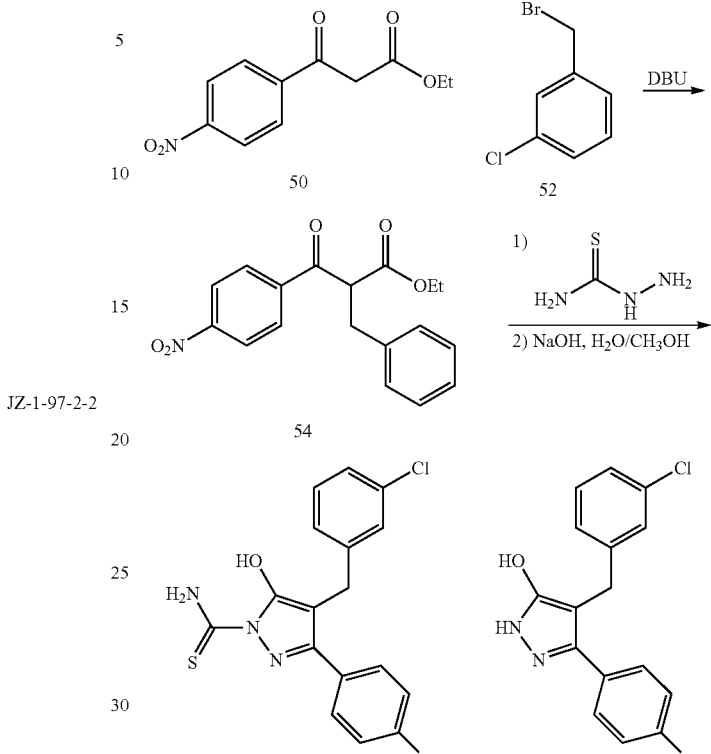

According to Scheme 5, β-keto ester compound 50 is reacted with bromo benzene compound 52 to make compound 54. Compound 54 is then converted to two working embodiments using the conditions illustrated in Scheme 5. This one-pot reaction results in the conversion of compound 54 to the N-thioamide analog as well as the free pyrazole.

Yet other embodiments of the compound may be made using the scheme illustrated below.

Scheme 6

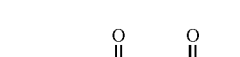

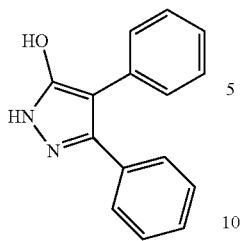

Additional embodiments may be made using the reaction protocol illustrated in Scheme 7, below.

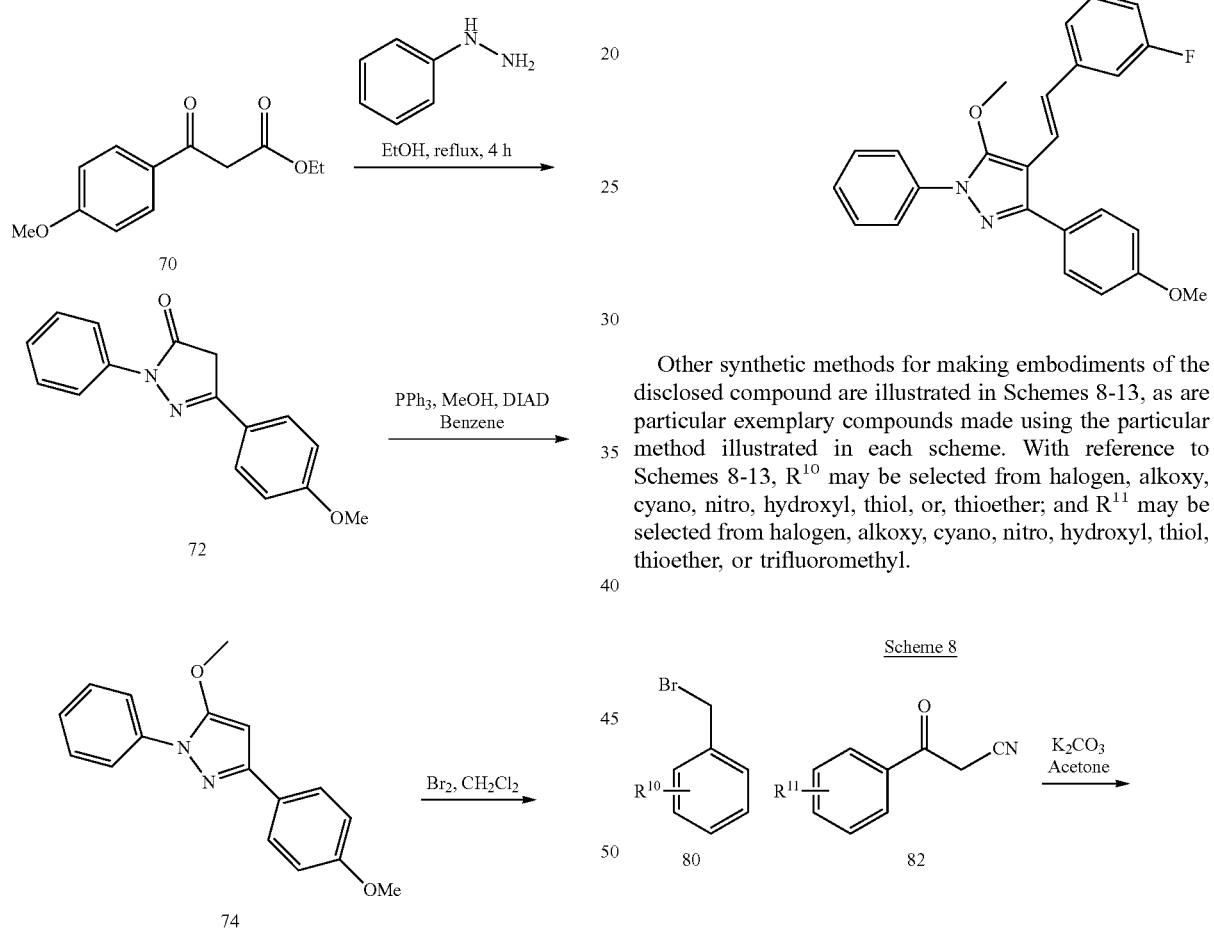

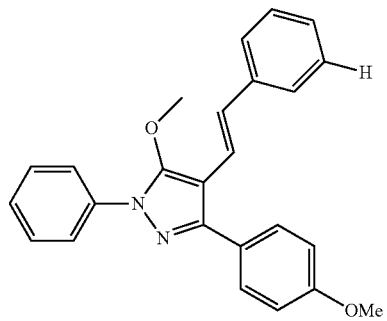 [SMILES: COc1ccc(-c2nn(-c3ccccc3)c(OC)c2/C=C/c2cccc(F)c2)cc1]

Other synthetic methods for making embodiments of the disclosed compound are illustrated in Schemes 8-13, as are particular exemplary compounds made using the particular method illustrated in each scheme. With reference to Schemes 8-13, $R^{10}$ may be selected from halogen, alkoxy, cyano, nitro, hydroxyl, thiol, or, thioether; and $R^{11}$ may be selected from halogen, alkoxy, cyano, nitro, hydroxyl, thiol, thioether, or trifluoromethyl.

Scheme 8

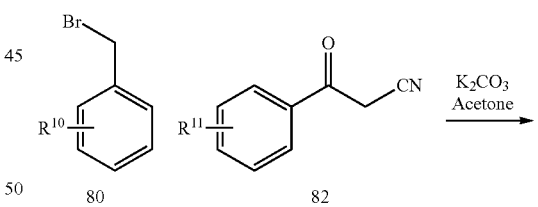

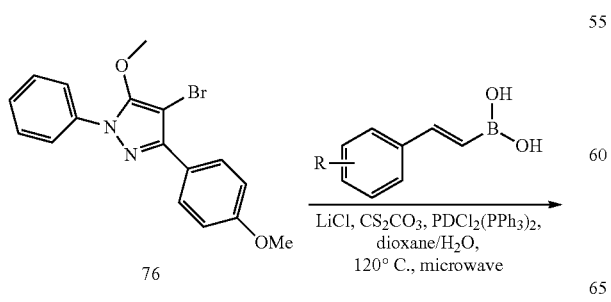

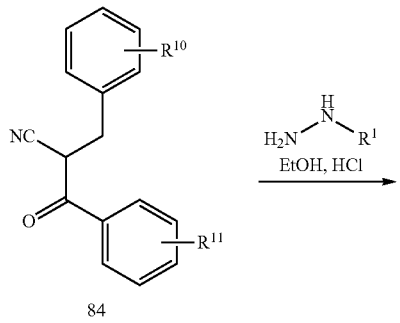

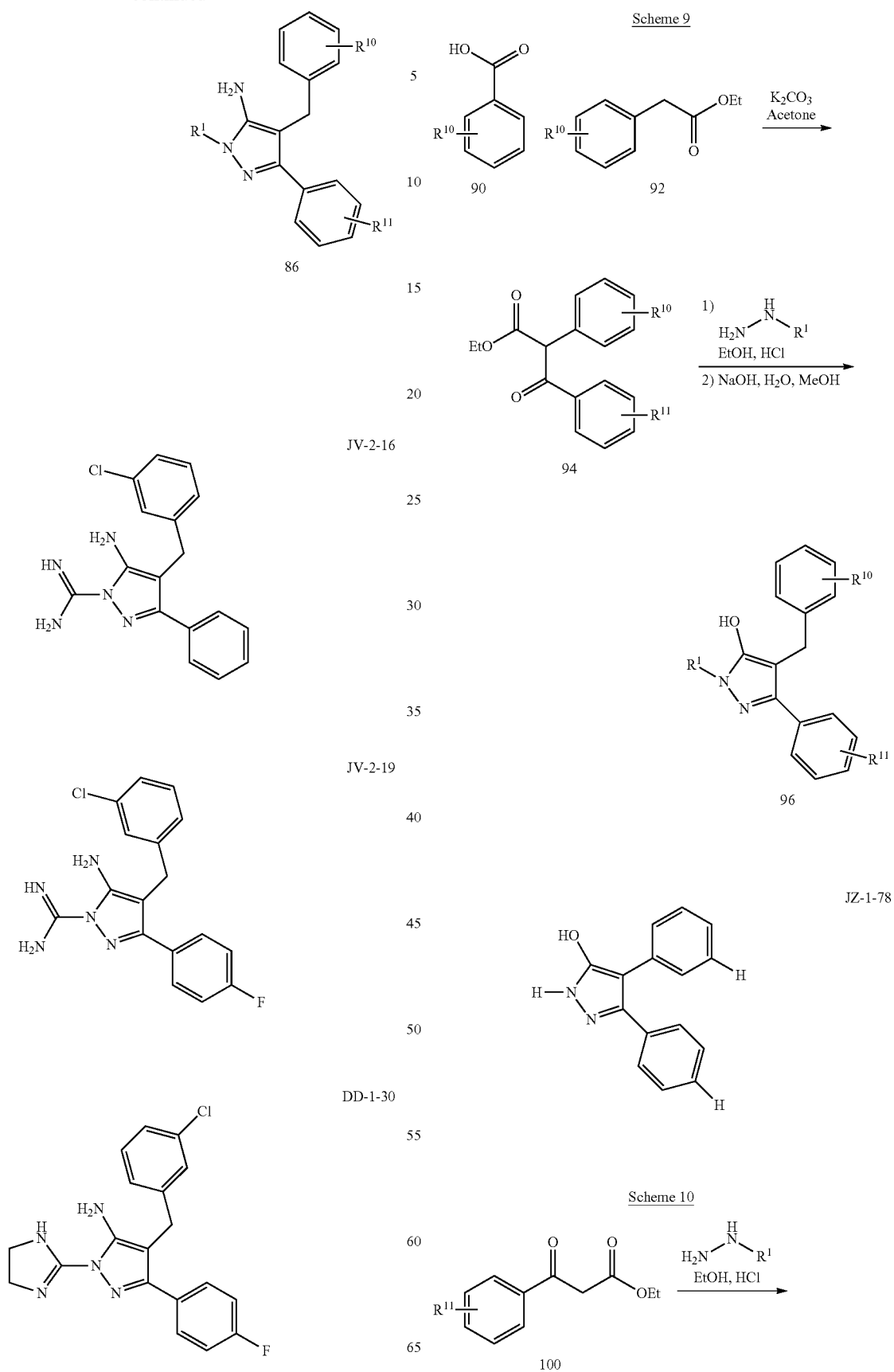

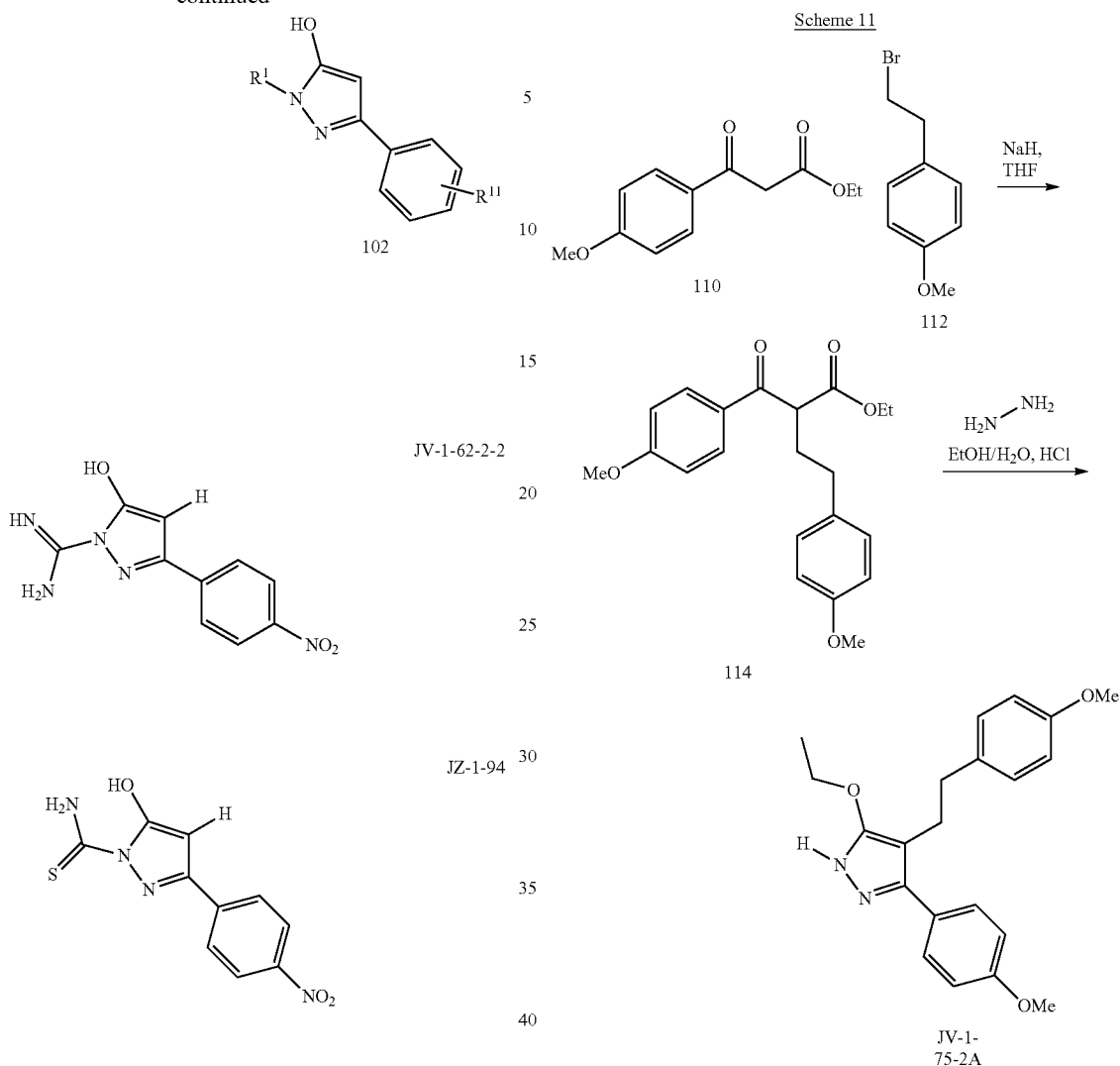
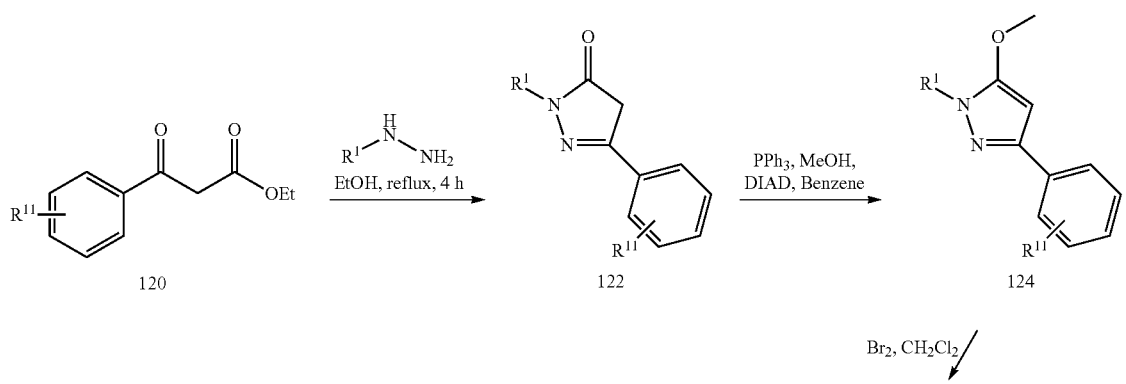

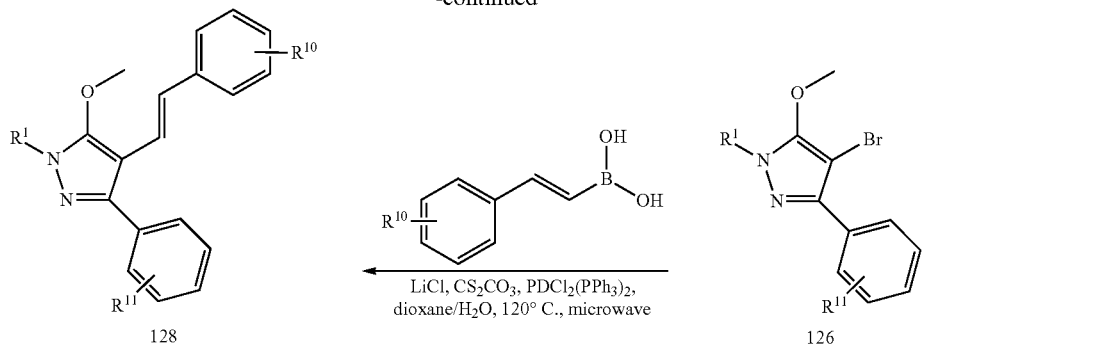
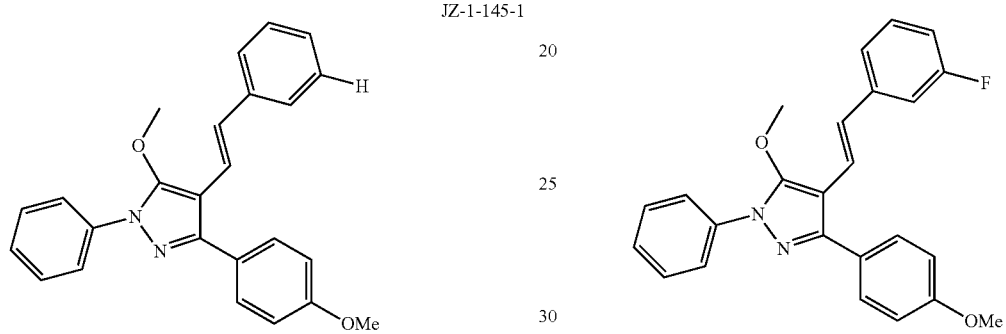
| | | |
|---|---|---|
| JZ-1-145-1 | | JZ-1-146-1 |
Scheme 13
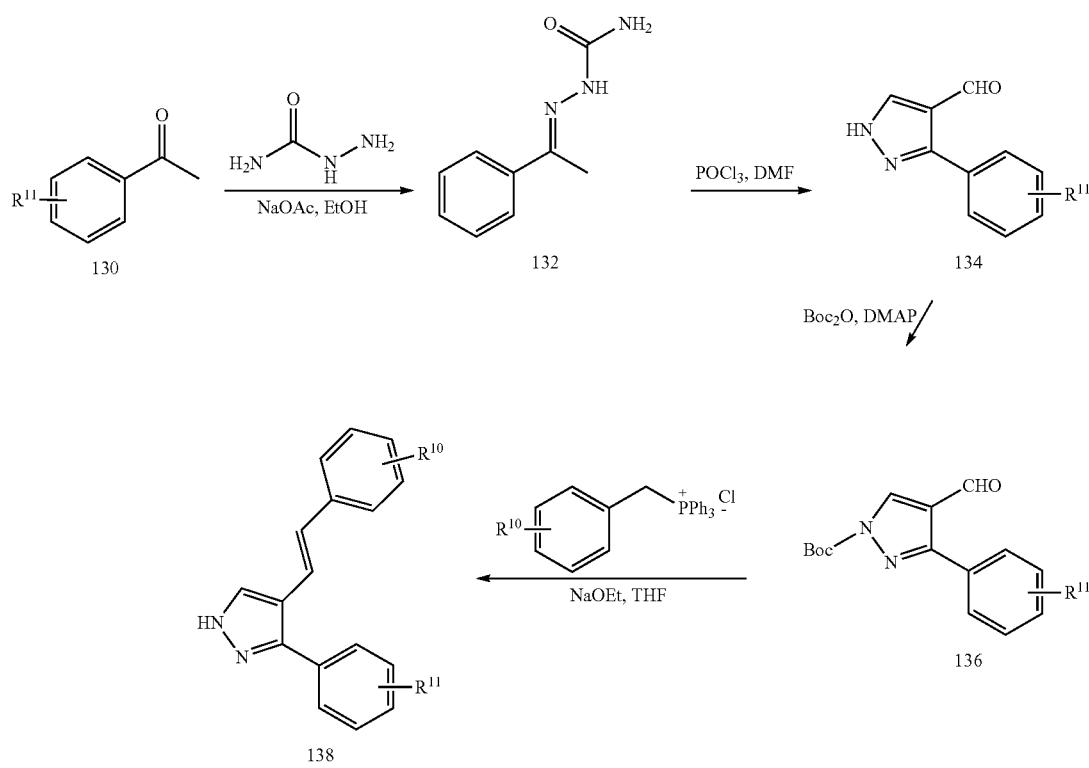

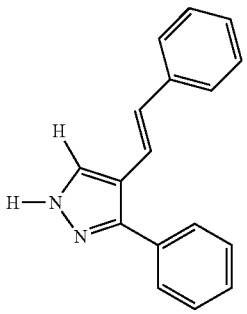

Vit-3F

In particular disclosed embodiments, the product obtained from any one of the above described reactions may be further manipulated to produce a derivative of the compound. An exemplary conversion to a derivative compound is illustrated below in Scheme 14. With reference to Scheme 14, $R^{10}$ may be selected from halogen, alkoxy, cyano, nitro, hydroxyl, thiol, or, thioether; and $R^{11}$ may be selected from halogen, alkoxy, cyano, nitro, hydroxyl, thiol, thioether, or trifluoromethyl.

Scheme 14

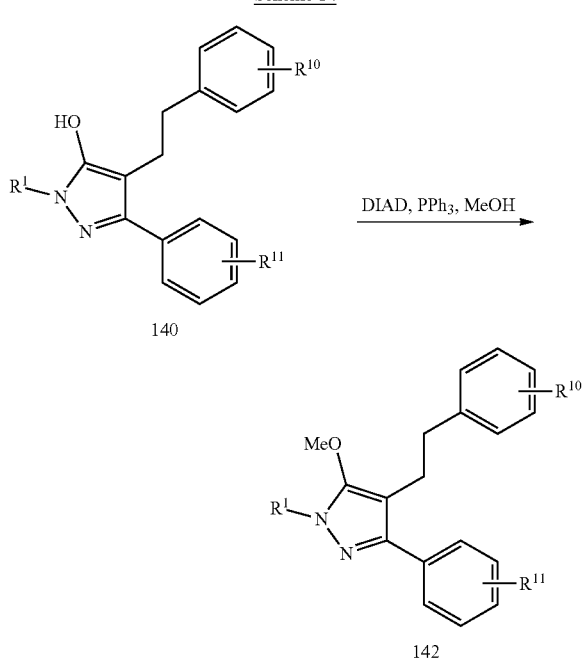

Scheme 15

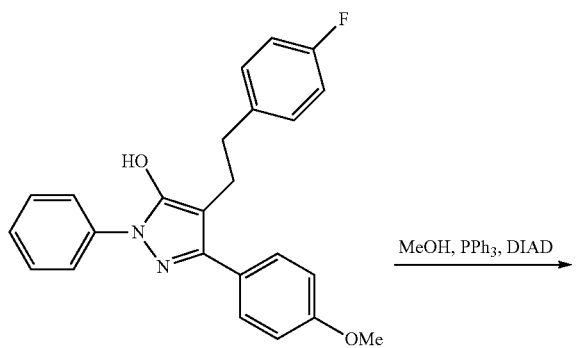

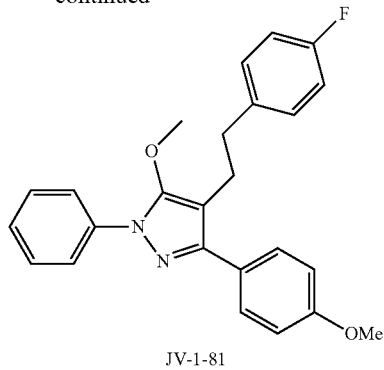

JV-1-81

IV. Method of Using the HIV-Nef Function Antagonist

The present disclosure also concerns embodiments of a method of using the disclosed compound. In particular disclosed embodiments, the method concerns inhibiting a biological function of Nef, the method comprising contacting Nef with an effective amount of a compound as disclosed herein. In particular disclosed embodiments, the method may concern using a compound having any one of Formulas 1-7, which are disclosed herein, and further may concern using one or more of (E)-4-((3-chlorophenyl)diazenyl)-5-hydroxy-3-(4-nitrophenyl)-1H-pyrazole-1-carbothioamide, 2-{(3Z)-3-[3-(1,1-dioxidotetrahydrothiophen-3-yl)-4-oxo-2-thioxo-1,3-thiazolidin-5-ylidene]-2-oxo-2,3-dihydro-1H-indol-1-yl}-N-(4-methoxyphenyl)acetamide, N-(7-methyl [1,3]thiazolo[4,5-γ][1,3]benzothiazol-2-yl)-2,3-dihydro-1, 4-benzodioxine-6-carboxamide, (4Z)-4-[(4-chlorophenyl) hydrazinylidene]-3-(4-nitrophenyl)-5-oxopyrazole-1-carbothioamide, or [4-(2-hydroxybenzoyl)pyrazol-1-yl]-(3-morpholin-4-ylsulfonylphenyl)methanone. The biological function may be selected from HIV infectivity, HIV replication, AIDS progression, or combinations thereof.

Also disclosed is a method of inhibiting an activity of a Nef-dependent kinase comprising contacting the Nef-dependent kinase with an effective amount of a compound as disclosed herein. In particular disclosed embodiments, the Nef-dependent kinase may be a Src kinase, such as Hck.

Particular embodiments concern a method of treating a Nef-mediated disease, comprising administering to a subject an effective amount of a compound as disclosed herein, including (E)-4-((3-chlorophenyl)diazenyl)-5-hydroxy-3-(4-nitrophenyl)-1H-pyrazole-1-carbothioamide, 2-{(3Z)-3-[3-(1,1-dioxidotetrahydrothiophen-3-yl)-4-oxo-2-thioxo-1,3-thiazolidin-5-ylidene]-2-oxo-2,3-dihydro-1H-indol-1-yl}-N-(4-methoxyphenyl)acetamide, N-(7-methyl[1,3]thiazolo [4,5-γ][1,3]benzothiazol-2-yl)-2,3-dihydro-1,4-benzodioxine-6-carboxamide, (4Z)-4-[(4-chlorophenyl) hydrazinylidene]-3-(4-nitrophenyl)-5-oxopyrazole-1-carbothioamide, or [4-(2-hydroxybenzoyl)pyrazol-1-yl]-(3-morpholin-4-ylsulfonylphenyl)methanone. In other embodiments, the method may concern treating an HIV-related condition, the method comprising administering to a subject an effective amount of a compound as disclosed herein, including (E)-4-((3-chlorophenyl)diazenyl)-5-hydroxy-3-(4-nitrophenyl)-1H-pyrazole-1-carbothioamide, 2-{(3Z)-3-[3-(1,1-dioxidotetrahydrothiophen-3-yl)-4-oxo-2-thioxo-1,3-thiazolidin-5-ylidene]-2-oxo-2,3-dihydro-1H-indol-1-yl}-N-(4-methoxyphenyl)acetamide, N-(7-methyl [1,3]thiazolo[4,5-γ][1,3]benzothiazol-2-yl)-2,3-dihydro-1, 4-benzodioxine-6-carboxamide, (4Z)-4-[(4-chlorophenyl) hydrazinylidene]-3-(4-nitrophenyl)-5-oxopyrazole-1-carbothioamide, or [4-(2-hydroxybenzoyl)pyrazol-1-yl]-(3-morpholin-4-ylsulfonylphenyl)methanone. The HIV-related condition may be selected from HIV replication, HIV-associated CD4+ T-cell loss and immunodeficiency, HIV-induced infection, Kaposi's sarcoma, HIV-associated nephropathy, AIDS dementia complex, and combinations thereof.

Embodiments of the disclosed method may be used when the subject is suffering from the HIV-related condition, or the method may be practiced prophylactically or post-exposure prophylactically.

The effective amount used in the disclosed method may be that which is best suited for treating the subject. The effective amount may range from greater than zero to about 1000 mg/kg/day. In particular disclosed embodiments, the effective amount ranges from 1 mg/kg/day to about 100 mg/kg/day. The subject of the disclosed method may be human or an animal and the method may be performed in vitro or in vivo.

The compound disclosed herein may be used in therapy for a Nef-dependent disorder. As disclosed herein, the compound may be used to treat and/or inhibit a biological pathway that is activated by Nef. Such pathways include, but are not limited to, pathways involving a Src-family kinase, such as Hck. In particular disclosed embodiments, the compound may be used to treat or inhibit Nef-dependent HIV-1 replication both in vitro and in vivo. The disclosed compound also may be used to treat or inhibit Nef-dependent HIV-1 infectivity. The disclosed compound therefore may be used to treat HIV. In other disclosed embodiments, the compound may be used to treat or inhibit SIV infectivity or replication.

Particular disclosed embodiments of the compound disclosed herein are potent and selective inhibitors of Nef-dependent Hck activity and therefore may be used in in vitro, in vivo, and ex vivo contexts to regulate or inhibit this activity, prevent any Nef-dependent HIV-1 replication, and downregulate MHC-1, as well as the biological responses that result from such activity. In particular disclosed embodiments, the compound may be used to inhibit HIV-1 infectivity and replication in cell types selected from, but not limited to, U87MG astroglioma cells, CEM-T4 lymphoblasts, TZM-b1 reporter cell line, and CEM-174. Particular disclosed embodiments of the compound disclosed herein may be used to inhibit Nef-dependent HIV replication in the submicromolar range. Embodiments of the disclosed compound may exhibit $IC_{50}$ values for Nef-induced Hck activation in vitro of less than about 3.0 µM; more typically less that about 2.5 µM; even more typically less than about 2.0 µM.

In particular disclosed embodiments, the compound is capable of preventing and/or inhibiting Nef-dependent enhancement of HIV-1 infectivity and replication. The compound is not limited to being active against any particular Nef allele. For instance, embodiments of the disclosed compound are active against a variety of Nef alleles, particularly those that comprise the HIV-1 M-group clades. Exemplary embodiments of the compound may inhibit the replication of various HIV-1 Nef chimeras with an $IC_{50}$ value of 100 nM to about 400 nM; more typically from about 200 nM to about 350 nM; even more typically from about 250 nM to about 300 nM.

Figure 3:
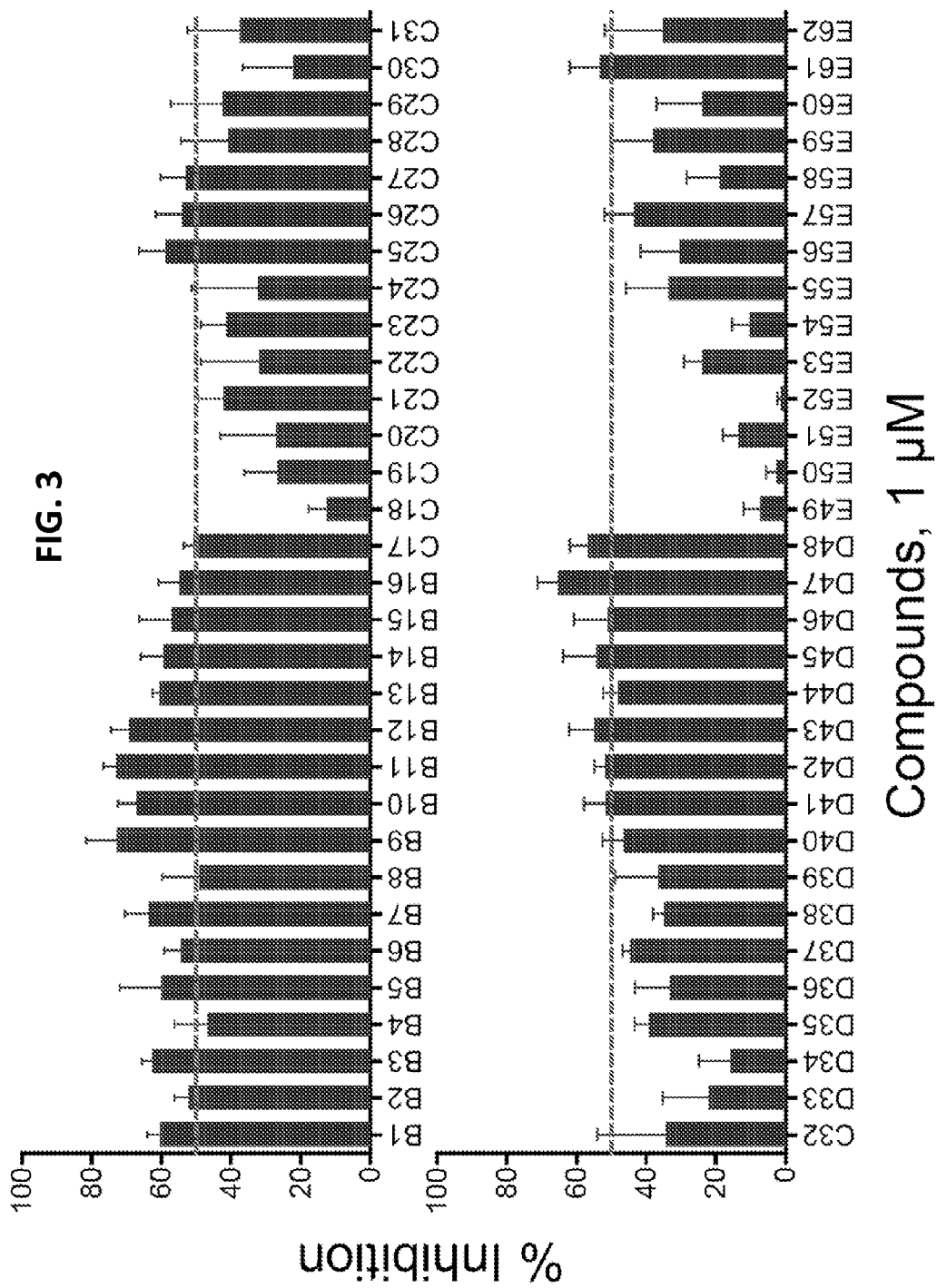
FIG. 3 is a bar graph illustrating results obtained from analyzing the ability of various compounds of the MLSCN library to inhibit HIV replication in U87MG cells. Data are expressed as the mean percent inhibition as compared to control cultures incubated with the carrier solvent (DMSO) ±S.E.M. (n=4).
Figure 4:
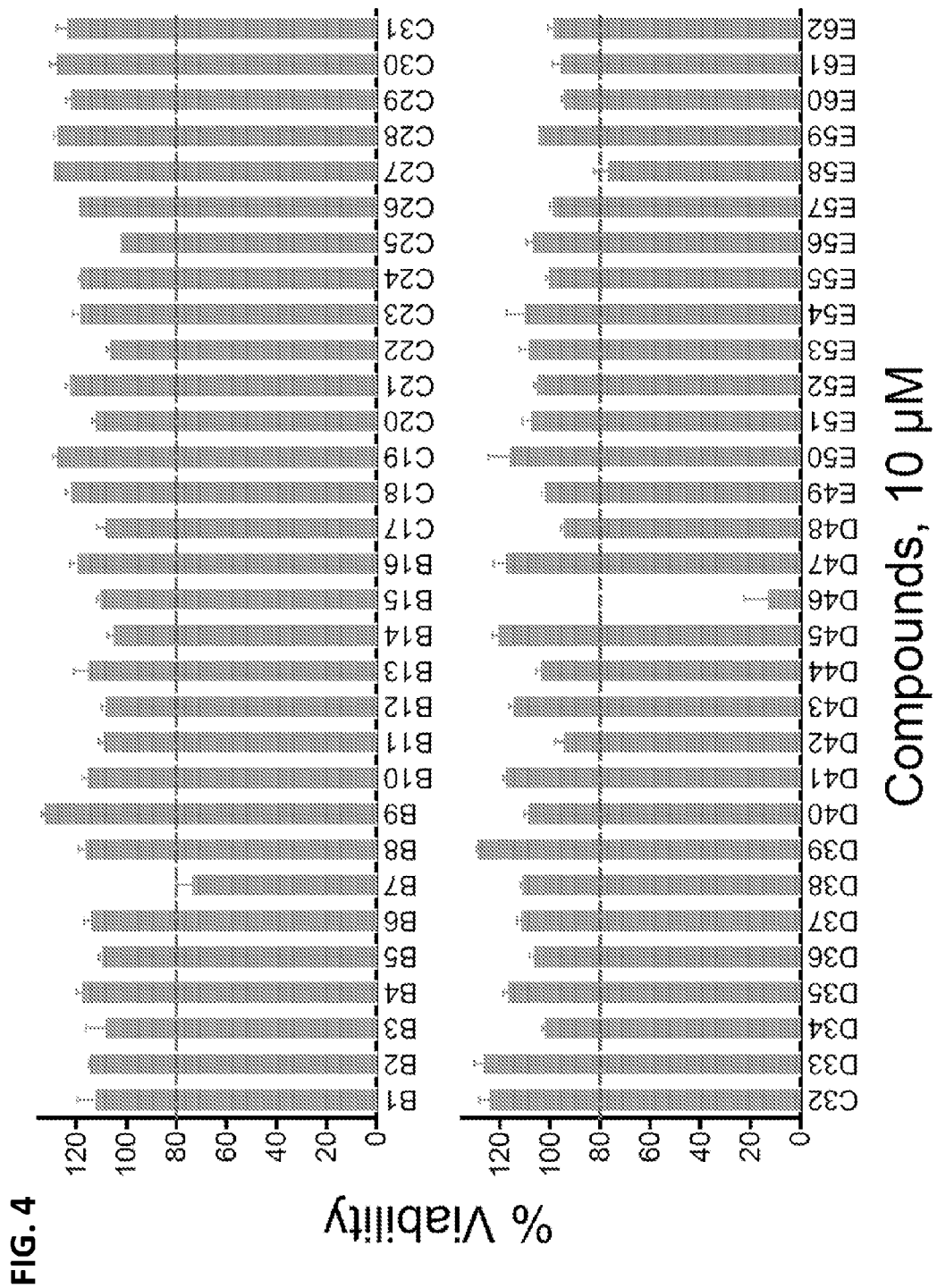
FIG. 4 is a bar graph illustrating the cytotoxicity of various compounds of the MLSCN library after being incubated for 72 hours with U87MG cells at concentrations of 10 μM.
Figure 7:
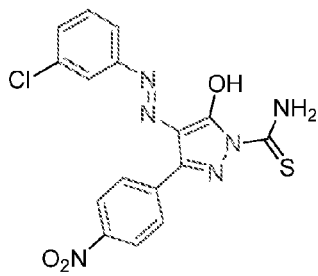
FIG. 7 is an image of various embodiments of compounds used in the methods disclosed herein.
Figure 7:
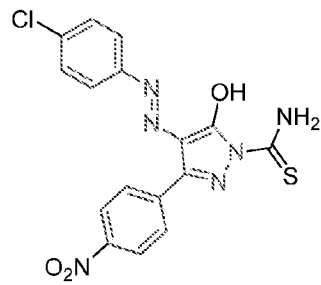
Figure 7:
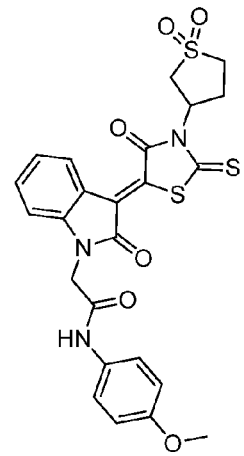
Figure 7:
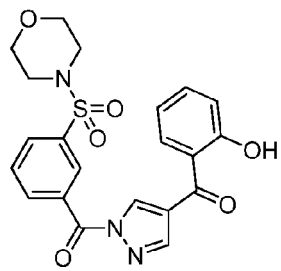
Figure 7:
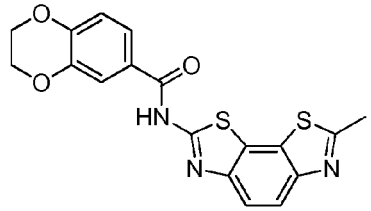
Figure 9:
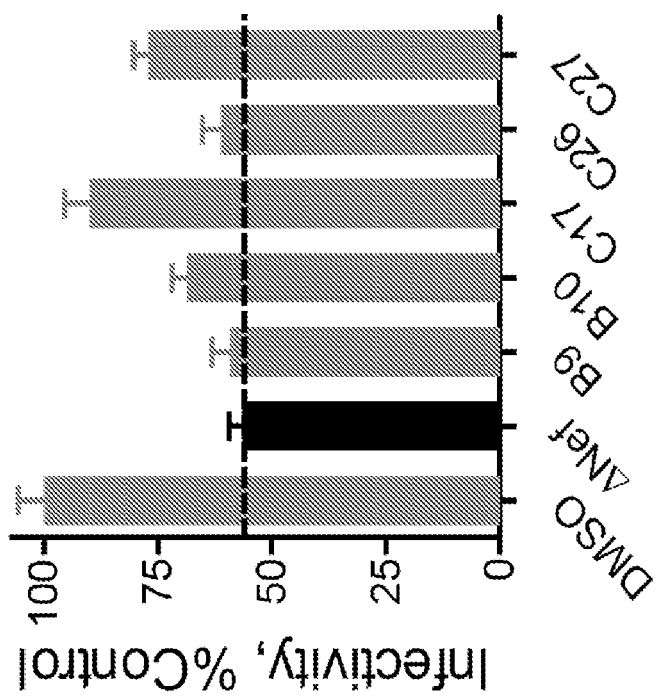
FIG. 9 is a bar graph illustrating relative virus infectivity, with results plotted as the mean percent of HIV-1 infectivity observed in control cells incubated with the carrier solvent DMSO±S.E.M. (n=3).
Figure 8:
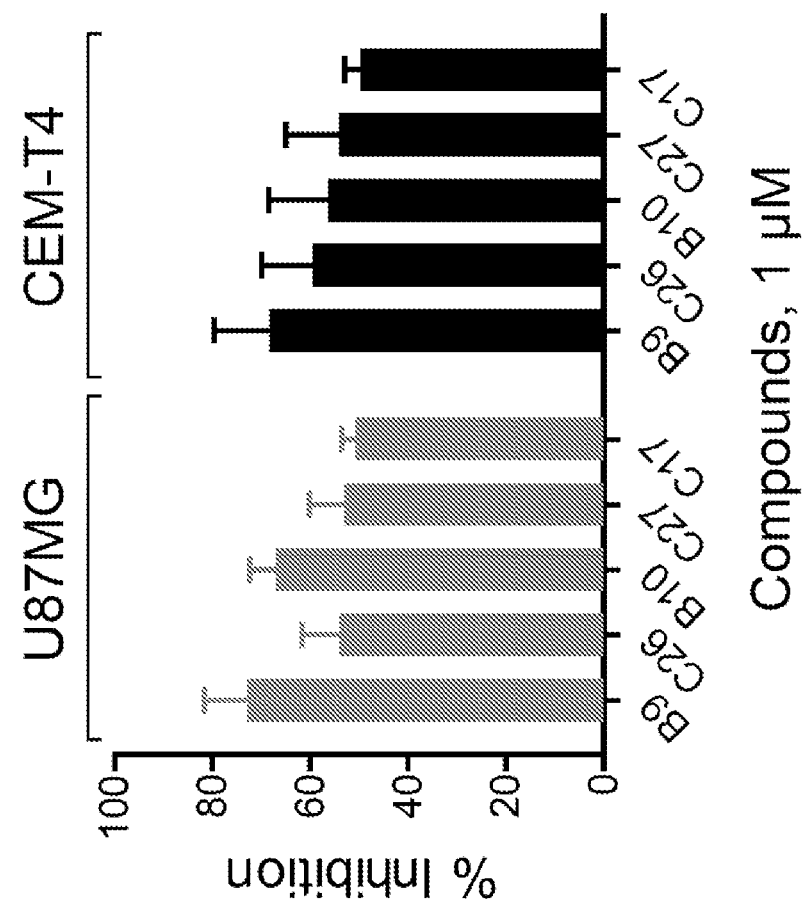
FIG. 8 is a bar graph illustrating data for inhibition of HIV-1 replication in the indicated cell lines obtained from particular embodiments of the disclosed compound. Data are expressed as the mean percent inhibition as compared to control cultures incubated with the carrier solvent (DMSO) ±S.E.M. (n=4).

In particular disclosed embodiments, the compound may be used to block Nef-dependent HIV replication and infectivity. FIG. 7 illustrates the chemical structures of the compounds identified by the Nef:Hck HTS campaign and subsequently shown to block Nef-dependent enhancement of HIV-1 replication in two different cell lines are shown, along with the $IC_{50}$ values for each compound against Hck alone vs. the Nef:Hck complex. FIG. 8 illustrates results concerning HIV replication. Compounds (1 µM) shown in FIG. 7 were added to cultures of U87MG and CEM-T4 cells in 96-well plates, followed by infection with wild-type HIV-1 NL4-3 (50 pg p24 equivalents/ml) 1 hour later. Viral output for the DMSO-treated control cultures was consistently greater than 100-fold over the HIV input, typically ranging from 9,000-12,000 p24 equivalents/ml. Virus replication was assessed by p24 ELISA after 4 days (U87MG) or 9 days (CEM-T4). Data are expressed as the mean percent inhibition as compared to control cultures incubated with the carrier solvent (DMSO)±S.E.M. (n=4). Results of replication and cytotoxicity experiments with all certain hit compounds from the primary screen are shown in FIG. 3 and FIG. 4. FIG. 9 concerns infectivity assays. Compounds (3 µM) were added to cultures of the reporter cell line TZM-b1 followed by infection with either wild-type or Nef-defective (ΔNef) HIV NL4-3 in 96-well plates. After 48 hours, relative virus infectivity was assessed as luciferase production in infected cells. Results are plotted as the mean percent of HIV-1 infectivity observed in control cells incubated with the carrier solvent DMSO±S.E.M. (n=3). In the absence of Nef, infectivity is reduced by about 50% (ΔNef; dashed line shown for reference).

Figure 10:
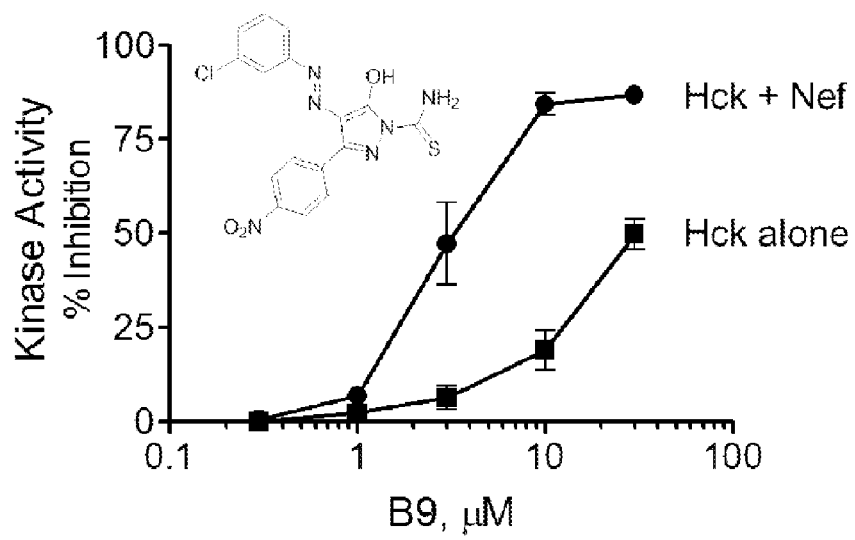
FIG. 10 is a concentration-response curve for an exemplary embodiment of the disclosed compound generated with Nef:Hck complex (circles) vs. Hck alone (squares) using the Z'-lyte kinase assay.
Figure 11:
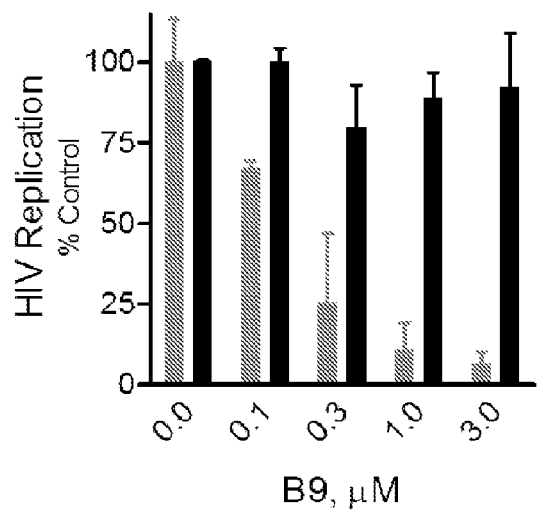
FIG. 11 is a bar graph illustrating viral replication results with the data illustrated as percent of HIV-1 replication relative to the DMSO vehicle control±S.E.M.
Figure 12:
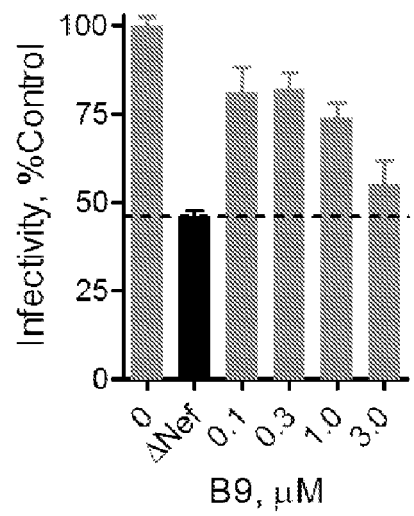
FIG. 12 is a bar graph illustrating results obtained from TZM-b1 cells infected with wild-type and ΔNef HIV NL4-3 in the presence of an exemplary embodiment of the disclosed compound at various concentrations. The data are represented as percent infectivity relative to the DMSO control±S.E.M.

In particular embodiments, an exemplary compound, B9, was chosen as a lead compound to investigate further. FIG. 10 illustrates concentration-response curves for B9 that were generated with the Nef:Hck complex (circles) vs. Hck alone (squares) using the Z'-lyte kinase assay. For Hck alone, approximately 5-fold more kinase protein was added to achieve a similar level of activity as the Nef:Hck complex. Under these conditions, B9 inhibits Nef-dependent Hck activation with an $IC_{50}$ value in the low micromolar range (2.8 µM), while the $IC_{50}$ value for Hck alone is >20 µM. B9 also showed activity against other Src-family members in vitro, with $IC_{50}$ values of >20 µM for c-Src, Lck, and Lyn. While these data support a Nef-dependent mechanism of action, direct action on cellular kinases or other proteins is not excluded. Kinase assays were performed three times in quadruplicate, and the data represent percent inhibition as compared to the DMSO vehicle control±S.E.M. FIG. 11 illustrates results obtained from CEM-T4 cells that were infected with wild-type HIV-1 NL4-3 (grey bars) or the corresponding Nef-defective mutant (ΔNef; black bars) in the presence of the B9 concentrations shown. Viral replication was assessed 9 days later by p24 ELISA. Input virus for HIV-1 ΔNef was increased by ten-fold relative to wild-type to compensate for the reduced infectivity and replication of Nef-defective virus in CEM-T4 cells. This experiment was done in triplicate and data are represented as percent of HIV-1 replication relative to the DMSO vehicle control±S.E.M. FIG. 12 illustrates results from TZM-b1 cells that were infected with wild-type (gray bars) and ΔNef (black bar) HIV NL4-3 in the presence of the B9 concentrations shown, and infectivity was assessed as luciferase activity 48 hours later. This experiment was repeated three times in triplicate and the data are represented as percent infectivity relative to the DMSO control±S.E.M. In the absence of Nef, infectivity is reduced by about 50% (dashed line shown for reference).

Figure 13:
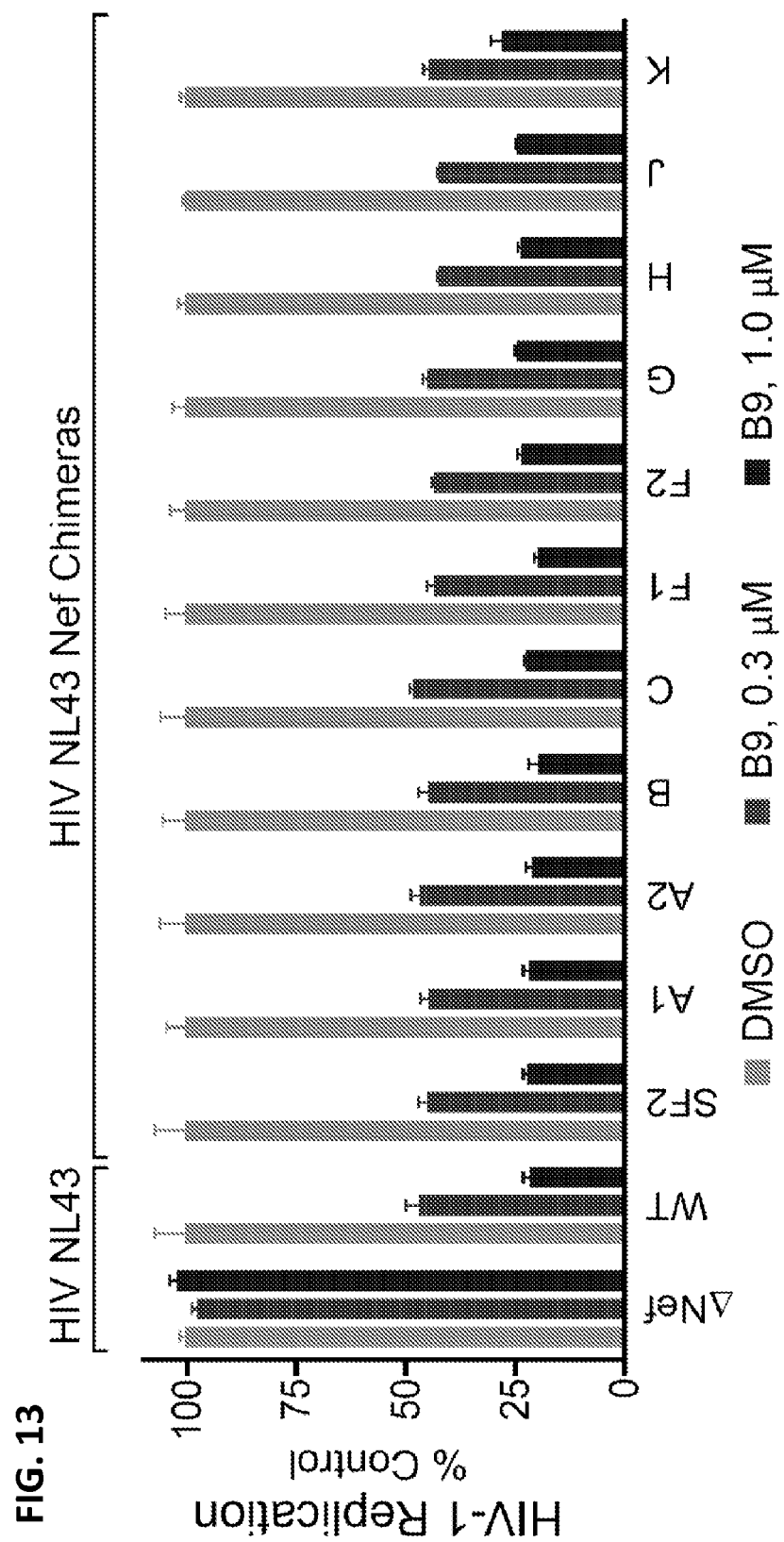
FIG. 13 is bar graph illustrating results obtained from CEM-T4 cells infected with wild-type HIV-1 NL4-3, a Nef-defective mutant (ΔNef), or various Nef chimeras. The data are expressed as the mean percent of HIV-1 replication observed in control cultures incubated with the carrier solvent (0.1% DMSO)±S.D. (n=6).
Figure 14:
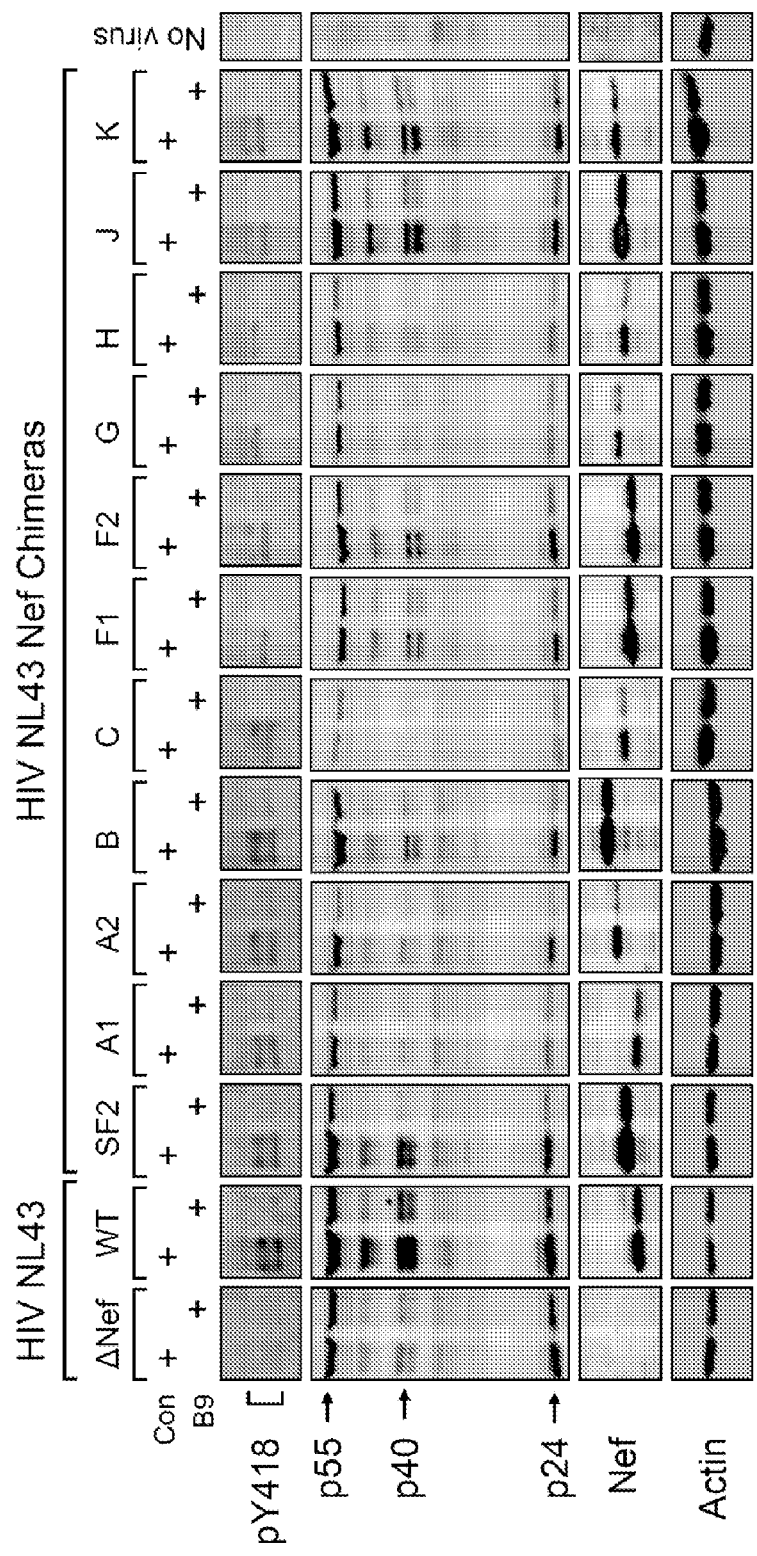
FIG. 14 is an image of various blots obtained from CEM-T4 cells infected with wild-type HIV-1 NL4-3, a Nef-defective mutant (ΔNef), or various Nef chimeras in the presence of an exemplary embodiment of the disclosed compound, or the DMSO carrier solvent as a control (Con). Control blots were performed on cell lysates for HIV-1 Gag proteins (p55, p40, and p24), Nef, as well as actin as a loading control. Results from uninfected cells are shown in the far right lane (No virus).

Also, the inhibition of HIV-1 Nef chimera replication and endogenous SFK activation in CEM-T4 cells by the diphenylpyrazolo compound, B9 was determined FIG. 13 concerns CEM-T4 cells (1×10⁴ per well of a 96-well plate) that were infected with wild-type HIV-1 NL4-3, a Nef-defective mutant (ΔNef), or the indicated Nef chimeras in a final culture volume of 200 µl. Input virus for HIV-1 ΔNef was increased by ten-fold relative to wild-type to compensate for the reduced infectivity and replication of Nef-defective virus in CEM-T4 cells. B9 was added to the cultures to final concentrations of 0.3 and 1.0 µM, and viral replication was determined by p24 ELISA 10 days later. Data are expressed as the mean percent of HIV-1 replication observed in control cultures incubated with the carrier solvent (0.1% DMSO) ±S.D. (n=6). FIG. 14 illustrates results obtained from CEM-T4 cells that were infected with wild-type HIV-1 NL4-3, a Nef-defective mutant (ΔNef), or the indicated Nef chimeras in a final culture volume of 10 ml in the presence of B9 (1 µM) or the DMSO carrier solvent as a control (Con). The infected cells were lysed and Src-family kinase proteins were immunoprecipitated with a pan-specific antibody and protein G-sepharose beads. The SFK activation state was assessed by immunoblotting with a phosphospecific antibody against the activation loop phosphotyrosine residue common to all Src-family members (pY418). Control blots were performed on cell lysates for HIV-1 Gag proteins (p55, p40, and p24), Nef, as well as actin as a loading control. Results from uninfected cells are shown in the far right lane (No virus). This experiment was repeated twice with comparable results.

Figure 21:
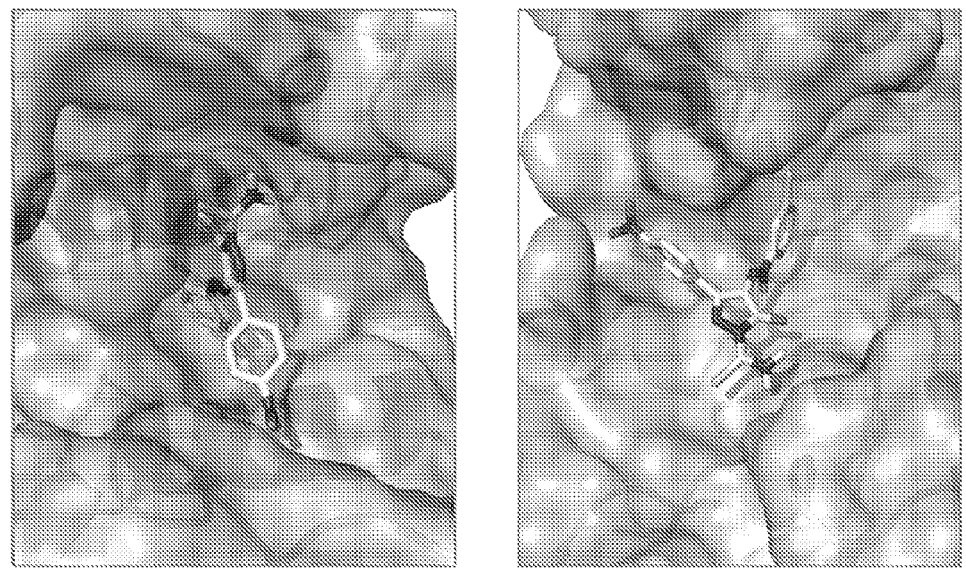
FIG. 21 is an image of results obtained from modeling the binding of exemplary embodiments of the disclosed compound to HIV Nef and SIV Nef.
Figure 21:
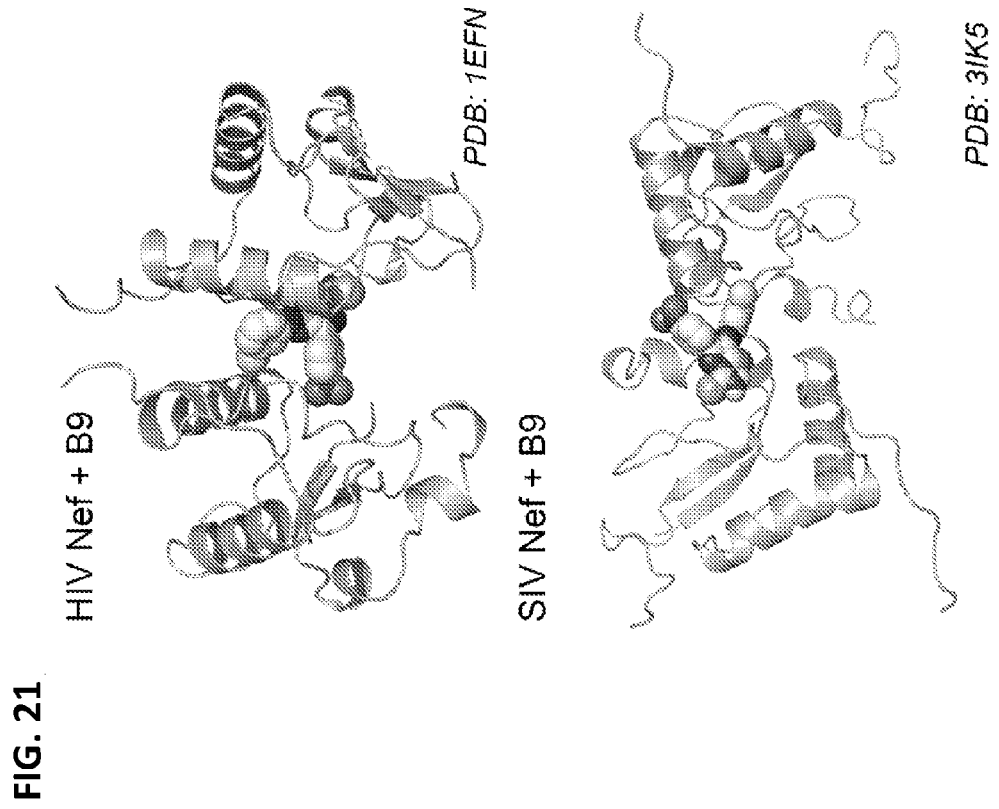
Figure 22:
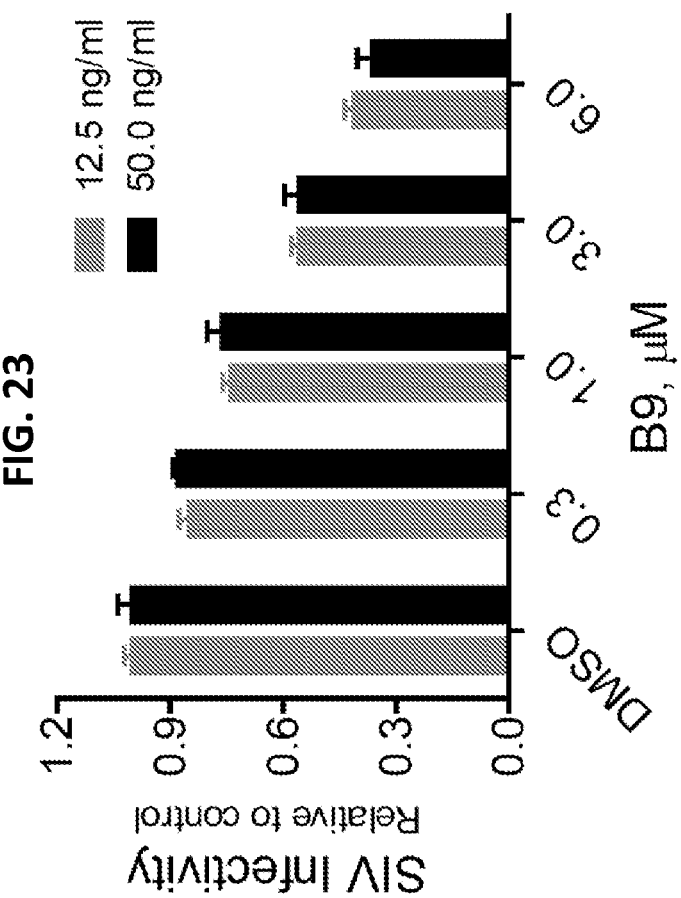
FIG. 22 is a bar graph illustrating the results of SIV replication inhibition obtained from exposing CEM-174 cells to various concentrations of an exemplary embodiment of the disclosed compound.
Figure 23:
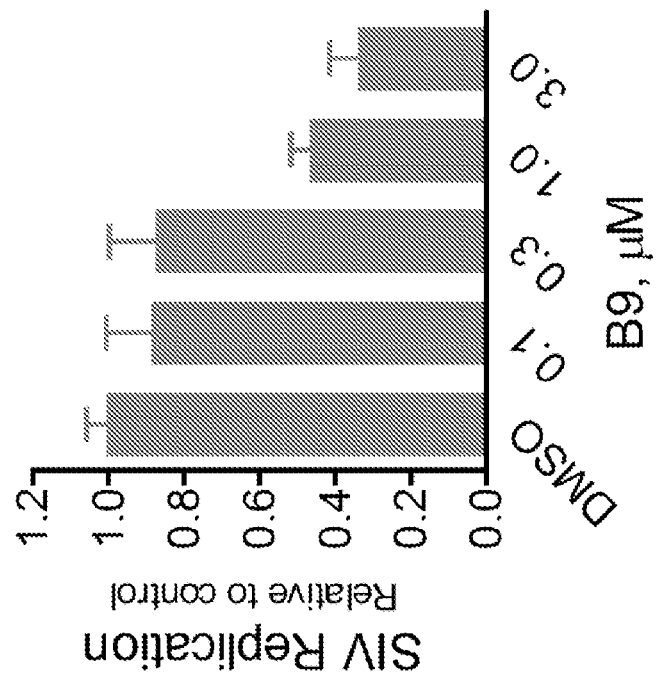
FIG. 23 is a bar graph illustrating the results of SIV infectivity inhibition obtained from exposing the reporter cell line TZM-bl to various concentrations of an exemplary embodiment of the disclosed compound.

FIGS. 21-23 illustrate that the Nef antagonist B9 is predicted to bind to the SIV Nef dimer interface and can inhibit SIV replication and infectivity. FIG. 21 is a model generated using Autodock Vina, which predicts B9 binding to the dimer interface of HIV Nef (top) and SIV Nef (bottom). In each model, the two "halves" of the Nef dimer are modeled in green and blue, respectively. B9 is shown as a space-filling model in the most energetically favored binding sites. Close-up views of the two predicted B9 binding sites are also illustrated in FIG. 21. B9 binds to a pocket in the Nef dimer interface, and is predicted to bind to a groove formed at a similar location in the SIV Nef dimer. FIG. 22 concerns results obtained from SIV replication assays. B9 was solubilized in DMSO and added to cultures of CEM-174 cells at the concentrations shown. Cells were infected with the pathogenic SIV quasispecies ΔB670 1 hour later. Viral replication was assayed after 5 days by SIV p27 Gag ELISA (ZeptoMetrix). FIG. 23 illustrates results from SIV infectivity assays. B9 was added to cultures of the reporter cell line TZM-b1 over the range of concentrations shown, followed by infection with SIV ΔB670 at either 12.5 or 50 ng virus/ml in 96-well plates. Relative virus infectivity was assessed as luciferase production 48 hours later. Results are plotted relative to SIV infectivity observed in control cells incubated with the carrier solvent (DMSO)±S.D.

Figure 24:
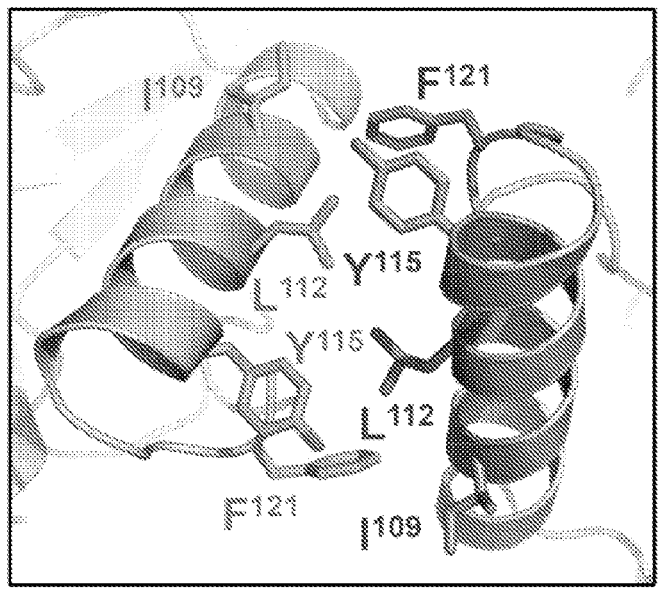
FIG. 24 is molecular model of the Nef dimerization interface, based on the crystal structure of the Nef:SH3 complex.
Figure 25:
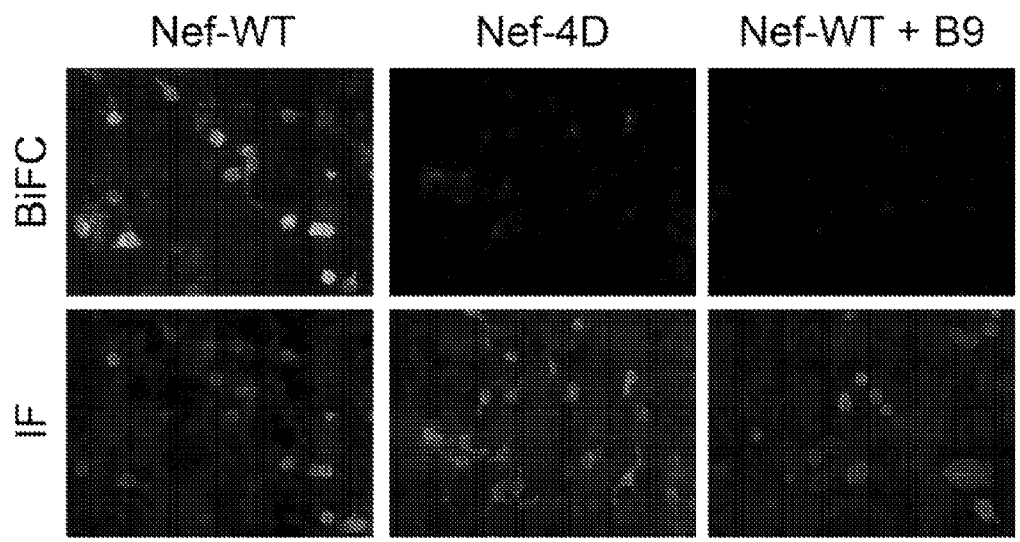
FIG. 25 provides various images illustrating results from human 293T cells that were transfected with Nef-BiFC constructs and incubated with an exemplary embodiment of the disclosed compound.
Figure 27:
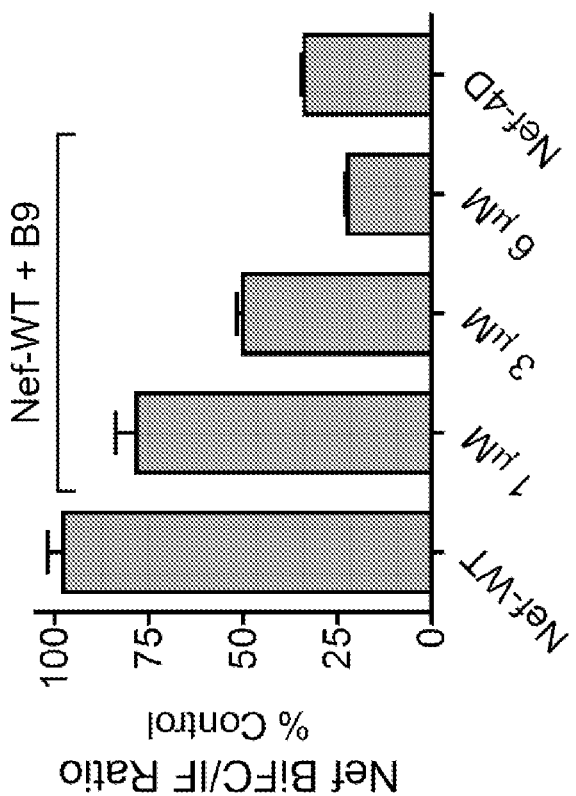
FIG. 27 is a bar chart summarizing the results from 293T cell transfected with Nef-BiFC constructs and exposed to an exemplary embodiment of the disclosed compound over a range of concentrations.
Figure 26:
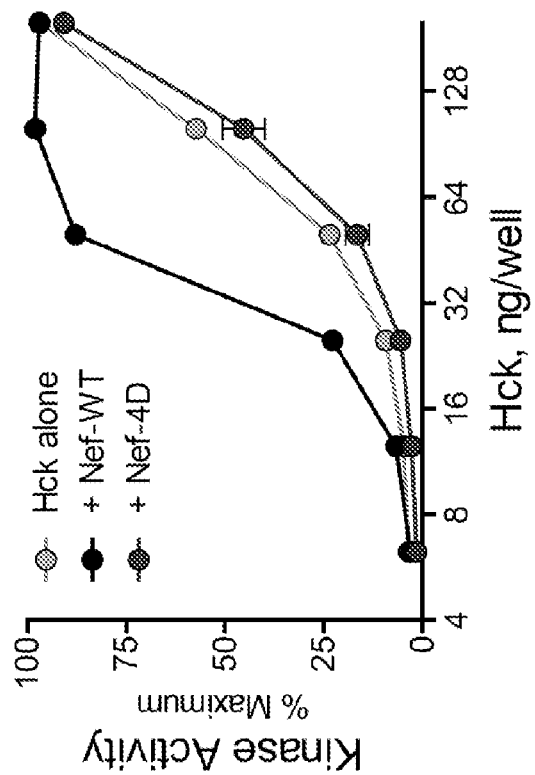
FIG. 26 is a graph illustrating results obtained from the Z'-Lyte kinase assay disclosed herein wherein the kinase is examined alone, or in the presence of wild-type Nef or the Nef-4D mutant.

FIGS. 24-27 illustrate that B9 inhibits Nef dimerization in cells. FIG. 24 is a molecular model of the Nef dimerization interface, based on the crystal structure of the Nef:SH3 complex. Hydrophobic side chains that contribute to dimerization are indicated; substitution of these residues with aspartate (Nef-4D mutant) dramatically reduces Nef dimerization as determined by fluorescence complementation assay. FIG. 25 illustrates results obtained from Human 293T cells that were transfected with Nef-BiFC constructs and incubated with B9 over a range of concentrations. The Nef-4D mutant was included as a negative control. Following incubation for 48 hours, the cells were fixed, stained with a Nef antibody and Texas-red, and analyzed by two-color fluorescence microscopy. FIG. 25 shows representative images from cells expressing the wild-type Nef (Nef-WT) in the absence or presence of B9 (6 µM) as well as the dimerization defective mutant, Nef-4D. FIG. 27 shows the result of image analysis, in which BiFC (Nef dimerization) to immunofluorescence (Nef expression) intensity ratios were calculated for at least 150 cells. Data were normalized to the untreated Nef-WT control, and represent the mean±S.D. FIG. 26 illustrates that Nef-4D fails to activate Hck. Downregulated Hck was assayed in vitro using the Z'-Lyte kinase assay and Tyr2 peptide substrate either alone or in the presence of a 10-fold molar excess of either wild-type Nef (Nef-WT) or the Nef-4D mutant.

Figure 28:
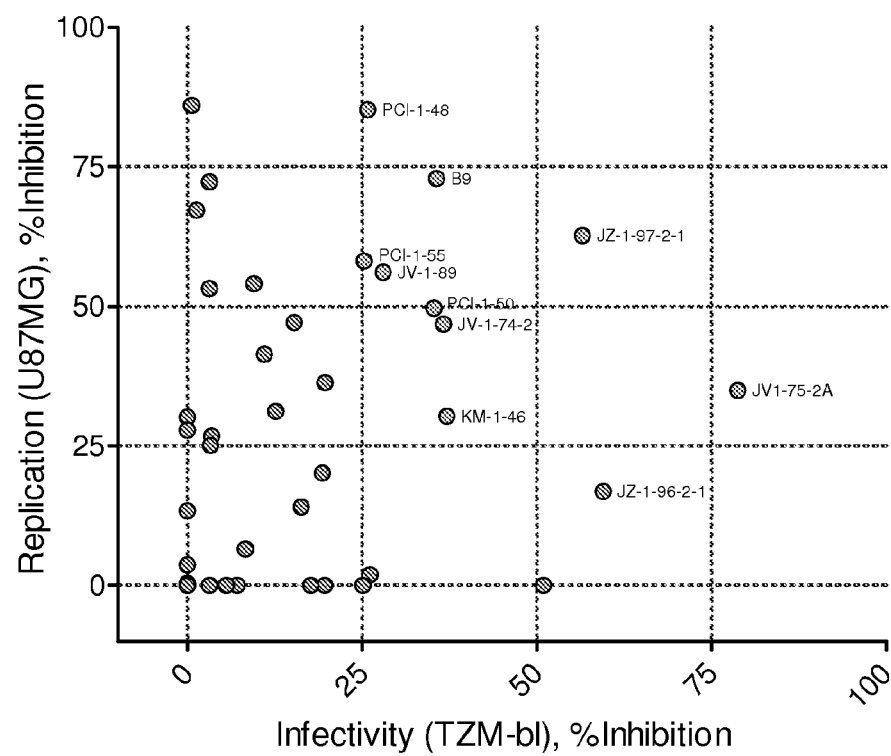
FIG. 28 is a graph illustrating a summarized assessment of various embodiments of the disclosed compound using two cell culture assays for Nef function.
Figure 29:
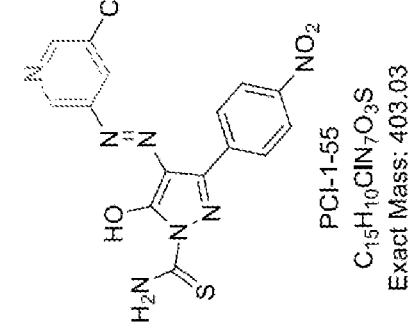
FIG. 29 is an image illustrating the chemical structures of some of the embodiments disclosed in FIG. 28.
Figure 29:
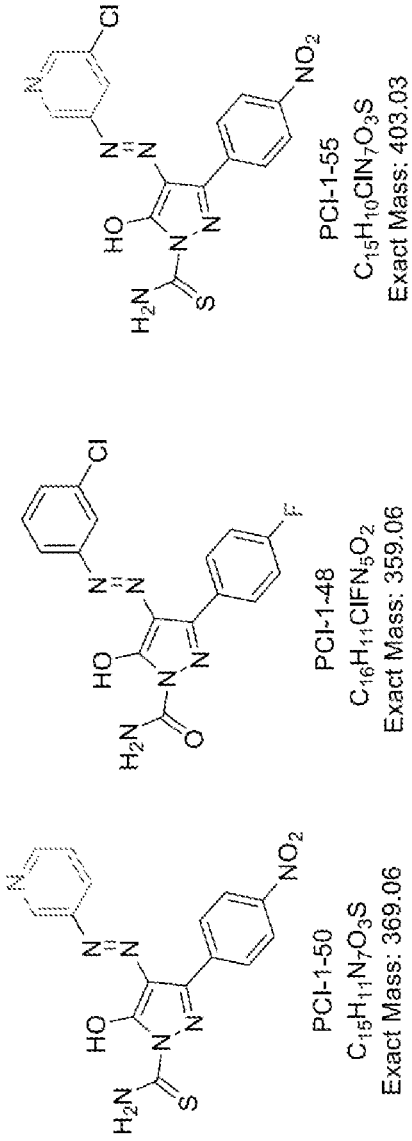
Figure 29:
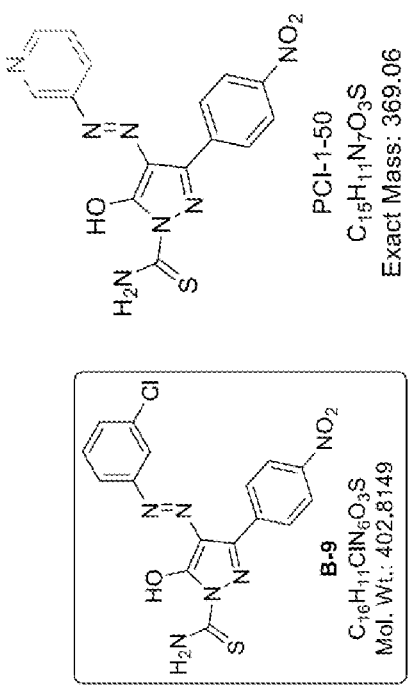
Figure 29:
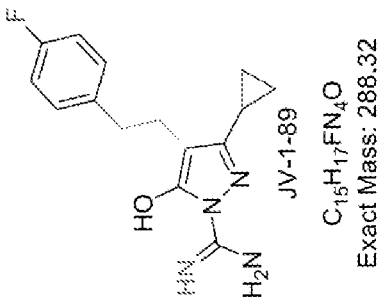
Figure 29:
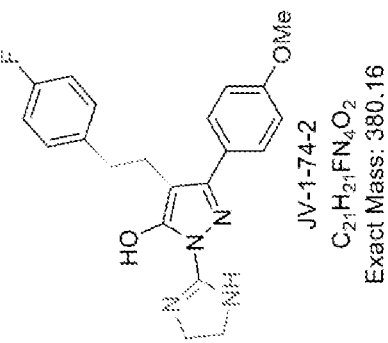
Figure 29:
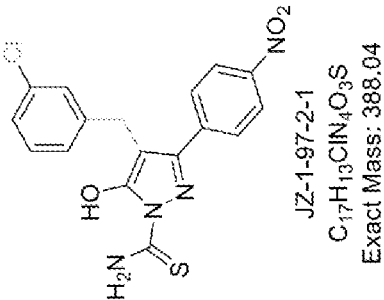

FIG. 28 is a graph summarizing assessment of B9 analog efficacy using two cell culture assays for Nef function. Each compound was assayed at a single concentration (3 µM) for inhibition of Nef-dependent HIV-1 replication in U87MG cells and for inhibition of HIV infectivity in TZM-b1 cells. All assays were repeated at least in triplicate, and the mean percent inhibition relative to a vehicle control (DMSO) is plotted. Compounds that blocked both Nef functions by at least 25% at this concentration are highlighted in green and the structures are shown. Structural modifications relative to the parent B9 structure are highlighted in FIG. 29. Results with B9 are shown for comparison.

Figure 30:
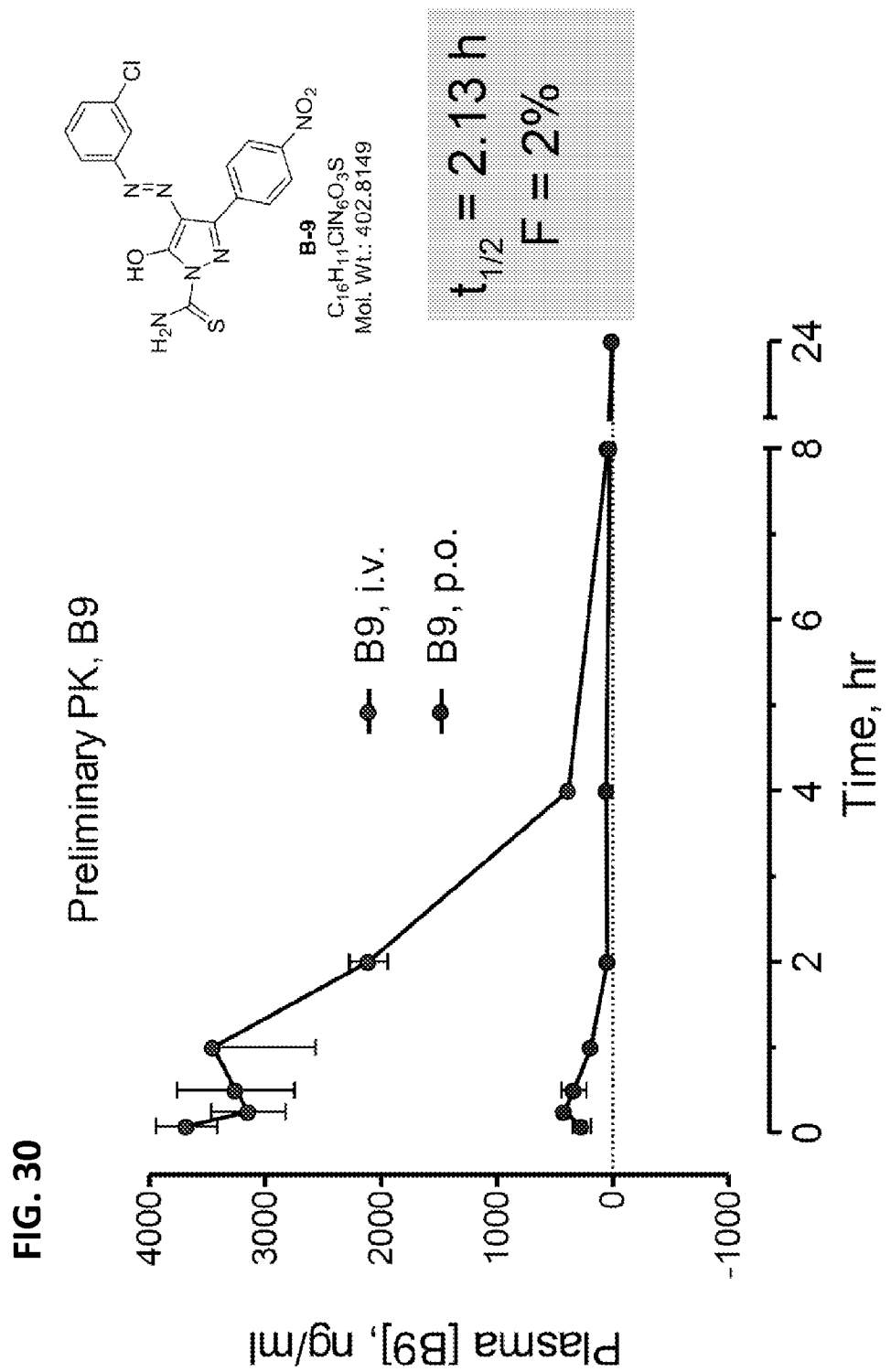
FIG. 30 is a graph illustrating the results of preliminary pharmacokinetics of an exemplary embodiment of the compound disclosed herein.
Figure 31:
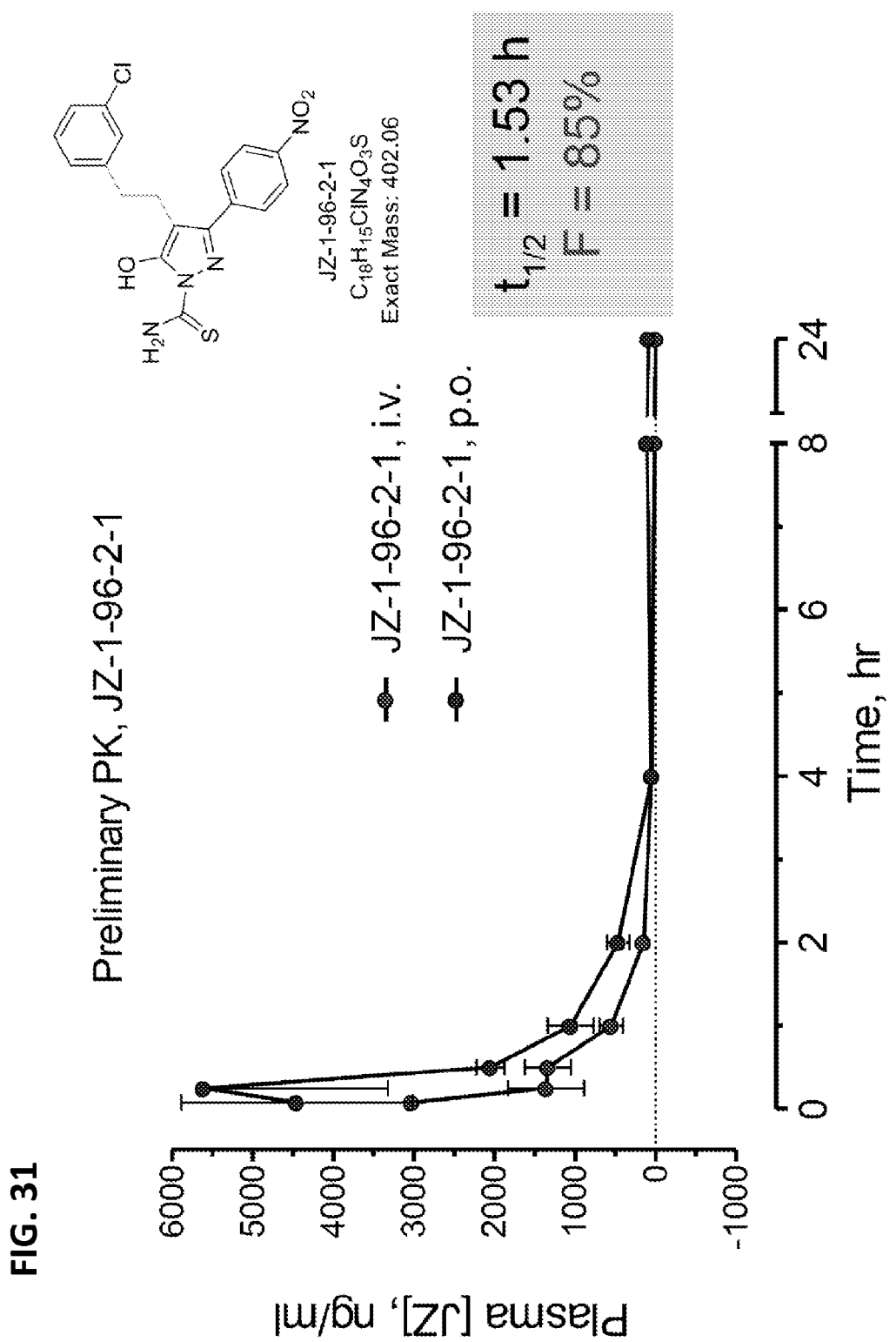
FIG. 31 is a graph illustrating the results of preliminary pharmacokinetics of another exemplary embodiment of the compound disclosed herein.

FIG. 30 illustrates preliminary pharmacokinetics of B9. FIG. 31 illustrates preliminary pharmacokinetics of a non-Azo analog in mice. Compounds were administered to male C3H mice via the i.v. and p.o. routes, and plasma concentrations were assessed by LC-MS/MS at the time points indicated. Plasma levels were determined for three mice at each time point and are shown as the mean±S.D.

Figure 15:
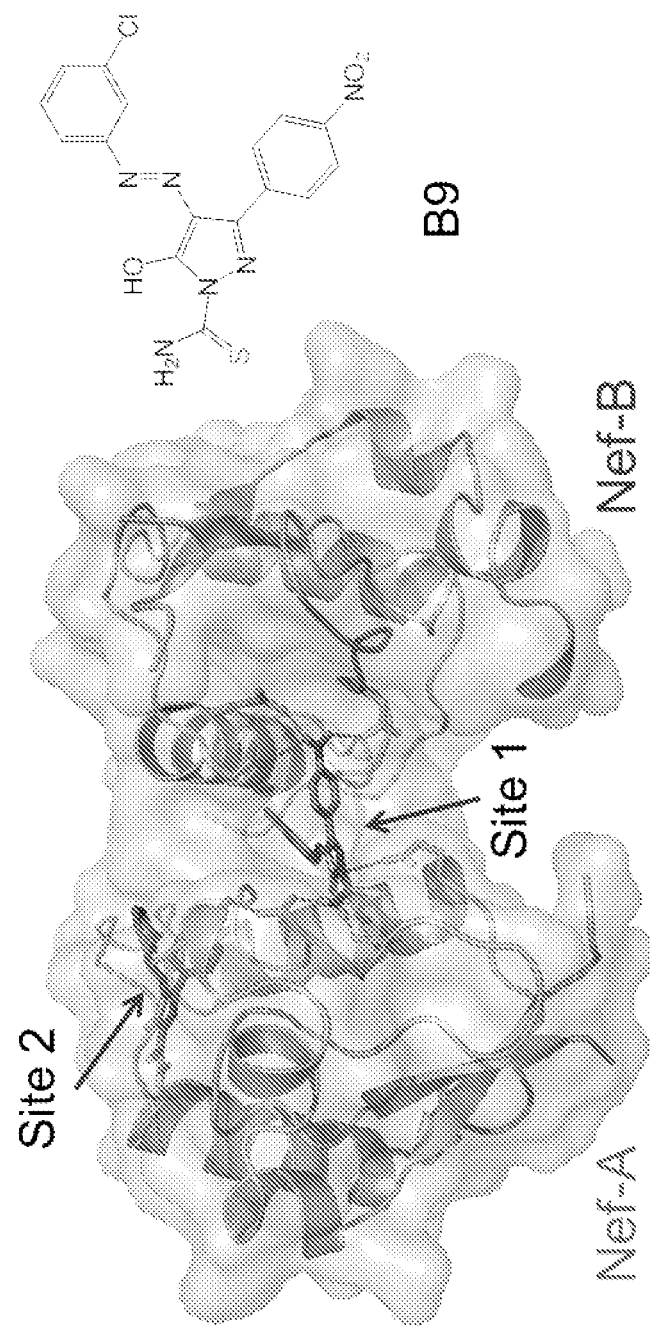
FIG. 15 is an image of a model of the two halves of the Nef dimer, wherein an exemplary embodiment of the disclosed compound is docked at two predicted energetically favored binding sites (Site 1 and Site 2).
Figure 16:
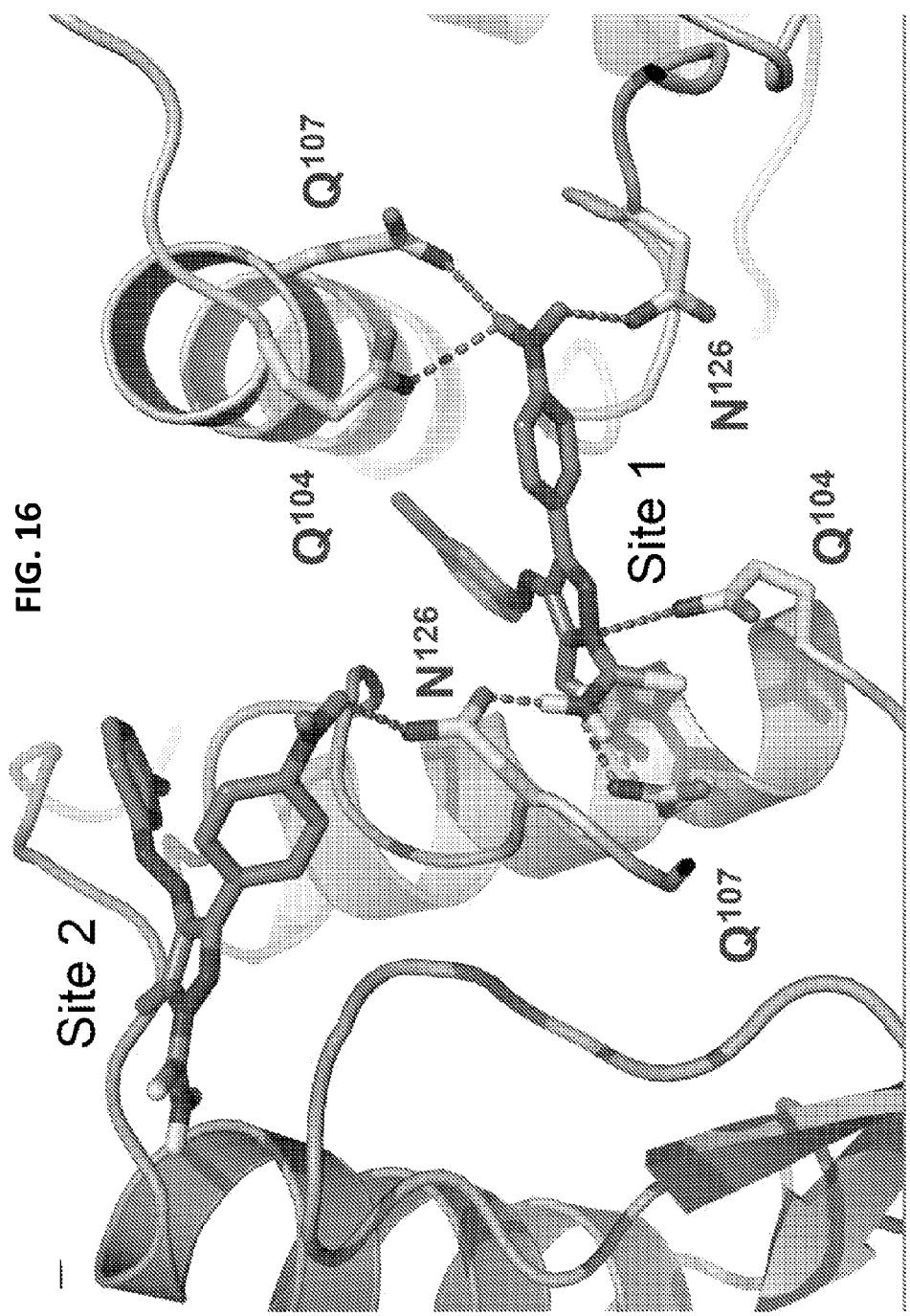
FIG. 16 is an expanded view of the predicted binding sites illustrated in FIG. 15.

Without being limited to a single theory of operation, it currently is believed that the disclosed compound targets Nef in HIV-infected cells. Binding of the disclosed compound to the Nef structure may be determined using methods known to those of ordinary skill in the art, such as using a molecular docking program. Using an appropriate method (e.g., AutoDock Vina), the energetically-favored binding sites for embodiments of the disclosed compound on the Nef protein may be predicted. Two energetically favorable binding sites for a particular embodiment of the disclosed compound were determined, and are illustrated in FIG. 15. According to FIG. 15, this particular embodiment was localized at the Nef dimer interface (site 1) and at the surface of each monomer (site 2). In this particular disclosed embodiment, the predicted binding energy for the Nef dimer interface is more favorable than that for the other site. In particular, the predicted binding energy for site 1 is −8.5 kcal/mol whereas for site 2 it is −7.2 kcal/mol. Without being limited to a particular theory, it is currently believed that disclosed embodiments of the compound may dock at site 1 because of a network of polar contacts with various amino acid residues located within a pocket formed at the Nef dimer interface (e.g., Gln104, Gln107, and Asn126). In contrast, binding site 2 is shallower and involves a single polar contact with Asn126. Table 1 provides a list of binding site residues within 4 Å of a particular embodiment of the disclosed compound, as well as the number of various conformations the compound may be accommodated by each predicted site.

TABLE 1

| Nef Protein | Binding Site | Binding Energy (kcal/mol) | Number of conformers | Binding Site Residues within 4 Å | |
|---|---|---|---|---|---|
| | | | | Chain A | Chain B |
| HIV-1 PDB:1EFN | 1 | −8.5 | 8/9 | Q104, Q107, D108, D111, L112, P122, D123, Q125, N126, Y127 | Q104, Q107, D108, L112, P122, Q125, N126 |
| | 2 | −7.2 | 1/9 | R77, P78, M79, T80, Y81, F121, D123, N126, L137, T138, F139 | |
| SIV PDB:3IK5 | 1 | −8.2 | 9/9 | M111, S112, Y113, K114, T170, F171 | D155, K169, T170, F171, Y223, Y226, F233 |

To validate the B9 binding site predicted using the disclosed model (FIG. 15), a series of three Nef mutants with Ala, Leu, and Gln substitutions for Asn126 was created and predicted to contact the ligand in both binding sites. Each of these mutants was expressed and purified in recombinant form and compared to wild-type Nef in terms of B9 binding by SPR. FIG. 17 illustrates SPR results for recombinant purified HIV-1 Nef-SF2 that was immobilized on the surface of a Biacore CM5 chip; B9 was flowed past Nef at the concentrations shown. The flow path was switched back to buffer after 180 s to induce B9 dissociation (arrow). The resulting sensorgrams (black lines) were best-fit by a heterogeneous ligand (Nef in this case) model (red lines) supporting the presence of two distinct binding sites with Kd values of 860±58 nM and 1.72±0.23 nM. FIG. 18 concerns SPR data that were also fit by a two-state model, which yielded a Kd value 1.79±0.11 nM for the final Nef:B9 complex. FIG. 19 illustrates results obtained when the SPR analysis was repeated with wild-type (WT) Nef and three Nef mutants in which Asn126 is replaced with Leu, Gln, or Ala as shown. B9 was held constant at 10 μM and bound readily to wild-type Nef but not to any of the N126 mutants. As shown in FIG. 19, none of these mutants demonstrated detectable binding to B9, supporting a critical role for Asn126 in B9 binding. To verify that the Nef mutants were properly folded, SPR analysis with the Hck SH3 domain, which binds to a site that is dependent upon the three-dimensional fold of Nef, but is distinct from the B9 binding site.

FIG. 20 provides results obtained from a control experiment used to show that recombinant Nef mutants are not substantially misfolded, supporting the SPR data provided in FIG. 19 and further corroborating that Asn126 is important for binding B9. According to FIG. 20 Nef Asn126 mutants retain their ability to activate Hck. Downregulated Hck was assayed in vitro using the Z'-Lyte kinase assay and Tyr2 peptide substrate either alone or in the presence of a 10-fold molar excess of wild-type Nef or the three Asn126 mutants shown. All four Nef proteins produced an equivalent shift of the Hck activation curve to the left, indicating that mutagenesis of Asn126 does not affect its ability to bind and activate Hck and thus does not disturb the overall folding of the Nef protein.

V. Method for Detecting HIV-Nef Function Antagonists

Also disclosed herein is a method for identifying antimicrobial agents, comprising coupling Nef with a kinase to form a complex, and exposing the complex to one or more compounds selected from those disclosed herein. In particular disclosed embodiments, the kinase is a Src-family kinase. The kinase typically may be Hck, but may be any kinase with which Nef interacts. Nef and Hck may be coupled using methods known to a person of ordinary skill in the art, such as by covalently or electrostatically coupling the two components. In particular disclosed embodiments, a solution of the compound is allowed to come into contact with the complex. In these embodiments, the method may be used to identify antimicrobial agents and agents capable of acting as HIV-Nef function antagonists.

The method may comprise an assay for identifying compounds that are capable of inhibiting a Nef-dependent kinase. The assay typically concerns activation of a natural Nef effector protein, such as Hck, which is dependent upon the presence of Nef. The assay may be used as an alternative to high throughput screening of Nef itself, which lacks biochemical activity. The disclosed method may be used to identify compounds that bind to Nef and are capable of inhibiting antiretroviral activity.

In particular disclosed embodiments, the method is automated in order to enable high throughput screening of a large library of compounds. In particular embodiments, the assay may be used in combination with more than 220,000 compounds. The library of compounds analyzed using the disclosed method need not be kinase biased, thereby increasing the number of potential compounds that may be screened using the disclosed method.

Figure 2:
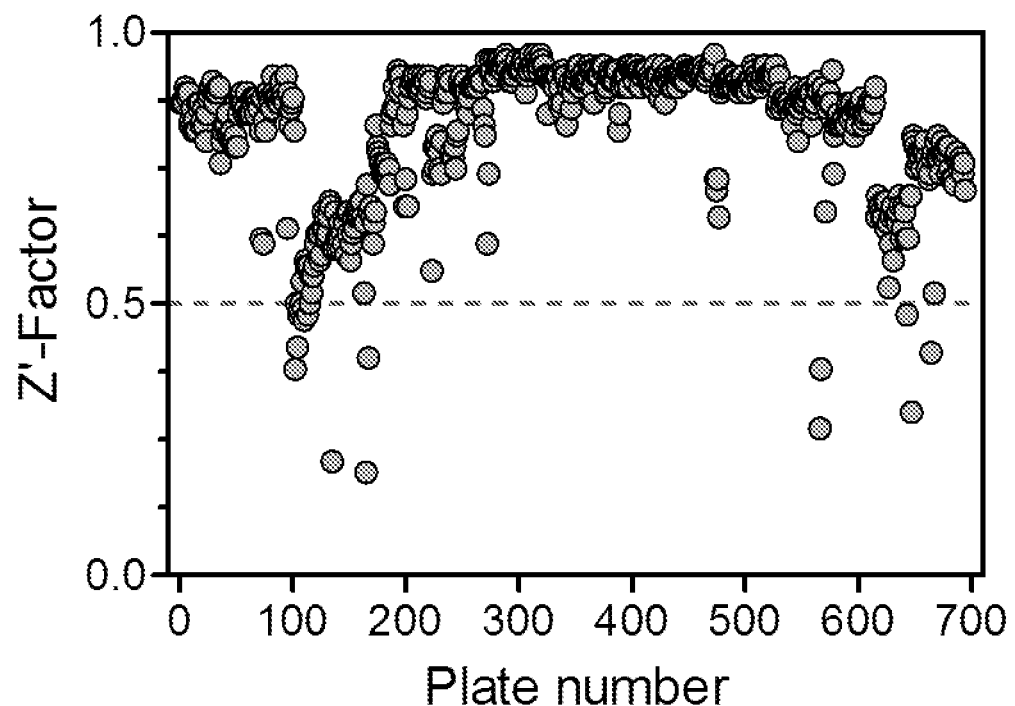
FIG. 2 is a graph illustrating the Z'-Factors obtained using the MLSCN library. Z'-factors for each 384-well plate for the entire high-throughput screening campaign are illustrated.

Using a Nef-coupled kinase assay, the NIH Molecular Library Screening Center Network (MLSCN) collection of more than 220,000 diverse chemical structures can be screened. In particular embodiments, this fully automated HTS campaign yielded 364 confirmed 'hit' compounds with $IC_{50}$ values for Nef-induced Hck activation of less than 20 μM (overall hit rate of ~0.1%; Table 3). Assay results from a representative plate are shown in FIG. 1 and illustrate that kinase activity is entirely dependent upon Nef. Overall, nearly 700×384-well plates were screened, with a composite Z'-factor of 0.83±0.12, indicative of a remarkably robust HTS assay (FIG. 2). All 364 hit compounds were then re-assayed in 10-point concentration-response assays against Nef-induced Hck vs. Hck alone. These experiments identified 66 compounds with at least a 3-fold preference for inhibition of Nef-activated Hck (Tables 2 and 3). These compounds were then assayed for anti-HIV activity as well as cytotoxicity in U87MG astroglioma cells and CEM-T4 lymphoblasts. In U87MG cells, 24 of the 66 compounds (39%) showed more than 50% inhibition of HIV-1 replication at a concentration of 1 μM without toxicity. The response rate in CEM-T4 cells was somewhat lower, with 11 of the 66 hit compounds (18%) blocking replication by more than 50% under the same conditions. Five compounds inhibited HIV-1 replication in both cell lines with low to sub-micromolar potency and without appreciable cytotoxicity. The structures of these compounds, their $IC_{50}$ values for inhibition of the Hck:Nef complex vs. Hck alone, as well as their effects on HIV-1 replication are shown in FIG. 7.

The impact of these five compounds on infectivity using the TZM-b1 reporter cell line was also determined. In this system, infectivity is measured as stimulation of luciferase reporter gene expression driven by the HIV-1 LTR in response to infection with HIV-1, and this effect is enhanced by HIV-1 Nef. As shown in FIG. 9, four of the five compounds suppressed Nef-dependent enhancement of HIV-1 infectivity, providing further support for a Nef-directed antiretroviral mechanism of action.

In particular disclosed embodiments, the method concerns a Nef-Hck coupled kinase assay wherein a functional readout of Nef activity is obtained. Particular disclosed embodiments concern high-throughput screening for inhibitors of Nef-dependent Hck activity. In these embodiments, the NIH Molecular Libraries Screening Centers Network (MLSCN) library (~220,000 compounds) was screened using the FRET-based Nef:Hck in vitro kinase assay as described herein. FIG. 1 is a scatterplot of results from a representative 384-well plate. Under these conditions, Hck is inactive when added by itself (blue circles), while addition of a 10-fold molar excess of Nef induces Hck kinase activation, demonstrating the Nef dependence of the assay (red circles). Compounds were screened at 20 µM under conditions where Hck activity is completely dependent on Nef (grey circles), with >50% inhibition defined as a 'hit' (dashed line). FIG. 2 illustrates Z'-factors for each 384-well plate for the entire high-throughput screening campaign. Of 694 plates screened, 684 passed with Z'-factors ≥0.5 (98.5% pass rate); plates that failed due to robotic error were rescreened and subsequently passed.

VI. Working Embodiments

General Materials and Methods

Recombinant protein expression and purification: Recombinant Hck-YEEI was expressed in Sf9 insect cells as an N-terminal His-tagged fusion protein and purified. Full-length HIV-1 Nef proteins (SF2 allele; wild-type and Asn126 mutants) were expressed in *E. coli* with an N-terminal His-tag and purified.

In vitro kinase assay and chemical library screening: Screening assays were conducted in 384-well plates in a final volume of 10 µl per well using the Z'-lyte kinase assay system and Tyr2 peptide substrate (Life Technologies). Compounds were added to each well (20 µM final concentration) and incubated at room temperature with a preformed complex of Hck-YEEI (15 ng/well) and Nef (1:10 molar ratio, 75 ng/well) for 30 minutes. Reactions were initiated by the addition of ATP (100 µM) and peptide substrate (1 µM), and incubated at room temperature for 45 min Reactions were terminated with 5 µl stop reagent as per the manufacturer's protocol and fluorescence ratios were calculated. The chemical library for this screen was provided by the NIH Molecular Libraries Screening Center Network initiative, and consisted of about 220,000 compounds at the time the primary screen was initiated. The 1495 hit compounds from the primary screen were counter-screened for auto-fluorescence by repeating the assay in the absence of Hck and Nef proteins. A second counter-screen for development reagent (protease) inhibitors was conducted against assay reagents and a tyrosine-phosphorylated Tyr2 control peptide in the absence of Hck and Nef. As per NIH requirements, the complete set of assay results from the primary screen has been deposited in PubChem (UID: 463187).

HIV assays: Viral stocks were prepared by transfection of 293T cells (ATCC) with wild-type and Nef-defective (ΔNef) proviral genomes (NL4—3 strain) and amplified in the T-cell line, MT2 (NIH AIDS Research and Reference Reagent Program). Viral replication was assessed in the U87MG astroglioma cell line engineered to express the HIV-1 co-receptors CD4 and CXCR4 or in the T-lymphoblast cell line, CEM-T4. Both the U87 MG and CEM-T4 cell lines support HIV-1 replication in a Nef-dependent manner, and were obtained from the NM AIDS Research and Reference Reagent Program. Compounds were solubilized in DMSO, and added to the cell culture medium 1 h prior to infection with HIV. Viral replication was monitored for either 4 days (U87MG) or 9 days (CEM-T4) by measuring p24 Gag protein levels in the culture supernatant using standard ELISA-based techniques. HIV-1 infectivity was measured using the reporter cell line, TZM-b1 (NM AIDS Research and Reference Reagent Program). Cells were grown in 96-well plates ($2.5 \times 10^4$) 8 h prior to virus infection to permit adherence. Compounds were pre-incubated with wild-type HIV-1 for 4 h prior to addition to the cells in a final volume of 200 µl. After 48 h at 37° C., the cells were washed with PBS and lysed in luciferase lysis buffer (Promega) by rocking for 15 min Lysates (40 µl) were transferred to white 96-well plates and 50 µl luciferase reagent (Promega) was injected into each well. Readings were recorded with a delay time of 2 sec and an integration period of 10 sec.

The effect of B9 on Nef-mediated activation of endogenous SFK activity was evaluated in CEM-T4 cells. Cells ($1 \times 10^5$) were infected with 50 pg p24 equivalents/ml of wild-type HIV-1 NL4-3, a Nef-defective mutant (ΔNef), or the indicated Nef chimeras in a final culture volume of 10 ml in the presence of 1 µM B9 or the DMSO carrier solvent alone as a control. The infected cells were lysed eight days later and SFK proteins were immunoprecipitated with a pan-specific antibody. SFK activity was assessed by immunoblotting each immunoprecipitate with a phosphospecific antibody against the activation loop phosphotyrosine residue common to all Src family members (pY418; Life Technologies). Control blots were performed on cell lysates for HIV-1 Gag proteins (p55, p40, and p24), Nef, as well as actin as a loading control.

SIV Assays: SIV replication assays were conducted in CEM-174 cells. B9 was solubilized in DMSO and added to the cell culture medium 1 h prior to infection with SIV. Viral replication was assayed 5 d later as p27 Gag protein levels by ELISA (ZeptoMetrix). SIV infectivity was measured using the reporter cell line, TZM-b1, as described above for HIV. B9 was pre-incubated with SIV for 4 h prior to addition to the cells.

Cytotoxicity assays: U87MG or CEM-T4 cells were plated with compounds in DMSO carrier solvent in 96-well plates and incubated at 37° C. After 72 hours, cytotoxicity was assessed using the Cell Titer Blue reagent (Promega) and the manufacturer's protocol.

Surface plasmon resonance (SPR): Recombinant full-length Nef (SF2 strain) with an N-terminal His-tag was expressed in bacteria and purified. Nef was then exchanged into HBS-EP buffer (10 mM HEPES, pH 7.4, 150 mM NaCl, 3 mM EDTA, 0.05% v/v P20 surfactant) and concentrated with an Amicon Ultra 10 kDa molecular weight cutoff spin concentrator. SPR analysis was performed on a BIAcore 3000 instrument using a four-channel CM5 biosensor chip at 25° C. The Nef protein was covalently attached to the CM5 chip via standard amine coupling chemistry. B9 (as analyte)

was prepared in PBS buffer (10 mM $Na_2HPO_4$, 1.8 mM $KH_2PO_4$, 2.7 mM KCl, 137 mM NaCl) with 1% DMSO and flowed past the immobilized Nef protein channel and a reference channel on the biosensor CM5 chip at a flow rate of 50 μl/min for 3 min over a range of concentrations (FIGS. 17-20). The initial binding reaction was followed by dissociation for 5 min, and the chip surface was regenerated using HBS-EPD buffer HBS-EPD buffer (10 mM HEPES, pH 7.4, 150 mM NaCl, 3 mM EDTA, 0.05% v/v P20, 1 mM DTT) at a flow rate of 50 μl/min for 10 min. The sensorgram curves recorded at each B9 concentration were assessed in triplicate, corrected for buffer effects, and fitted with the heterogeneous ligand-parallel reaction model using the BIAevaluation 4.1 software suite. In this model, one analyte (B9 in this case) interacts with two independent binding sites on the ligand (two predicted binding sites on Nef in this case), i.e., $A+B1+B2 \leftrightarrows AB1+AB2$, where A is the analyte while B1 and B2 represent the independent binding sites. In addition, the data were also fit to a two-state binding model, in which binding of B9 induces a conformational change in Nef to stabilize the binding. The two-state model assumes two states of Nef-B9 complexes, AB and AB*, which correspond to simple binding of B9 to Nef (AB) and a conformational change to a stable complex (AB*), i.e., $A+B \leftrightarrows AB \leftrightarrows AB^*$.

Molecular docking: The 3D structure of B9 was docked to the crystal structures of both HIV-1 Nef (PDB: 1EFN; without the SH3 domain) and SIV mac239 Nef (PDB: 3IK5) in their dimeric conformations using AutoDock Vina available at http://vina.scripps.edu. The three-dimensional structures of compound, B9 and the Nef dimers were first converted from pdb into pdbqt format using MGL Tools. The structure of each Nef dimer was treated as the receptor and was kept rigid during the docking routine. In contrast, rotatable bonds in the structure of B9 imparted flexibility on the ligand. A grid box was centered at the 43.76, 18.61, 37.94 (HIV Nef) and 26.43, −7.16, −23.57 (SIV Nef) coordinates with 60 Å units in the x, y and z directions to cover the entire structure in each case. Docking of B9 to both Nef dimer structures returned 9 lowest-energy conformations of the ligand. Of these, the Nef:B9 complexes showing the lowest binding energies and the greatest number of conformations in a cluster were chosen for further study (Table 1).

BiFC Assay for Nef dimerization: The effect of B9 on Nef dimerization was assessed using a cell-based BiFC assay. Briefly, 293T cells were plated on glass coverslips and allowed to attach overnight. Cells were then treated with B9 or the DMSO carrier solvent alone for 30 min prior to transfection with the Nef-BiFC plasmid pair using XtremeGene9 and the manufacturer's protocol (Roche). Forty-eight hours later, cells were fixed and stained with anti-Nef antibodies, and immunostained cells were visualized with secondary antibodies conjugated to Texas red. Two-color immunofluorescent images were recorded at fixed exposure times for each channel using a Nikon TE300 inverted microscope with epifluorescence capability and a SPOT CCD high-resolution digital camera and software. Image analysis was performed to determine mean pixel intensities in the BiFC (dimerization) and immunofluorescence (expression) channels of individual cells using Image J. BiFC to immunofluorescence ratios were calculated for at least 150 cells from each condition and are presented as percent of ratios obtained with DMSO-treated cells expressing wild-type Nef.

Example 1

Using the Nef-coupled kinase assay disclosed herein, the NIH Molecular Library Screening Center Network (MLSCN) collection was screened. The MLSCN contains more than 220,000 diverse chemical structures. This fully automated HTS campaign yielded 364 confirmed 'hit' compounds with $IC_{50}$ values for Nef-induced Hck activation of less than 20 μM (overall hit rate of ~0.1%; Table 2). Assay results from a representative plate are shown in FIG. 1 and illustrate that kinase activity is entirely dependent upon Nef. Overall, nearly 700×384-well plates were screened, with a composite Z'-factor of 0.83±0.12, indicative of a remarkably robust HTS assay (FIG. 2).

TABLE 2

Summary of HIV-1 Nef:Hck High Throughput Screening Campaign.

| Stage | | Compounds (percent) |
|---|---|---|
| Primary HTS | Input Compounds | 220,335 (100) |
| | >50% Inhibition at 20 μM | 1495 (0.68) |
| Counterscreens | Autofluorescent compounds | 358 |
| | Substrate FRET Quench | 49 |
| | Inactive | 499 |
| | >50% Inhibition Confirmed | 364 (0.16) |
| Concentration-response[a] | $IC_{50}$ Nef:Hck < 20 μM | 342 |
| | Nef:Hck $IC_{50}$ < 6.6 μM Hck alone $IC_{50}$ > 20 μM | 66 (0.03) |
| Nef-dependent Anti-HIV Activity[b] | | 5 |

[a]Compound $IC_{50}$ data and SID codes from this stage can be found in Table 3.
[b]$IC_{50}$ < 1 μM for HIV-1 replication in both U87MG and CEM-T4 cells.

Example 2

All 364 hit compounds from Example 1 were then re-assayed in 10-point concentration-response assays against Nef-induced Hck vs. Hck alone. These embodiments identified 66 compounds with at least a 3-fold preference for inhibition of Nef-activated Hck (Tables 2 and 3). Compounds that showed at least a 3-fold inhibitory preference for the Nef-Hck complex vs. Hck alone (or inhibited the Nef-Hck complex with an $IC_{50}$ value ≤6.6 μM while inhibiting Hck alone with an $IC_{50}$ value >20 μM) were carried forward into HIV replication assays (indicated with italicized text in Table 3). The five compounds shown in FIG. 7 that inhibit HIV replication by 50% or more in both U87MG and CEM-T4 cells at a concentration of 1 μM are underlined. The short-hand designations for the active compounds are indicated in the far right column of Table 3 (Alias), and "N/A" indicates compounds that were not available for further study. The PubChem SID code for each compound is indicated in the far left column of Table 3.

TABLE 3

Identification of hit compounds that selectively inhibit the Nef-Hck complex.

| | Hck + Nef | | Hck Alone | | | |
|---|---|---|---|---|---|---|
| SID | $IC_{50}$ μM | % Inhib (20 μM) | $IC_{50}$ μM | % Inhib (20 μM) | $IC_{50}$ Ratio | Alias |
| 26670695 | 0.23 | 121.7 | 16.73 | 80.1 | 72.2 | B14 |
| 24803612 | 1.95 | 118.5 | 10.73 | 73.4 | 5.5 | N/A |
| 26671681 | 3.00 | 107.2 | 13.90 | 48.9 | 4.6 | B4 |
| 3717177 | 1.12 | 108.0 | 5.19 | 65.2 | 4.6 | D34 |
| 26667032 | 2.47 | 103.1 | 11.34 | 60.3 | 4.6 | B12 |
| 26725244 | 2.64 | 100.7 | 11.51 | 40.3 | 4.4 | B5 |
| 22405745 | 1.16 | 67.9 | 4.84 | 65.6 | 4.2 | C28 |
| 26665950 | 2.80 | 98.7 | 10.64 | 60.8 | 3.8 | E56 |

TABLE 3-continued

Identification of hit compounds that selectively inhibit the Nef-Hck complex.

| | Hck + Nef | | Hck Alone | | | |
|---|---|---|---|---|---|---|
| SID | IC$_{50}$ μM | % Inhib (20 μM) | IC$_{50}$ μM | % Inhib (20 μM) | IC$_{50}$ Ratio | Alias |
| 22405111 | 1.16 | 118.3 | 4.37 | 73.0 | 3.8 | C32 |
| 17514788 | 4.88 | 128.5 | 18.21 | 87.9 | 3.7 | D43 |
| 24790189 | 5.36 | 122.8 | 20.00 | 49.7 | 3.7 | C26 |
| 26725076 | 3.95 | 92.8 | 14.16 | 54.9 | 3.6 | E60 |
| 24784416 | 3.40 | 101.9 | 12.20 | 61.7 | 3.6 | B11 |
| 26727248 | 2.60 | 102.0 | 9.30 | 65.4 | 3.6 | E55 |
| 26725322 | 3.76 | 84.3 | 12.89 | 65.5 | 3.4 | C21 |
| 26726119 | 5.39 | 82.9 | 18.28 | 57.1 | 3.4 | B8 |
| 24816825 | 2.26 | 95.0 | 7.60 | 58.6 | 3.4 | D40 |
| 24823649 | 4.33 | 136.0 | 14.14 | 91.0 | 3.3 | D45 |
| 24788512 | 1.33 | 103.4 | 4.27 | 78.0 | 3.2 | D42 |
| 22414709 | 1.563 | 106.3 | 4.99 | 75.6 | 3.2 | N/A |
| 24781057 | 1.00 | 125.5 | 3.18 | 81.9 | 3.2 | C25 |
| 26665513 | 3.47 | 232.8 | 11.00 | 59.0 | 3.2 | C24 |
| 26725358 | 2.64 | 102.6 | 8.27 | 86.7 | 3.1 | C18 |
| 24795765 | 5.53 | 96.9 | 17.15 | 56.1 | 3.1 | B6 |
| 24819009 | 3.44 | 93.9 | 9.93 | 56.8 | 2.9 | |
| 24803726 | 4.69 | 112.8 | 13.39 | 70.5 | 2.9 | |
| 24823515 | 3.19 | 106.0 | 9.01 | 69.5 | 2.8 | |
| 24803582 | 4.15 | 104.6 | 11.14 | 76.3 | 2.7 | |
| 24822983 | 5.83 | 100.4 | 15.62 | 56.2 | 2.7 | |
| 24816740 | 2.16 | 111.6 | 5.78 | 83.8 | 2.7 | |
| 24823724 | 7.14 | 105.6 | 19.03 | 52.0 | 2.7 | |
| 3717942 | 1.45 | 79.8 | 3.77 | 71.3 | 2.6 | |
| 26665480 | 1.71 | 100.1 | 4.37 | 77.9 | 2.6 | |
| 24822911 | 6.31 | 112.8 | 15.94 | 85.3 | 2.5 | |
| 17514186 | 1.902 | 75.8 | 4.78 | 54.2 | 2.5 | |
| 26725321 | 1.87 | 109.8 | 4.70 | 64.5 | 2.5 | |
| 26671423 | 3.56 | 90.9 | 8.71 | 66.5 | 2.4 | |
| 14732523 | 6.789 | 120.5 | 16.30 | 65.1 | 2.4 | |
| 17504227 | 7.751 | 108.6 | 18.25 | 56.9 | 2.4 | |
| 858325 | 5.23 | 114.8 | 12.30 | 78.1 | 2.4 | |
| 17401922 | 7.748 | 87.1 | 18.06 | 57.0 | 2.3 | |
| 26671424 | 3.70 | 95.6 | 8.59 | 68.5 | 2.3 | |
| 24820894 | 2.80 | 111.1 | 6.46 | 66.9 | 2.3 | |
| 26671559 | 6.00 | 118.2 | 13.83 | 67.6 | 2.3 | |
| 14733575 | 7.232 | 106.2 | 16.28 | 58.8 | 2.3 | |
| 22412028 | 8.75 | 54.6 | 19.64 | 47.7 | 2.2 | |
| 17514844 | 3.66 | 99.7 | 7.85 | 51.4 | 2.1 | |
| 26670776 | 4.92 | 92.0 | 10.53 | 67.6 | 2.1 | |
| 24785982 | 3.17 | 91.2 | 6.77 | 70.8 | 2.1 | |
| 17508547 | 3.06 | 96.0 | 6.12 | 71.0 | 2.0 | |
| 26725591 | 0.82 | 124.4 | 1.61 | 87.7 | 2.0 | |
| 24791574 | 4.30 | 123.6 | 8.46 | 92.5 | 2.0 | |
| 24787080 | 8.42 | 68.3 | 16.26 | 64.5 | 1.9 | |
| 24797546 | 2.58 | 108.6 | 4.95 | 91.2 | 1.9 | |
| 24818586 | 3.91 | 103.0 | 7.49 | 64.5 | 1.9 | |
| 26725320 | 4.22 | 57.5 | 7.96 | 74.1 | 1.9 | |
| 17433362 | 9.974 | 107.1 | 18.78 | 53.6 | 1.9 | |
| 24789652 | 7.14 | 119.3 | 13.35 | 68.4 | 1.9 | |
| 24796817 | 9.14 | 87.4 | 16.99 | 58.7 | 1.9 | |
| 26731947 | 6.18 | 111.7 | 11.46 | 65.4 | 1.9 | |
| 17503820 | 5.51 | 91.2 | 10.18 | 65.5 | 1.8 | |
| 26729962 | 8.39 | 75.6 | 15.34 | 60.0 | 1.8 | |
| 14746067 | 9.551 | 113.6 | 17.43 | 57.0 | 1.8 | |
| 24795086 | 7.69 | 92.5 | 13.89 | 63.3 | 1.8 | |
| 24802556 | 6.22 | 101.1 | 11.19 | 71.1 | 1.8 | |
| 24822510 | 5.22 | 128.8 | 8.94 | 81.2 | 1.7 | |
| 24838078 | 9.17 | 80.1 | 15.58 | 59.5 | 1.7 | |
| 24822711 | 4.22 | 101.7 | 7.11 | 67.3 | 1.7 | |
| 22405512 | 6.98 | 111.9 | 11.74 | 69.6 | 1.7 | |
| 26658023 | 9.45 | 88.4 | 15.80 | 70.8 | 1.7 | |
| 24823532 | 11.43 | 74.0 | 18.99 | 61.3 | 1.7 | |
| 24814601 | 4.22 | 87.6 | 6.99 | 77.9 | 1.7 | |
| 24827556 | 7.26 | 89.1 | 12.01 | 66.5 | 1.7 | |
| 4260800 | 5.659 | 101.3 | 9.19 | 77.7 | 1.6 | |
| 26666548 | 6.71 | 95.4 | 10.82 | 70.9 | 1.6 | |
| 24816838 | 3.21 | 103.8 | 5.15 | 77.5 | 1.6 | |
| 26731711 | 11.85 | 79.8 | 18.97 | 55.5 | 1.6 | |
| 17415430 | 8.861 | 69.4 | 14.04 | 78.0 | 1.6 | |
| 24822520 | 9.82 | 43.4 | 15.51 | 63.6 | 1.6 | |
| 24782730 | 8.83 | 85.9 | 13.91 | 69.9 | 1.6 | |
| 24793903 | 7.50 | 80.0 | 11.79 | 65.8 | 1.6 | |
| 17511256 | 9.92 | 76.4 | 15.47 | 64.0 | 1.6 | |
| 24823206 | 5.05 | 124.0 | 7.85 | 84.2 | 1.6 | |
| 24780194 | 10.15 | 131.6 | 15.39 | 89.8 | 1.5 | |
| 26731914 | 2.70 | 131.4 | 4.10 | 82.9 | 1.5 | |
| 24816773 | 5.88 | 93.9 | 8.86 | 72.6 | 1.5 | |
| 17432365 | 9.847 | 111.5 | 14.62 | 67.3 | 1.5 | |
| 24832424 | 9.70 | 82.3 | 14.18 | 61.9 | 1.5 | |
| 17410481 | 8.681 | 115.8 | 12.60 | 66.6 | 1.5 | |
| 865107 | 2.012 | 105.9 | 2.90 | 88.4 | 1.4 | |
| 24780626 | 4.54 | 79.8 | 6.43 | 75.7 | 1.4 | |
| 17385658 | 10.070 | 119.7 | 14.26 | 72.7 | 1.4 | |
| 24823338 | 8.94 | 85.8 | 12.40 | 58.6 | 1.4 | |
| 24779997 | 9.61 | 104.6 | 13.20 | 65.4 | 1.4 | |
| 26731782 | 1.31 | 125.2 | 1.79 | 96.7 | 1.4 | |
| 26664464 | 1.56 | 93.8 | 2.08 | 80.7 | 1.3 | |
| 26666751 | 0.62 | 117.3 | 0.83 | 96.4 | 1.3 | |
| 24823563 | 1.80 | 106.4 | 2.38 | 94.0 | 1.3 | |
| 24825655 | 9.08 | 88.6 | 11.95 | 65.9 | 1.3 | |
| 24832975 | 12.60 | 63.5 | 16.52 | 55.0 | 1.3 | |
| 865848 | 6.745 | 92.8 | 8.84 | 70.5 | 1.3 | |
| 14742965 | 5.731 | 84.5 | 7.49 | 75.4 | 1.3 | |
| 24841442 | 1.72 | 83.7 | 2.19 | 77.9 | 1.3 | |
| 17505082 | 11.592 | 117.5 | 14.66 | 81.4 | 1.3 | |
| 26726169 | 8.61 | 83.5 | 10.88 | 78.0 | 1.3 | |
| 24790255 | 2.14 | 104.0 | 2.70 | 85.7 | 1.3 | |
| 24825251 | 7.75 | 68.4 | 9.72 | 64.1 | 1.3 | |
| 26670281 | 10.56 | 70.4 | 13.20 | 59.6 | 1.3 | |
| 24818713 | 0.72 | 130.3 | 0.90 | 96.4 | 1.2 | |
| 26731921 | 3.42 | 108.1 | 4.24 | 84.0 | 1.2 | |
| 26731915 | 1.48 | 120.9 | 1.83 | 85.8 | 1.2 | |
| 26662562 | 3.13 | 115.9 | 3.83 | 88.1 | 1.2 | |
| 17515175 | 4.27 | 98.9 | 5.12 | 81.5 | 1.2 | |
| 4246816 | 8.394 | 110.8 | 9.93 | 68.0 | 1.2 | |
| 26658783 | 12.42 | 83.0 | 14.64 | 75.6 | 1.2 | |
| 26661145 | 8.26 | 84.7 | 9.71 | 86.3 | 1.2 | |
| 17432606 | 5.272 | 125.1 | 6.20 | 94.7 | 1.2 | |
| 22409882 | 2.96 | 45.0 | 3.36 | 81.5 | 1.1 | |
| 26731888 | 3.49 | 91.4 | 3.90 | 75.5 | 1.1 | |
| 3717588 | 5.28 | 106.2 | 5.85 | 85.2 | 1.1 | |
| 24802153 | 4.02 | 100.1 | 4.45 | 81.2 | 1.1 | |
| 22409543 | 1.194 | 101.4 | 1.30 | 82.4 | 1.1 | |
| 17514877 | 4.83 | 94.0 | 5.25 | 79.7 | 1.1 | |
| 17509848 | 5.892 | 85.9 | 6.38 | 69.0 | 1.1 | |
| 864887 | 16.614 | 63.3 | 17.74 | 55.9 | 1.1 | |
| 14741663 | 4.059 | 90.6 | 4.31 | 80.5 | 1.1 | |
| 26670041 | 15.77 | 62.1 | 16.45 | 55.1 | 1.0 | |
| 26665829 | 12.54 | 68.8 | 12.78 | 64.2 | 1.0 | |
| 7973773 | 14.252 | 80.6 | 14.02 | 69.5 | 1.0 | |
| 17385788 | 12.152 | 56.9 | 11.67 | 65.2 | 1.0 | |
| 24820635 | 6.57 | 96.7 | 6.26 | 75.9 | 1.0 | |
| 14730734 | 2.335 | 112.6 | 2.11 | 92.7 | 0.9 | |
| 7971844 | 10.016 | 73.7 | 8.97 | 68.3 | 0.9 | |
| 856959 | 10.193 | 93.8 | 9.06 | 77.8 | 0.9 | |
| 17410678 | 6.047 | 79.5 | 5.26 | 97.5 | 0.9 | |
| 14734255 | 8.691 | 84.4 | 7.51 | 79.7 | 0.9 | |
| 17513613 | 6.794 | 88.0 | 5.86 | 80.1 | 0.9 | |
| 17402282 | 0.058 | 123.9 | 0.05 | 100.7 | 0.8 | |
| 17415220 | 1.765 | 101.2 | 1.49 | 74.4 | 0.8 | |
| 22401280 | 6.786 | 117.8 | 5.68 | 66.1 | 0.8 | |
| 24816781 | 6.02 | 102.2 | 5.03 | 80.2 | 0.8 | |
| 26731917 | 2.62 | 122.3 | 2.17 | 91.2 | 0.8 | |
| 4258401 | 4.764 | 102.0 | 3.94 | 84.0 | 0.8 | |
| 17402368 | 0.044 | 122.7 | 0.04 | 101.4 | 0.8 | |
| 17415777 | 9.885 | 55.6 | 7.71 | 41.4 | 0.8 | |
| 861167 | 11.010 | 88.3 | 8.47 | 79.0 | 0.8 | |
| 17402399 | 0.173 | 118.5 | 0.13 | 100.7 | 0.7 | |
| 3717937 | 5.991 | 109.3 | 4.42 | 93.4 | 0.7 | |
| 4254661 | 7.331 | 93.9 | 5.33 | 77.7 | 0.7 | |
| 22412588 | 3.375 | 112.6 | 2.37 | 88.7 | 0.7 | |
| 4252165 | 10.211 | 85.5 | 7.02 | 75.8 | 0.7 | |
| 3713277 | 10.059 | 85.4 | 6.82 | 77.2 | 0.7 | |

TABLE 3-continued

Identification of hit compounds that selectively inhibit the Nef-Hck complex.

| SID | Hck + Nef IC$_{50}$ μM | Hck + Nef % Inhib (20 μM) | Hck Alone IC$_{50}$ μM | Hck Alone % Inhib (20 μM) | IC$_{50}$ Ratio | Alias |
|---|---|---|---|---|---|---|
| 3714986 | 13.973 | 70.3 | 9.24 | 70.1 | 0.7 | |
| 17407216 | 9.517 | 91.5 | 6.24 | 77.9 | 0.7 | |
| 4248992 | 13.364 | 76.0 | 6.81 | 73.0 | 0.5 | |
| 3712774 | 9.220 | 87.2 | 4.63 | 79.2 | 0.5 | |
| 7975124 | 3.209 | 107.9 | 1.50 | 91.4 | 0.5 | |
| 17414966 | 13.997 | 55.9 | 6.21 | 63.6 | 0.4 | |
| 14744444 | 9.016 | 55.9 | 3.95 | 70.2 | 0.4 | |
| 3713760 | 14.096 | 51.4 | 5.29 | 70.8 | 0.4 | |
| 4250517 | 4.759 | 118.2 | 1.77 | 45.6 | 0.4 | |
| 24822291 | 1.37 | 119.9 | >20.000 | 43.8 | | E61 |
| 26731546 | 2.22 | 100.6 | >20.000 | 36.5 | | C20 |
| 26725303 | 2.68 | 89.6 | >20.000 | 38.7 | | E53 |
| 24835040 | 2.71 | 79.9 | >20.000 | 14.1 | | B10 |
| 26726147 | 2.87 | 109.4 | >20.000 | 26.9 | | C27 |
| 24824263 | 2.94 | 107.2 | >20.000 | 49.6 | | B15 |
| 26727102 | 3.05 | 103.7 | >20.000 | 20.9 | | D47 |
| 22402342 | 3.12 | 139.9 | >20.000 | 16.7 | | D48 |
| 24792136 | 3.37 | 82.1 | >20.000 | 39.0 | | B3 |
| 26657962 | 3.43 | 107.9 | >20.000 | 26.5 | | E58 |
| 24803676 | 3.67 | 96.4 | >20.000 | 56.6 | | D41 |
| 22410475 | 3.75 | 69.2 | >20.000 | 31.0 | | E52 |
| 24836735 | 3.76 | 86.1 | >20.000 | 38.6 | | N/A |
| 24822597 | 3.79 | 95.9 | >20.000 | 46.2 | | C23 |
| 26663375 | 3.91 | 89.4 | >20.000 | 54.5 | | E51 |
| 24833646 | 4.03 | 110.4 | >20.000 | 53.1 | | D44 |
| 26663188 | 4.06 | 111.2 | >20.000 | 32.0 | | D37 |
| 26670150 | 4.10 | 77.9 | >20.000 | 29.6 | | E50 |
| 26670610 | 4.14 | 127.7 | >20.000 | 16.6 | | C29 |
| 26670998 | 4.17 | 99.5 | >20.000 | 24.4 | | B13 |
| 4257184 | 4.36 | 116.7 | >20.000 | 20.7 | | D46 |
| 24830965 | 4.41 | 108.4 | >20.000 | 36.2 | | C22 |
| 24781728 | 4.54 | 118.3 | >20.000 | 21.9 | | C19 |
| 26725943 | 4.56 | 65.1 | >20.000 | 25.8 | | D35 |
| 24784817 | 4.66 | 110.7 | >20.000 | 26.6 | | D39 |
| 26665141 | 4.71 | 98.8 | >20.000 | 43.6 | | B7 |
| 4252095 | 4.785 | 92.5 | >20.000 | 31.1 | | C17 |
| 3716671 | 4.807 | 121.9 | >20.000 | -7.0 | | B2 |
| 856002 | 4.83 | 117.4 | >20.000 | -41.0 | | C31 |
| 22401406 | 4.89 | 122.4 | >20.000 | 23.6 | | N/A |
| 24784551 | 5.04 | 114.3 | >20.000 | 9.8 | | B9 |
| 26725443 | 5.27 | 102.3 | >20.000 | 47.0 | | B16 |
| 22410746 | 5.45 | 75.0 | >20.000 | 19.2 | | E54 |
| 4263567 | 5.49 | 98.0 | >20.000 | 41.4 | | D36 |
| 3712134 | 5.604 | 108.2 | >20.000 | 48.1 | | C30 |
| 22410295 | 5.62 | 102.1 | >20.000 | 8.0 | | E57 |
| 24824002 | 5.80 | 68.1 | >20.000 | 32.3 | | D33 |
| 17386763 | 5.849 | 113.3 | >20.000 | 58.3 | | E62 |
| 22409900 | 5.97 | 93.2 | >20.000 | 40.6 | | N/A |
| 17408801 | 6.210 | 75.0 | >20.000 | 49.2 | | D38 |
| 24781196 | 6.38 | 101.5 | >20.000 | 8.9 | | B1 |
| 24787956 | 6.58 | 125.0 | >20.000 | 3.4 | | E49 |
| 24833521 | 6.61 | 110.3 | >20.000 | 20.1 | | E59 |
| 22401671 | 6.74 | 93.4 | >20.000 | 30.8 | | |
| 17504780 | 6.846 | 98.6 | >20.000 | 51.8 | | |
| 26725881 | 7.00 | 92.4 | >20.000 | 50.0 | | |
| 4250972 | 7.08 | 84.6 | >20.000 | 40.9 | | |
| 24789662 | 7.15 | 71.4 | >20.000 | 29.4 | | |
| 26725602 | 7.36 | 89.7 | >20.000 | 8.9 | | |
| 24836779 | 7.39 | 75.7 | >20.000 | 35.5 | | |
| 26727985 | 7.43 | 86.1 | >20.000 | -2.8 | | |
| 24823273 | 7.50 | 108.8 | >20.000 | 11.4 | | |
| 26731948 | 7.64 | 82.6 | >20.000 | 48.9 | | |
| 24828713 | 7.82 | 74.9 | >20.000 | 47.4 | | |
| 24791484 | 7.83 | 96.7 | >20.000 | 50.5 | | |
| 24820349 | 7.89 | 63.6 | >20.000 | 26.1 | | |
| 22401998 | 7.95 | 87.0 | >20.000 | 12.2 | | |
| 26661831 | 8.04 | 76.2 | >20.000 | 44.2 | | |
| 24797173 | 8.15 | 78.3 | >20.000 | 1.2 | | |
| 17401902 | 8.344 | 112.0 | >20.000 | 36.7 | | |
| 17388467 | 8.367 | 113.2 | >20.000 | 33.5 | | |
| 26664137 | 8.38 | 103.5 | >20.000 | 19.4 | | |
| 24784513 | 8.40 | 90.8 | >20.000 | 7.9 | | |
| 24791424 | 8.49 | 76.6 | >20.000 | 60.1 | | |
| 24791767 | 8.53 | 83.2 | >20.000 | 19.2 | | |
| 24841620 | 8.70 | 81.7 | >20.000 | 14.4 | | |
| 24779467 | 8.75 | 80.5 | >20.000 | 23.3 | | |
| 17407106 | 8.763 | 94.5 | >20.000 | 61.9 | | |
| 3716129 | 8.844 | 117.8 | >20.000 | -36.4 | | |
| 26658242 | 8.95 | 106.0 | >20.000 | 31.2 | | |
| 24797595 | 9.00 | 53.3 | >20.000 | 22.9 | | |
| 4257331 | 9.224 | 105.9 | >20.000 | 49.4 | | |
| 26657545 | 9.37 | 79.9 | >20.000 | 24.9 | | |
| 22402988 | 9.41 | 79.7 | >20.000 | 22.2 | | |
| 24791896 | 9.41 | 72.6 | >20.000 | 34.1 | | |
| 4241879 | 9.500 | 55.8 | >20.000 | 38.6 | | |
| 24787003 | 9.56 | 88.5 | >20.000 | 35.9 | | |
| 24804069 | 9.58 | 58.5 | >20.000 | -3.0 | | |
| 26729299 | 9.59 | 99.5 | >20.000 | 11.2 | | |
| 24802540 | 9.73 | 117.3 | >20.000 | 8.5 | | |
| 24822570 | 9.74 | 90.9 | >20.000 | 18.8 | | |
| 17413364 | 9.79 | 77.1 | >20.000 | 9.2 | | |
| 22413657 | 9.83 | 75.0 | >20.000 | 33.0 | | |
| 17433711 | 9.925 | 116.7 | >20.000 | 34.7 | | |
| 17432499 | 10.075 | 106.7 | >20.000 | 12.3 | | |
| 26665710 | 10.12 | 67.7 | >20.000 | 17.5 | | |
| 17386621 | 10.233 | 86.4 | >20.000 | 21.7 | | |
| 24833431 | 10.52 | 79.6 | >20.000 | 22.6 | | |
| 4241660 | 10.531 | 111.4 | >20.000 | 48.3 | | |
| 24814623 | 10.55 | 57.7 | >20.000 | 62.3 | | |
| 24831744 | 10.58 | 97.1 | >20.000 | 24.8 | | |
| 26661768 | 10.61 | 79.7 | >20.000 | 22.1 | | |
| 4246752 | 10.794 | 105.2 | >20.000 | 29.5 | | |
| 26725324 | 10.82 | 71.9 | >20.000 | 10.2 | | |
| 24831578 | 10.88 | 76.7 | >20.000 | 43.1 | | |
| 24788894 | 10.88 | 75.1 | >20.000 | 32.0 | | |
| 26661814 | 10.92 | 78.1 | >20.000 | 48.8 | | |
| 24780006 | 10.98 | 65.0 | >20.000 | 19.4 | | |
| 26657833 | 11.19 | 71.1 | >20.000 | 31.6 | | |
| 24783509 | 11.21 | 67.2 | >20.000 | 37.2 | | |
| 26725790 | 11.24 | 78.3 | >20.000 | 31.2 | | |
| 24784595 | 11.32 | 61.2 | >20.000 | 44.2 | | |
| 26658134 | 11.33 | 78.6 | >20.000 | 38.5 | | |
| 24794744 | 11.41 | 70.9 | >20.000 | 5.0 | | |
| 7969685 | 11.56 | 72.6 | >20.000 | 15.7 | | |
| 24801477 | 11.63 | 65.1 | >20.000 | 11.2 | | |
| 26666547 | 11.72 | 69.5 | >20.000 | 52.4 | | |
| 17507998 | 11.826 | 33.2 | >20.000 | 15.3 | | |
| 24784703 | 11.87 | 81.2 | >20.000 | 39.5 | | |
| 24803541 | 11.91 | 76.1 | >20.000 | 28.0 | | |
| 26660395 | 12.06 | 70.3 | >20.000 | 20.9 | | |
| 4246909 | 12.161 | 84.0 | >20.000 | 21.7 | | |
| 24780599 | 12.25 | 72.7 | >20.000 | 17.1 | | |
| 24785789 | 12.27 | 74.7 | >20.000 | 19.2 | | |
| 17504441 | 12.316 | 93.5 | >20.000 | 44.9 | | |
| 26666944 | 12.32 | 73.4 | >20.000 | 13.2 | | |
| 24833424 | 12.34 | 76.3 | >20.000 | 28.5 | | |
| 3717484 | 12.38 | 65.7 | >20.000 | 15.0 | | |
| 24832104 | 12.39 | 64.7 | >20.000 | 39.0 | | |
| 24816898 | 12.40 | 68.8 | >20.000 | 53.0 | | |
| 17388136 | 12.492 | 92.3 | >20.000 | 33.8 | | |
| 26664211 | 12.56 | 67.4 | >20.000 | 36.7 | | |
| 17401805 | 12.675 | 120.1 | >20.000 | 16.2 | | |
| 14724731 | 12.746 | 91.6 | >20.000 | 23.7 | | |
| 4263867 | 12.860 | 95.4 | >20.000 | 33.2 | | |
| 26670025 | 12.88 | 74.3 | >20.000 | 20.4 | | |
| 26670288 | 12.90 | 65.7 | >20.000 | 24.3 | | |
| 17506409 | 12.95 | 68.3 | >20.000 | 13.8 | | |
| 17413118 | 12.996 | 76.3 | >20.000 | 43.9 | | |
| 26731880 | 13.18 | 78.9 | >20.000 | 57.2 | | |
| 24841386 | 13.20 | 69.7 | >20.000 | 44.2 | | |
| 17412131 | 13.335 | 67.2 | >20.000 | 34.0 | | |
| 4260860 | 13.404 | 73.9 | >20.000 | 56.9 | | |
| 14743896 | 13.586 | 100.1 | >20.000 | 32.3 | | |
| 26658010 | 13.60 | 73.1 | >20.000 | 0.4 | | |

TABLE 3-continued

Identification of hit compounds that selectively inhibit the Nef-Hck complex.

| | Hck + Nef | | Hck Alone | | |
|---|---|---|---|---|---|
| SID | $IC_{50}$ µM | % Inhib (20 µM) | $IC_{50}$ µM | % Inhib (20 µM) | $IC_{50}$ Ratio Alias |
| 24780013 | 13.66 | 65.7 | >20.000 | 15.0 | |
| 26670577 | 13.74 | 70.5 | >20.000 | 20.3 | |
| 24823295 | 13.82 | 60.4 | >20.000 | 44.3 | |
| 24841208 | 13.95 | 63.5 | >20.000 | 38.7 | |
| 24801954 | 13.97 | 73.9 | >20.000 | 0.1 | |
| 24815262 | 14.09 | 100.6 | >20.000 | 11.4 | |
| 24781734 | 14.10 | 68.9 | >20.000 | 27.0 | |
| 26725326 | 14.14 | 64.3 | >20.000 | 16.0 | |
| 24841384 | 14.21 | 67.9 | >20.000 | 26.6 | |
| 14744346 | 14.279 | 71.3 | >20.000 | 27.3 | |
| 26660974 | 14.40 | 64.7 | >20.000 | 32.7 | |
| 24840637 | 14.58 | 66.7 | >20.000 | 6.8 | |
| 26731792 | 14.77 | 56.4 | >20.000 | 29.4 | |
| 24816953 | 14.83 | 56.0 | >20.000 | 47.3 | |
| 24784793 | 14.87 | 67.3 | >20.000 | 25.2 | |
| 26731393 | 14.98 | 53.6 | >20.000 | 37.7 | |
| 24823138 | 15.01 | 56.1 | >20.000 | 10.1 | |
| 24781414 | 15.09 | 61.7 | >20.000 | 25.0 | |
| 24834299 | 15.17 | 66.8 | >20.000 | 18.1 | |
| 24782282 | 15.30 | 65.1 | >20.000 | 22.7 | |
| 17401701 | 15.391 | 81.0 | >20.000 | 31.6 | |
| 17434007 | 15.921 | 72.5 | >20.000 | 40.2 | |
| 26725715 | 16.03 | 46.0 | >20.000 | 34.8 | |
| 26725815 | 16.14 | 53.4 | >20.000 | 48.5 | |
| 865767 | 16.269 | 61.5 | >20.000 | 58.4 | |
| 24791268 | 16.50 | 64.9 | >20.000 | 11.1 | |
| 22401755 | 16.59 | 66.0 | >20.000 | −34.2 | |
| 26663167 | 16.59 | 54.9 | >20.000 | 28.5 | |
| 24814480 | 16.80 | 55.3 | >20.000 | 49.1 | |
| 26724296 | 16.89 | 68.6 | >20.000 | 5.6 | |
| 24797840 | 16.96 | 54.7 | >20.000 | 5.0 | |
| 26670790 | 17.08 | 53.1 | >20.000 | 28.6 | |
| 24840512 | 17.16 | 56.3 | >20.000 | 26.3 | |
| 22401274 | 17.321 | 50.2 | >20.000 | 32.6 | |
| 24802850 | 17.46 | 55.1 | >20.000 | 13.8 | |
| 24839345 | 17.56 | 59.1 | >20.000 | 22.3 | |
| 24790187 | 17.81 | 50.7 | >20.000 | 41.0 | |
| 26662906 | 17.82 | 58.6 | >20.000 | 12.7 | |
| 24803697 | 18.23 | 52.0 | >20.000 | 17.1 | |
| 24794748 | 18.46 | 51.3 | >20.000 | 6.5 | |
| 26666360 | 18.75 | 70.2 | >20.000 | 12.4 | |
| 24831307 | 18.82 | 54.8 | >20.000 | 12.6 | |
| 24792399 | 18.92 | 52.0 | >20.000 | 20.0 | |
| 26725323 | 19.10 | 76.5 | >20.000 | 18.4 | |
| 26658738 | 19.12 | 53.4 | >20.000 | 2.7 | |
| 4260983 | 19.212 | 53.3 | >20.000 | 27.3 | |
| 3713339 | >20.000 | −3.0 | >20.000 | 25.9 | |
| 4245856 | >20.000 | 37.7 | 16.50 | 56.9 | |
| 4255480 | >20.000 | −2.7 | 16.92 | 59.5 | |
| 14737293 | >20.000 | 21.3 | >20.000 | 18.4 | |
| 14742743 | >20.000 | 41.8 | 9.64 | 67.2 | |
| 17401962 | >20.000 | −4.0 | >20.000 | 44.5 | |
| 17409038 | >20.000 | 27.7 | >20.000 | 42.7 | |
| 17512740 | >20.000 | 43.6 | >20.000 | 19.8 | |
| 22400409 | >20.000 | 24.2 | 19.28 | 59.3 | |
| 22403716 | >20.000 | 34.0 | >20.000 | 24.8 | |
| 24780863 | >20.000 | 38.9 | >20.000 | 26.0 | |
| 24789917 | >20.000 | 48.0 | >20.000 | 6.7 | |
| 24790095 | >20.000 | 43.4 | >20.000 | 12.3 | |
| 24791773 | >20.000 | 28.6 | >20.000 | 34.6 | |
| 24796961 | >20.000 | 79.8 | >20.000 | 7.1 | |
| 24797629 | >20.000 | 86.6 | >20.000 | 10.0 | |
| 24816869 | >20.000 | 54.1 | >20.000 | 33.8 | |
| 24820340 | >20.000 | 32.1 | >20.000 | 15.4 | |
| 24823589 | >20.000 | 38.5 | >20.000 | 5.4 | |
| 26657630 | >20.000 | 52.7 | >20.000 | 28.5 | |
| 26661385 | >20.000 | 47.2 | >20.000 | 51.1 | |
| 26671555 | >20.000 | 41.7 | >20.000 | −16.5 | |

Example 3

Figure 5:
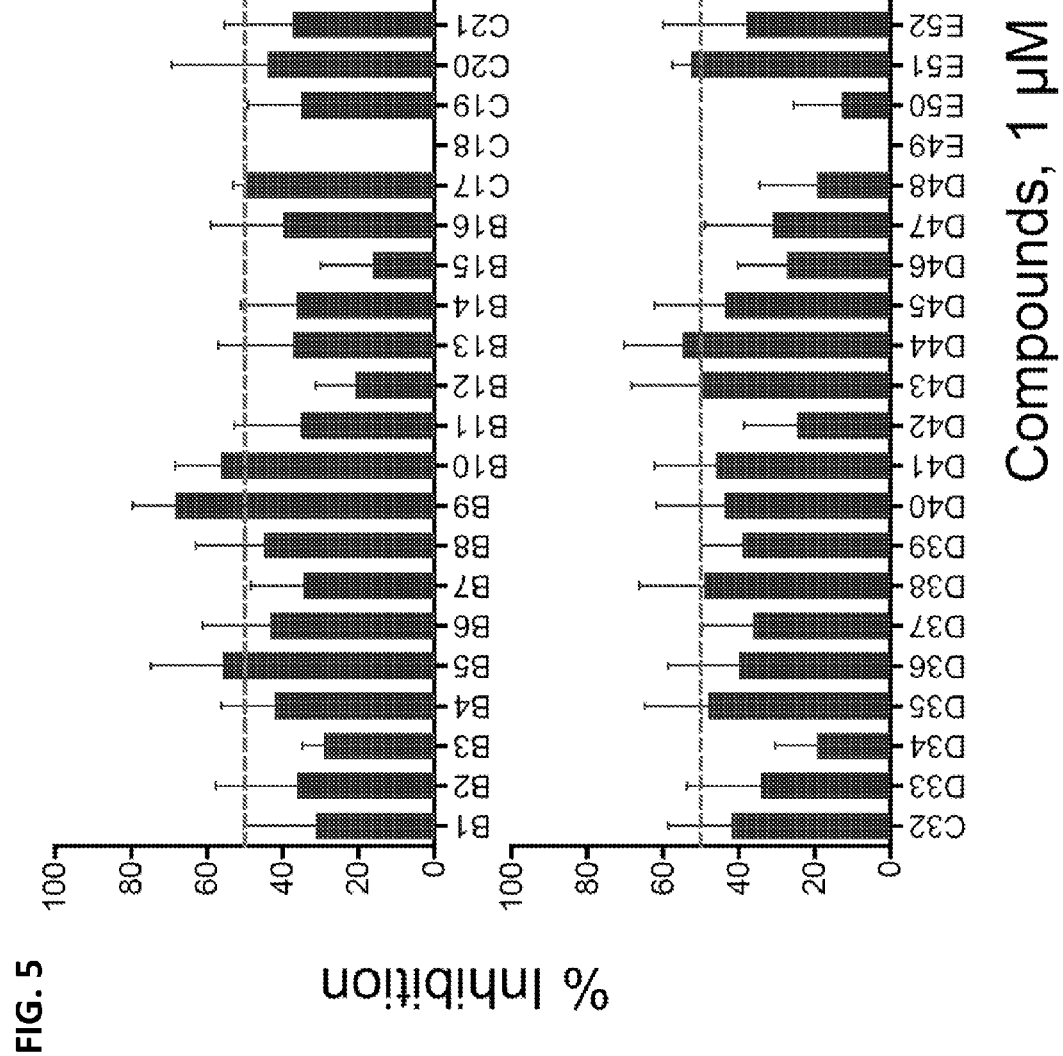
FIG. 5 is a bar graph illustrating results obtained from analyzing the ability of various compounds of the MLSCN library to inhibit HIV replication in CEM-T4 cells. Data are expressed as the mean percent inhibition as compared to control cultures incubated with the carrier solvent (DMSO) ±S.E.M. (n=4).
Figure 6:
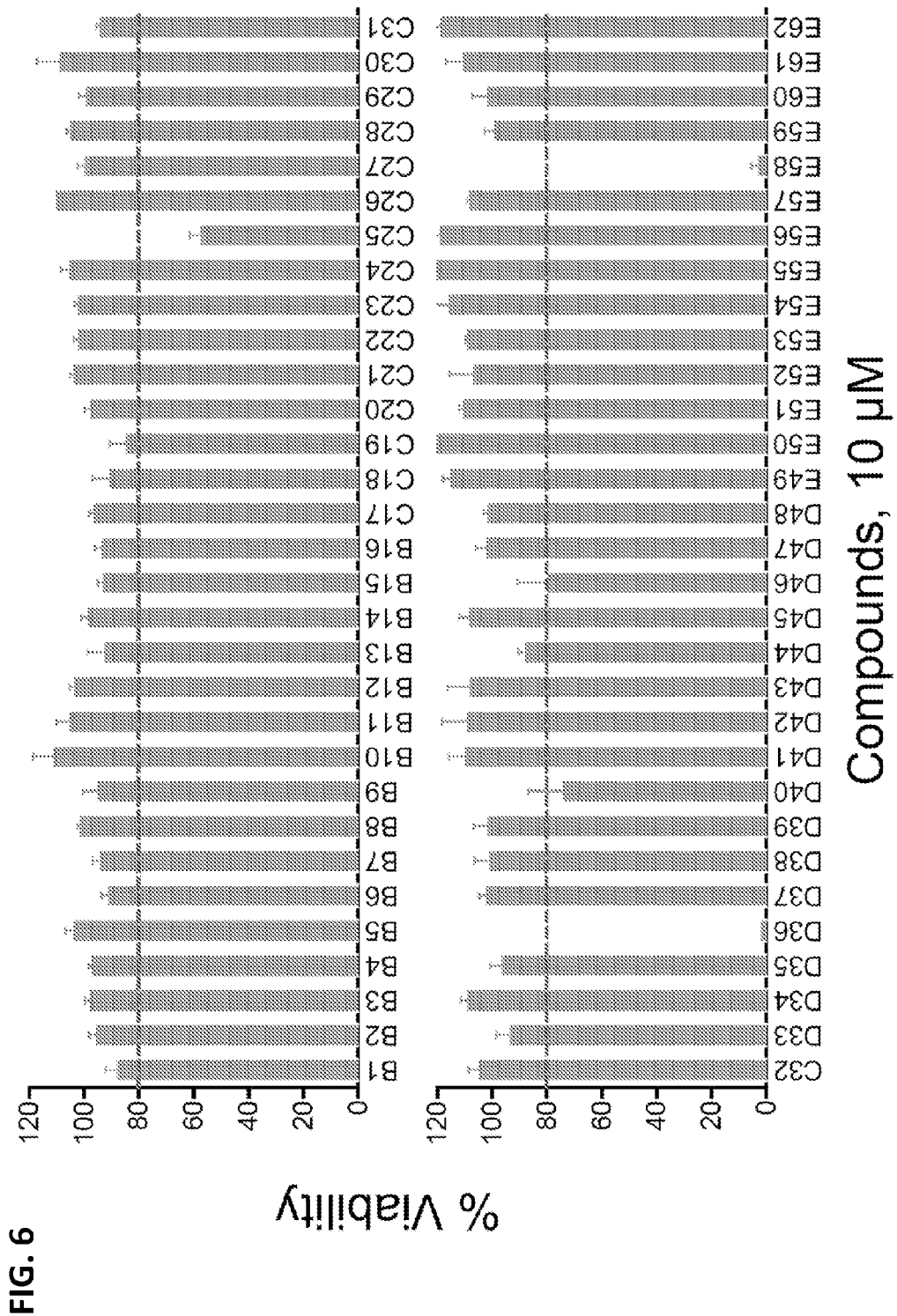
FIG. 6 is a bar graph illustrating the cytotoxicity of various compounds of the MLSCN library after being incubated for 72 hours with CEM-T4 cells at concentrations of 10 μM.

The compounds from Example 2 were then assayed for anti-HIV activity (FIG. 3) as well as cytotoxicity in U87MG astroglioma cells (FIG. 4) and CEM-T4 lymphoblasts (anti-HIV activity—FIG. 5, and cytotoxicity—FIG. 6). It is known in the art that HIV replication is dependent upon Nef in both of these cell lines. In U87MG cells, 24 of the 62 compounds (39%) showed more than 50% inhibition of HIV-1 replication at a concentration of 1 µM without toxicity. The response rate in CEM-T4 cells was somewhat lower, with 11 of the 62 hit compounds (18%) blocking replication by more than 50% under the same conditions. Five compounds inhibited HIV-1 replication in both cell lines with low to sub-micromolar potency and without appreciable cytotoxicity. The structures of these compounds, their $IC_{50}$ values for inhibition of the Hck:Nef complex vs. Hck alone, as well as their effects on HIV-1 replication are shown in FIG. 7.

Example 4

The impact of these five compounds on infectivity was also determined using the TZM-b1 reporter cell line. In this system, infectivity is measured as stimulation of luciferase reporter gene expression driven by the HIV-1 LTR in response to infection with HIV-1, and this effect is enhanced by HIV-1 Nef. As shown in FIG. 9, four of the five compounds suppressed Nef-dependent enhancement of HIV-1 infectivity.

Example 5

To investigate whether the antiretroviral activity of B9 was dependent upon the expression of Nef, the impact of B9 on replication of wild-type and Nef-defective HIV-1 was compared in CEM-T4 cells. As shown in FIG. 11, B9 blocked wild-type HIV-1 replication with an $IC_{50}$ value in the 100-300 nM range, while replication of Nef-defective HIV-1 was unaffected at the highest concentration tested (3.0 µM). B9 also inhibited Nef-mediated enhancement of HIV-1 infectivity in a concentration-dependent manner in the reporter cell line, TZM-b1 (FIG. 12). Together, these results strongly support a Nef-dependent antiretroviral mechanism of action for embodiments of the disclosed compound.

Example 6

It was next determined whether B9 is broadly active against the diverse Nef alleles that comprise the majority of HIV-1 M-group clades. For these embodiments, a set of recombinant HIV-1 NL4-3 chimeras in which the NL4-3 Nef sequence is replaced with representative Nef sequences derived from the M-group HIV-1 subtypes A1, A2, B, C, F1, F2, G, H, J, K, as well as the laboratory strain, SF2 were used. As shown in FIG. 13, B9 inhibited the replication of all eleven HIV-1 Nef chimeras with an $IC_{50}$ value of ~300 nM in CEM-T4 cells, demonstrating that the compound is broadly active against HIV replication supported by a wide range of HIV-1 Nef proteins. As observed previously, the compound had no effect on the replication of Nef-defective HIV replication in this experiment.

Example 7

In particular disclosed embodiments, it was determined whether the inhibition of Nef-dependent kinase activation observed with B9 in vitro could also be observed in inhibitor-treated cells under conditions of viral replication block. For these embodiments, CEM-T4 cells were infected with wild-type HIV-1 NL4-3, the eleven Nef chimeras, and the Nef-defective mutant in the presence or absence of B9. Endogenous SFK activity was assessed in infected cell lysates by immunoblotting with an antibody that recognizes the phosphotyrosine residue in the activation loop of active SFKs (pY418). As shown in FIG. 14, wild-type but not Nef-defective HIV infection stimulated endogenous SFK activation. B9 treatment completely inhibited Nef-dependent SFK activation at a concentration of 1.0 µM. These results provide important evidence that B9 blocks Nef-mediated SFK activation in HIV-infected cells, which may represent one part of its antiretroviral mechanism of action.

Example 8

To determine whether B9 binds directly to Nef, SPR studies using immobilized Nef and a range of compound concentrations were conducted. As shown in FIG. 17, B9 interaction with Nef was readily detected by this approach, demonstrating saturable binding at each B9 concentration tested. The resulting SPR sensorgrams fit a heterogenous ligand-parallel reaction model disclosed by Kuroki and Maendaka (where Nef is 'ligand'), which yielded Kd values of 860±58 nM and 1.72±0.23 nM. These binding data are consistent with the docking results, which predicted two binding sites (FIG. 15). The SPR data were also consistent with a two-state model, in which B9 binding to a lower affinity site is predicted to induce a conformational change to a higher affinity binding site (FIG. 18). The overall Kd value resulting from this two-state analysis was 1.79±0.11 nM, which is in close agreement with the heterogeneous ligand model.

Example 9

In addition to HIV-1 Nef, as disclosed herein, docking studies of B9 with an X-ray crystal structure of SIV Nef were also performed. In this structure, SIV Nef also packs as a dimer, although the nature of the dimer interface is distinct from that of HIV-1 Nef (FIG. 21). B9 was predicted to dock to an energetically favorable site formed by the SIV Nef dimer interface, as indicated by the information in Table 1.

Example 10

Particular disclosed embodiments concern determining the effect of the compound on SIV replication and infectivity. CEM-174 cells were infected with the pathogenic SIV quasispecies ΔB670 over a range of B9 concentrations, and assayed for SIV replication as p27 Gag release. As shown in FIG. 22, B9 blocked SIV replication with an $IC_{50}$ value of about 1.0 µM. The impact of B9 on SIV ΔB670 infectivity was also evaluated using the TZM-b1 reporter cell line described above for HIV. As shown in FIG. 23, B9 blocked SIV infectivity with an $IC_{50}$ value of about 3 µM. These results provide further support for the idea that compounds targeting the Nef dimer may be broadly effective as Nef antagonists. Previous studies have shown that the Nef dimerization interface is very sensitive to mutagenesis, with single amino acid substitutions in this region compromising Nef functions related to receptor downregulation and HIV-1 replication. These studies suggest that small molecules such as B9, which bind to the dimer interface and influence the conformation or stability of the dimer, may have a major impact on Nef function.

Example 11

In particular disclosed embodiments, a bimolecular fluorescence complementation (BiFC) assay developed for Nef was used to analyze the effect of the compound on Nef dimerization. In this assay, Nef is expressed as a pair of fusion proteins with non-fluorescent fragments of YFP in 293T cells. Nef dimerization juxtaposes the YFP fragments, which then refold to form the fluorescent YFP structure. Nef dimerization requires four conserved hydrophobic side chains that lock together to form a helical interface (Ile109, Leu112, Tyr115, Phe121; FIG. 24). Replacement of these residues with aspartic acid (Nef-4D mutant) results in a dramatic loss of the Nef-BiFC signal, providing a negative control for the assay. To test the effect of B9 on Nef dimerization by BiFC, 293T cells were transfected with wild-type Nef-BiFC fusion proteins and incubated with B9 over a range of concentrations (1-6 µM). As shown in FIG. 25, B9 treatment resulted in a concentration-dependent loss in the Nef BiFC signal, with suppression more dramatic than that observed with the Nef-4D mutant at the highest concentration tested (6 µM). All cultures were immunostained with a Nef antibody to establish that B9 interferes with dimerization rather than Nef protein expression. These data support the idea that B9 inhibits Nef dimerization as part of its mechanism of action.

Example 12

In certain disclosed embodiments, it was determined whether the dimerization interface contributes to Hck activation in the assay disclosed herein. The dimerization-defective Nef-4D mutant was expressed and purified in recombinant form, and tested for its ability to activate Hck in the Z'Lyte assay. FIG. 26 shows that Nef-4D is completely defective for Hck activation in vitro. These results support the idea that B9 inhibits Hck activation by binding to the Nef dimerization interface, thereby preventing Nef dimerization and juxtaposition of associated Hck kinase domains.

Example 13

In this embodiment, analog B9 was demonstrated to be capable of reversing Nef-induced MHC-I downregulation in CEM T-cells. CEM-GFP cells were treated for 4 hrs with compounds or DMSO (control), then infected with 100 pg/ml HIV-1 WT NL43 or 500 pg/ml ΔNef-NL43.

After 8 days, when cells were observed to be >80% GFP-positive, $5 \times 10^5$ cells were fixed with 2% PFA and stained with MHC-I-PE antibody for analysis via flow cytometry.

Figure 32A:
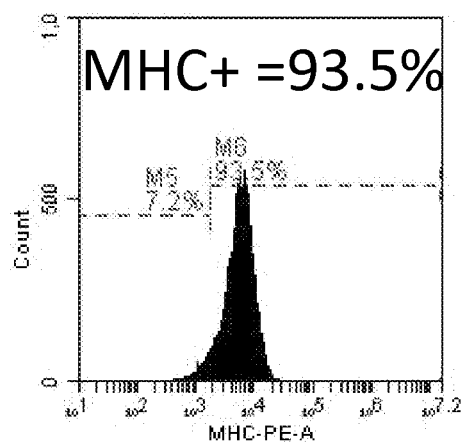
FIGS. 32A-32E are flow cell cytometry diagrams showing the percent of cells positive for cell surface MHC-I. Nef downregulates MHC-I and this process is inhibited by the exemplary embodiments of the compound disclosed herein.
Figure 32B:
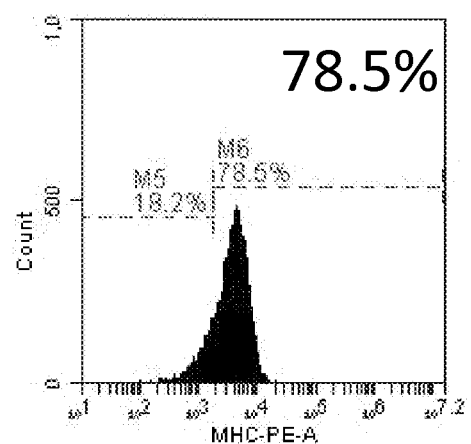
Figure 32C:
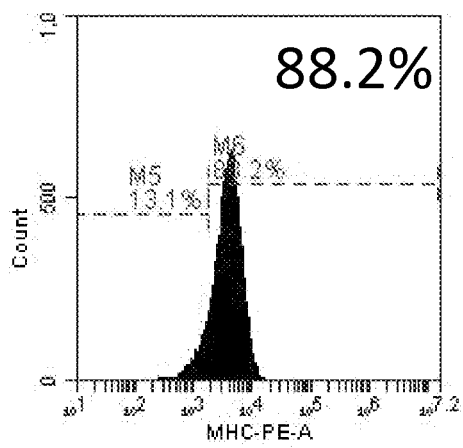
Figure 32D:
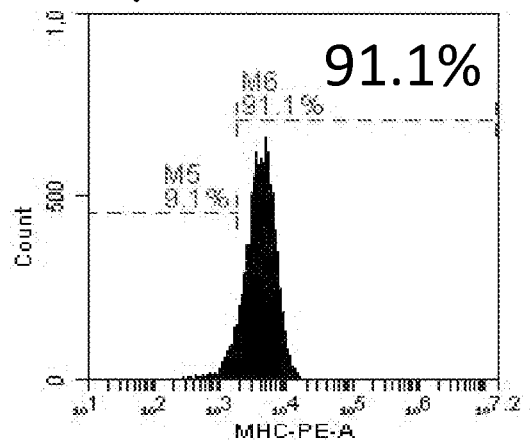
Figure 32E:
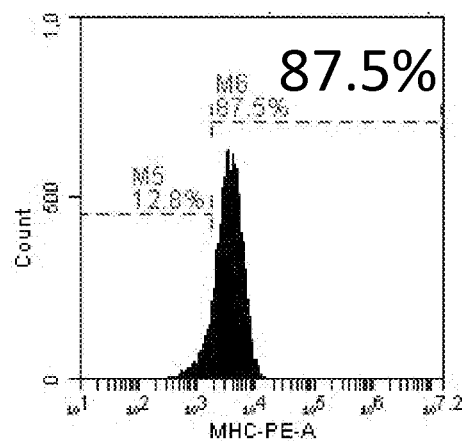

Percentages on the flow diagrams (FIGS. 32A-32E) show percent of cells positive for MHC-I. As illustrated in these FIGS., B9 (FIG. 32E) and the non-azo analog JZ-97-2-1 (FIG. 32D) both reverse Nef-mediated MHC-I downregulation to the same extent observed in cells infected with Nef-defective HIV-1.

Example 14

In this embodiment, analog B9 was demonstrated to be capable of reversing Nef-induced CD4 downregulation in CEM T-cells. CEM-GFP cells were treated for 4 hrs with compounds or DMSO (control), then infected with 100 pg/ml HIV-1 WT NL43 or 500 pg/ml ΔNef-NL43.

After 8 days, when cells were observed to be >80% GFP-positive, $5 \times 10^5$ cells were fixed with 2% PFA and stained with CD4-APC antibody for analysis via flow cytometry.

Figure 33A:
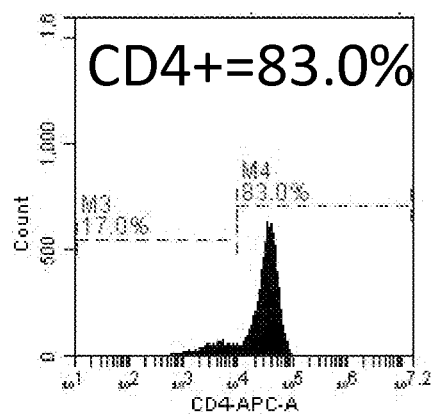
FIGS. 33A-33E are flow cell cytometry diagrams showing the percent of cells positive for cell-surface CD4. Nef downregulates CD4 and this process is inhibited by the exemplary embodiments of the compound disclosed herein.
Figure 33B:
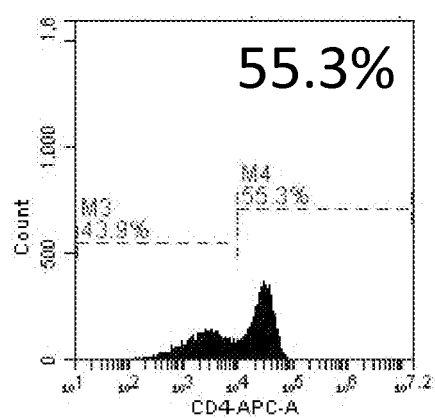
Figure 33C:
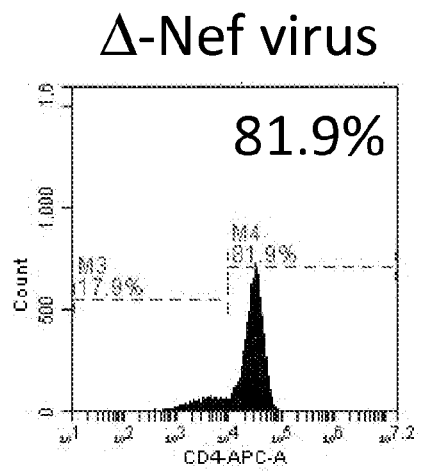
Figure 33D:
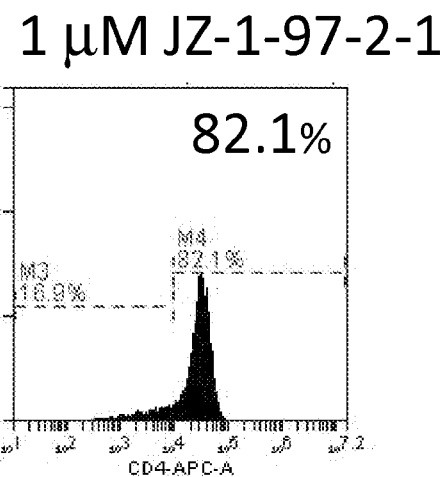
Figure 33E:
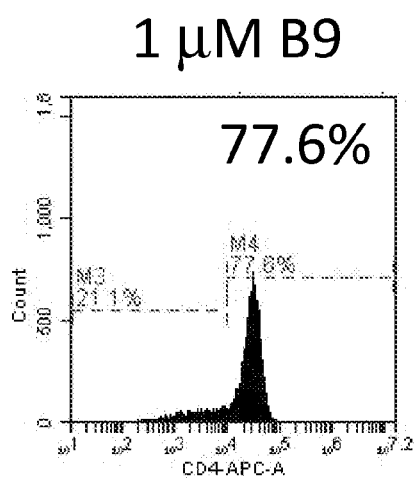

Percentages on the flow diagrams (FIGS. 33A-33E) show percent of cells positive for CD4. As illustrated in these FIGS., B9 (FIG. 33E) and the non-azo analog JZ-97-2-1 (FIG. 33D) both reverse Nef-mediated CD4 downregulation to the same extent observed in cells infected with Nef-defective HIV-1.

Example 15

In this embodiment, pharmacokinetic assessment was performed with the Nef antagonist B9 and two non-azo analogs (JZ-1-96-2-1 and JZ-1-97-2-1) in C3H mice. Replacement of the azo linker in B9 with a one- or two-carbon linker (JZ-1-97-2-1 and JZ-1-96-2-1, respectively) greatly enhanced oral bioavailability (represented as % F in Table 4).

TABLE 4

Preliminary pharmacokinetics of small molecule Nef inhibitors.

| Compound | Linker | Route | Dose (mg/kg) | $T_{1/2}$ (h) | % F |
|---|---|---|---|---|---|
| B9 | —N=N— | i.v. | 2 | 2.13 | |
| | | p.o. | 10 | | 2 |
| JZ-1-96-2-1 | —C—C— | i.v. | 2 | 1.53 | |
| | | p.o. | 10 | | 85 |
| JZ-1-97-2-1 | —C— | i.v. | 2 | 1.66 | |
| | | p.o. | 10 | | 57 |

Table 5, below provides infectivity inhibition data (% Inhibition in TZM-b1 reporter cells) of exemplary compounds disclosed herein, as well as replication inhibition data (% Inhibition in U87MG cells).

TABLE 5

Inhibition of Nef-dependent HIV-1 infectivity and replication

| ANALOG | INFECTIVITY @ 3 μM % Inhibition vs. DMSO control | REPLICATION @ 3 μM % Inhibition vs. DMSO control |
|---|---|---|
| Delta Nef | 75.3 | 89.7 |
| B9 | 37.0 | 47.4 |
| JV-1-79 | Toxic | Toxic |
| JV-1-75-2A | 78.9 | 34.9 |
| JZ-1-96-2-1 | 59.5 | Toxic |
| JZ-1-97-2-1 | 56.6 | 51.6 |
| JV-2-14 | 54.7 | N/A |
| JV-2-12 | 41.7 | N/A |
| JV-1-80 | Toxic | Toxic |
| KM-1-46 | 37.2 | 43.6 |
| JV-1-74-2 | 36.7 | 46.8 |
| PCI-1-50 | 35.3 | N/A |
| JZ-1-178 | 34.7 | 0 |
| JZ-1-50 | 28.9 | N/A |
| JV-1-89 | 28.0 | 56.1 |
| JZ-1-64 | 26.5 | N/A |
| PCI-1-52 | 26.1 | N/A |
| PCI-1-48 | 25.8 | 0 |
| PCI-1-55 | 25.3 | 0 |
| JV-1-71-1 | 25.2 | N/A |
| PCI-1-23 | 24.3 | 0 |
| PCI-1-06 | 23.0 | N/A |
| JV-1-81 | 19.7 | N/A |
| JZ-1-107 | 19.7 | 0 |
| KM-1-48 | 19.3 | N/A |

TABLE 5-continued

Inhibition of Nef-dependent HIV-1 infectivity and replication

| ANALOG | INFECTIVITY @ 3 μM % Inhibition vs. DMSO control | REPLICATION @ 3 μM % Inhibition vs. DMSO control |
|---|---|---|
| JZ-2-21 | 16.7 | N/A |
| PCI-1-25 | 16.3 | N/A |
| PCI-1-43 | 15.3 | 0 |
| PCI-1-29 | 12.9 | N/A |
| JZ-1-97-2-2 | 12.7 | 0 |
| JV-1-96 | 11.0 | Toxic |
| JZ-1-135-1 | 9.5 | 54.1 |
| JZ-1-62 | 9.3 | N/A |
| PCI-1-45 | 8.3 | 0 |
| JZ-1-176 | 7.7 | N/A |
| JZ-1-58-3 | 7.3 | N/A |
| PCI-1-56 | 5.6 | 0 |
| JZ-1-106 | 3.5 | 0 |
| JZ-1-110-1 | 3.3 | 0 |
| PCI-1-53 | 3.2 | 0 |
| JZ-1-62-2-1 | 3.1 | N/A |
| JV-2-10 | 3.0 | N/A |
| JV-2-13 | 1.7 | N/A |
| JZ-1-58-2 | 1.7 | N/A |
| PCI-1-30 | 0.6 | 0 |
| DD-1-21 | 0.0 | N/A |
| DD-1-22 | 0.0 | N/A |
| DD-1-26 | 0.0 | N/A |
| DD-1-27 | 0.0 | N/A |
| DD-1-30 | 0.0 | N/A |
| DD-1-33 | N/A | N/A |
| DD-1-34 | N/A | N/A |
| EAF-1-21 | 0.0 | N/A |
| EAF-1-22 | 0.0 | N/A |
| JV-1-59-1 | 0.0 | 30.1 |
| JV-1-62-2-1 | 0.0 | 53.2 |
| JV-1-62-2-2 | 0.0 | N/A |
| JV-1-67-1 | 0.0 | N/A |
| JV-1-74-1 | 0.0 | 27.8 |
| JV-1-75-1 | 0.0 | N/A |
| JV-1-87 | 0.0 | N/A |
| JV-1-94 | 0.0 | N/A |
| JV-2-16 | 0.0 | N/A |
| JV-2-19 | 0.0 | N/A |
| JV-2-3 | N/A | N/A |
| JV-2-8 | N/A | N/A |
| JV-2-9-1 | 0.0 | N/A |
| JV-97 | 0.0 | N/A |
| JZ-1-101 | 0.0 | 0 |
| JZ-1-110-2 | 0.0 | 19.3 |
| JZ-1-135-2 | 0.0 | Toxic |
| JZ-1-145-1 | 0.0 | N/A |
| JZ-1-146-1 | 0.0 | N/A |
| JZ-1-154-2-2 | 0.0 | N/A |
| JZ-1-171 | 0.0 | N/A |
| JZ-1-175 | 0.0 | N/A |
| JZ-1-177 | 0.0 | N/A |
| JZ-1-179-2 | 0.0 | N/A |
| JZ-1-180 | 0.0 | N/A |
| JZ-1-49 | 0.0 | N/A |
| JZ-1-56 | 0.0 | N/A |
| JZ-1-94 | 0.0 | N/A |
| JZ-1-96-2-2 | 0.0 | 0 |
| PCI-11-123 | 0.0 | N/A |
| PCI-II-125 | 0.0 | N/A |
| Vit-3f | 0.0 | N/A |
| Delta Nef | 75.3 | 89.7 |

In view of the many possible embodiments to which the principles of the disclosure may be applied, it should be recognized that the illustrated embodiments are only preferred examples of the disclosure and should not be taken as limiting the scope of the disclosure.

We claim:
1. A compound of Formula 2, or an ester or pharmaceutically acceptable salt thereof, for treating HIV

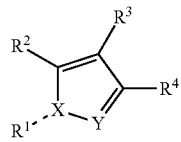

Formula 2 wherein $R^1$ is selected from hydrogen, aliphatic, aryl, heteroaliphatic, oxo, heteroaryl, or combinations thereof; $R^2$ is selected from hydroxyl, alkoxy, thiol, thioether, amine, or combinations thereof; $R^3$ is selected from $—(CH_2)_nR^6$ wherein n is zero to ten and $R^6$ is selected from aliphatic, heteroaliphatic, aryl, heteroaryl, or combinations thereof, $—N=NR^6R^7$ wherein each $R^6$ and $R^7$ independently are selected from hydrogen, aliphatic, heteroaliphatic, aryl, heteroaryl, or combinations thereof, and $—C=CR^6R^7$ wherein each $R^6$ and $R^7$ independently are selected from hydrogen, aliphatic, heteroaliphatic, aryl, heteroaryl, or combinations thereof; $R^4$ is selected from alkyl having from 5 to 10 carbon atoms, cycloalkyl, alkenyl, cycloalkenyl, alkynyl, cycloalkynyl, heteroaliphatic, aryl, heteroaryl, and combinations thereof; X is selected from nitrogen, oxygen, or carbon, $CH_2$, or $CHR^1$; Y is selected from nitrogen or CH; and provided that the compound is not (E)-4-((3-chlorophenyl)diazenyl)-5-hydroxy-3-(4-nitrophenyl)-1H-pyrazole-1-carbothioamide.

2. The compound of claim 1 wherein $R^1$ is selected from hydrogen, phenyl, pyridyl, amide, ester, carboxyl, guanidino (or derivatives thereof), thioamide, imidazoline, keto, amide, oxo, or phenyl or pyridyl substituted with one or more substituents selected from halogen, alkoxy, cyano, nitro, hydroxyl, thiol, thioether, or combinations thereof.

3. The compound of claim 1 wherein $R^2$ is selected from hydroxyl, or methoxy.

4. The compound of claim 1 wherein n is zero to five.

5. The compound of claim 1 wherein $R^6$ is aliphatic, heteroaliphatic, aryl, or heteroaryl and $R^7$ is hydrogen.

6. The compound of claim 5 wherein $R^6$ is phenyl or pyridyl and is substituted with one or more substituents selected from halogen, alkoxy, cyano, nitro, hydroxyl, thiol, thioether, or combinations thereof.

7. The compound of claim 1 wherein $R^4$ is selected from cycloalkyl, furfuryl, phenyl, substituted phenyl, pyridyl, or substituted pyridyl.

8. The compound of claim 1, wherein the compound has any one of the following formulas

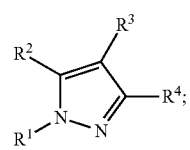

Formula 3

Formula 4

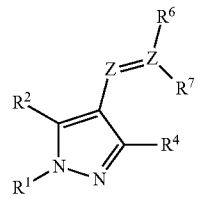

Formula 5 wherein $R^6$ is aliphatic, heteroaliphatic, aryl, heteroaryl, or combinations thereof, $R^7$ is hydrogen, and each Z independently is nitrogen, carbon, or CH.

9. The compound of claim 8 wherein each Z is the same and is nitrogen or carbon, $R^6$ is phenyl or pyridyl substituted with one or more halogen, methoxy substituents, or combinations thereof, and $R^7$ is hydrogen.

10. The compound of claim 1 wherein the compound is selected from

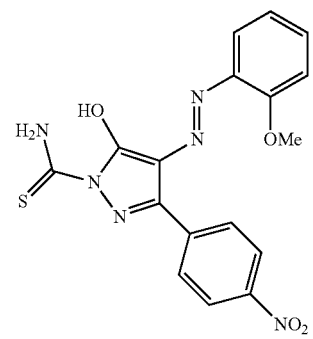

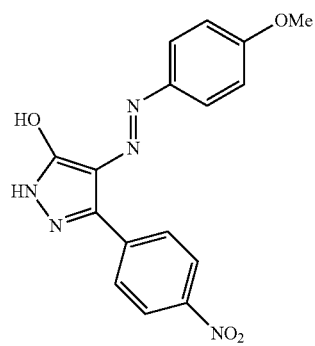

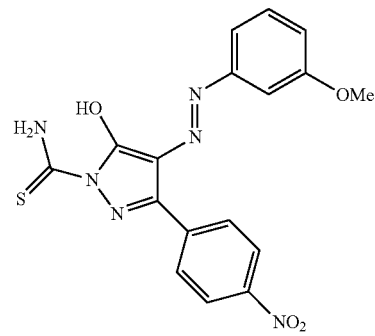

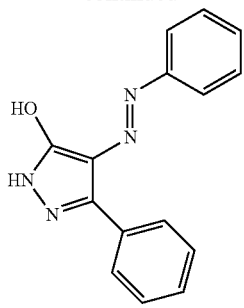
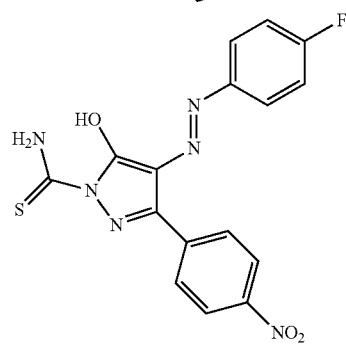
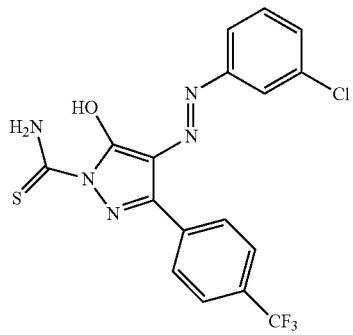
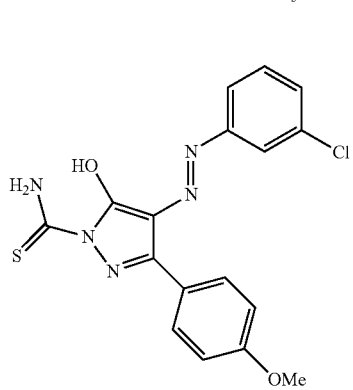
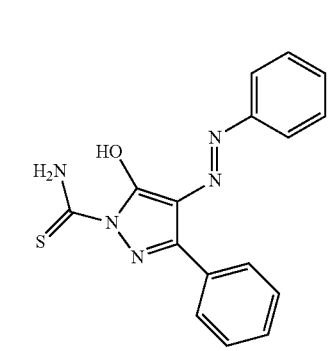
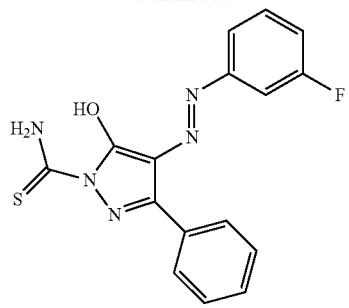
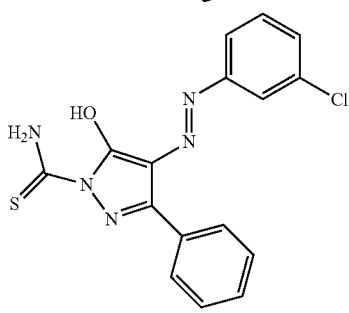
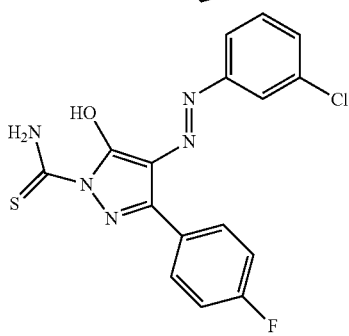
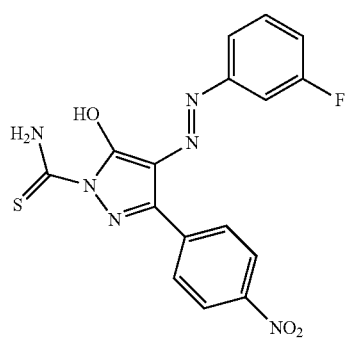
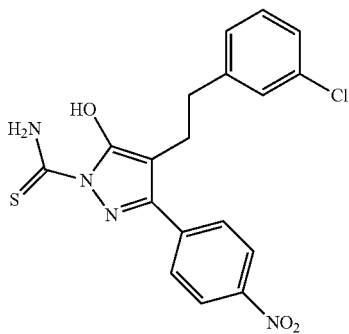

-continued
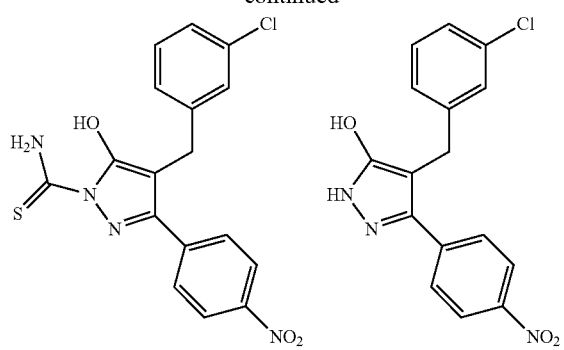
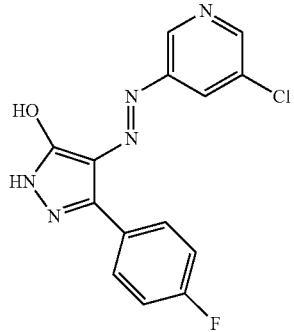
-continued
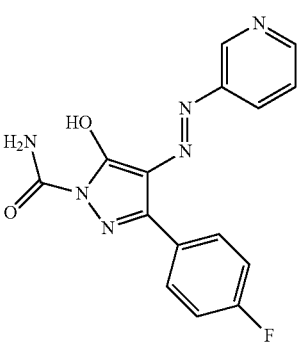
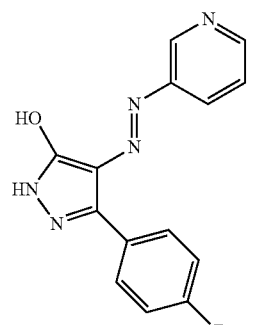
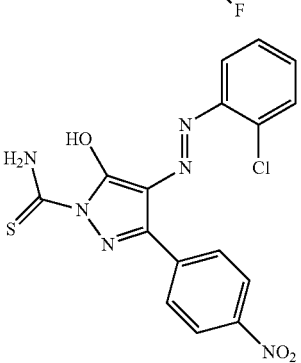
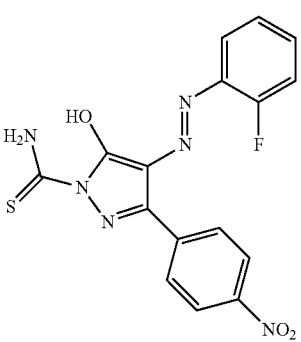

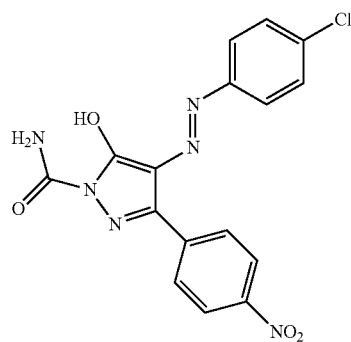
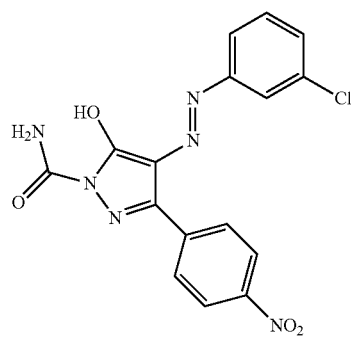
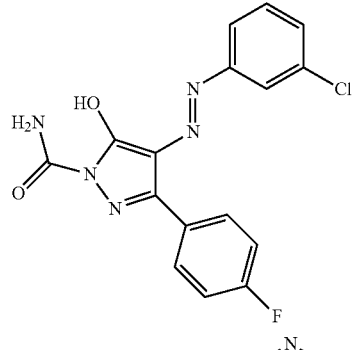
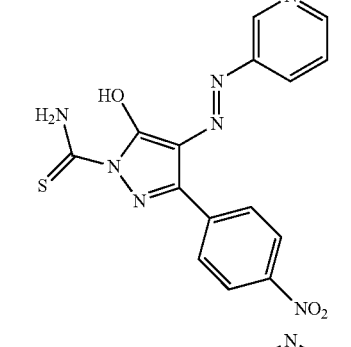
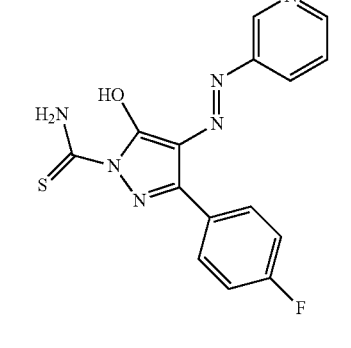
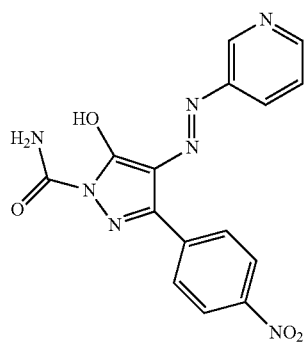
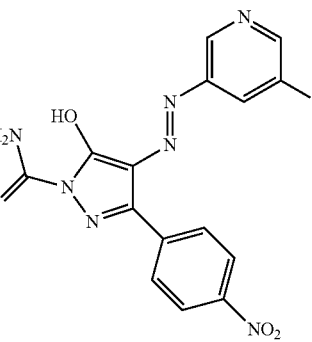
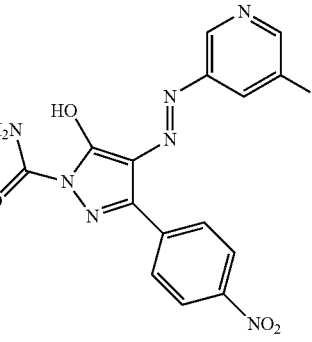
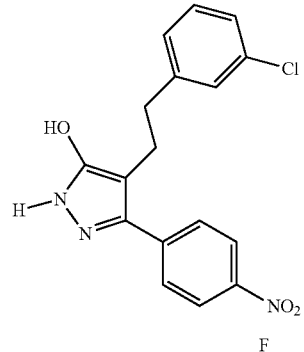
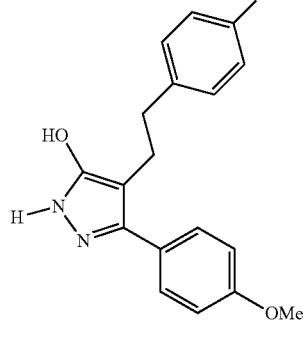

-continued
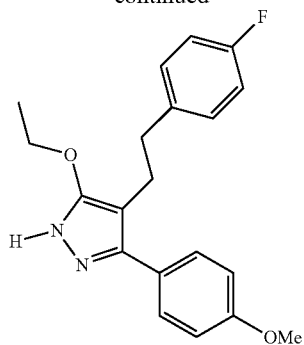
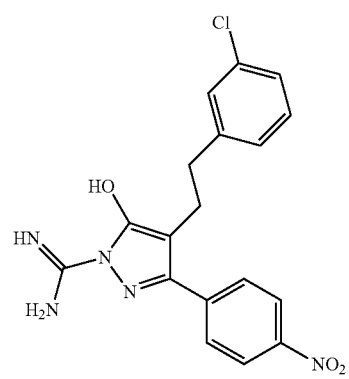
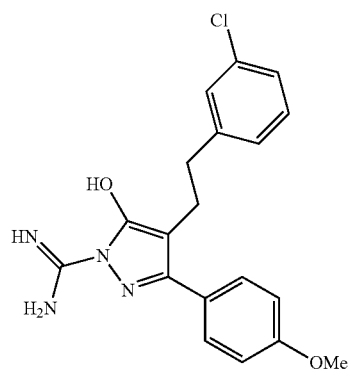
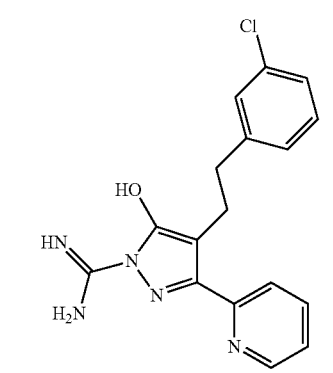
-continued
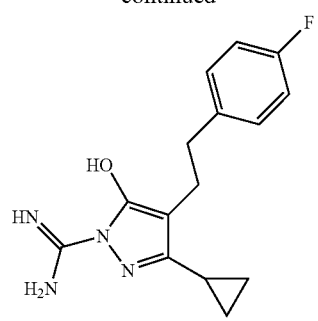
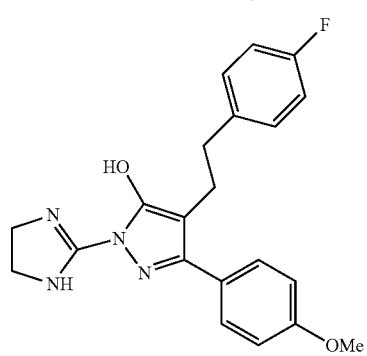
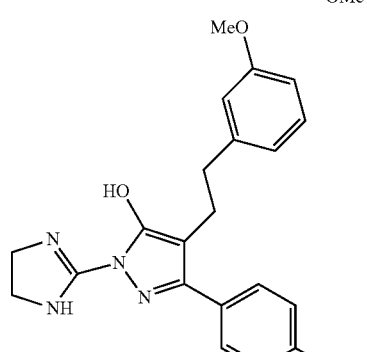
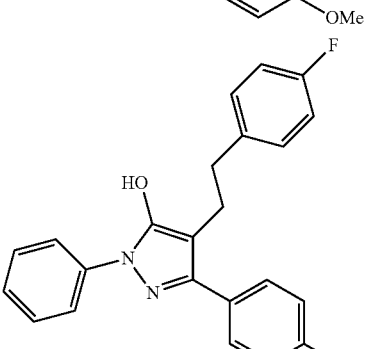
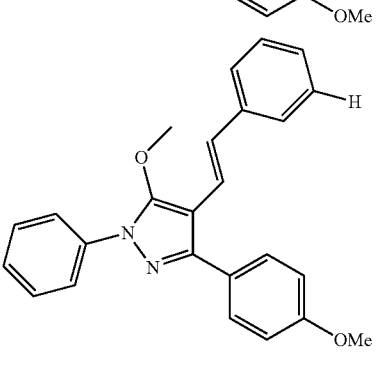

103
-continued
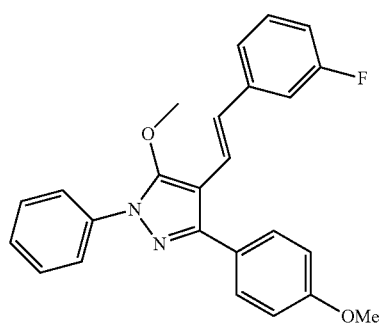
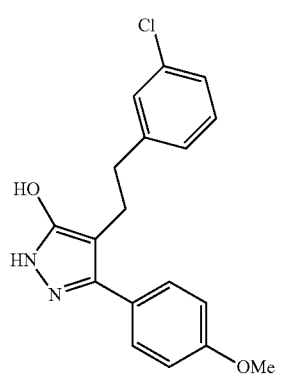
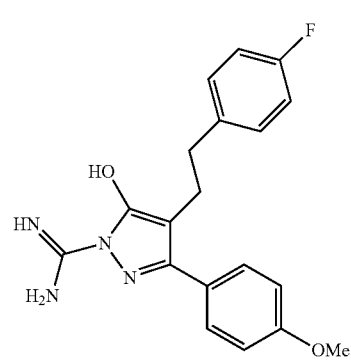
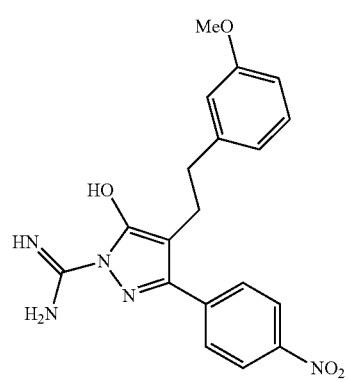
104
-continued
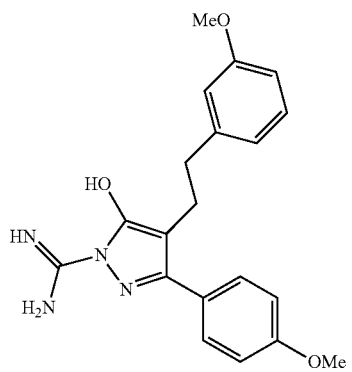
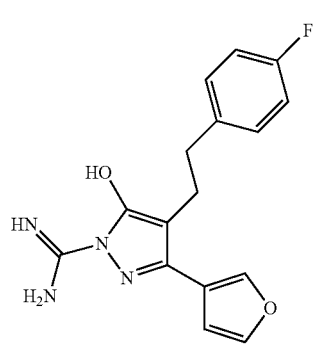
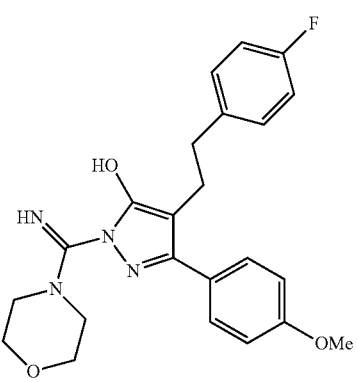
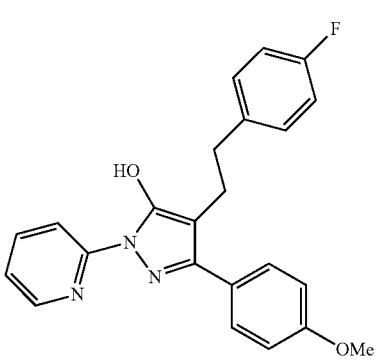

-continued

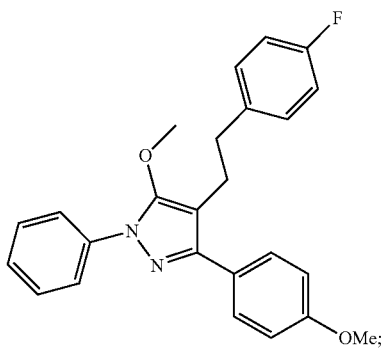

or an ester or pharmaceutically acceptable salt thereof.

11. A method for inhibiting a biological function of Nef, comprising contacting Nef with an effective amount of a compound having a Formula 2, or an ester or pharmaceutically acceptable salt thereof,

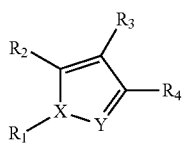

Formula 2 wherein $R^1$ is selected from hydrogen, aliphatic, aryl, heteroaliphatic, oxo, heteroaryl, or combinations thereof; $R^2$ is selected from hydrogen, aliphatic, heteroaliphatic, hydroxyl, alkoxy, thiol, thioether, amine, or combinations thereof; $R^3$ is selected from hydrogen, aliphatic, heteroaliphatic, aryl, heteroaryl, or combinations thereof; $R^4$ is selected from hydrogen, aliphatic, heteroaliphatic, aryl, heteroaryl, and combinations thereof; $R^3$ and $R^4$ can be joined together to form a 5-, 6-, 7-, or 8-membered saturated or unsaturated ring, optionally comprising one or more heteroatoms and optionally substituted with one or more substituents selected from aliphatic, heteroaliphatic, halogen, aryl, or heteroaryl; X is selected from nitrogen, oxygen, or carbon, $CH_2$, or $CHR^1$; Y is selected from nitrogen or CH.

12. The method of claim 11 wherein the compound has any one of the following formulas

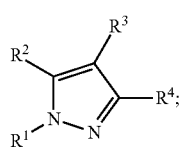

Formula 3

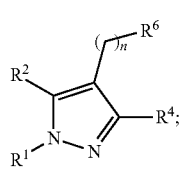

Formula 4

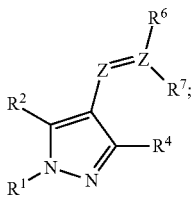

Formula 5 wherein $R^6$ is aliphatic, heteroaliphatic, aryl, heteroaryl, or combinations thereof, $R^7$ is hydrogen, and each Z independently is nitrogen or carbon.

13. The method of claim 11 wherein the compound is selected from

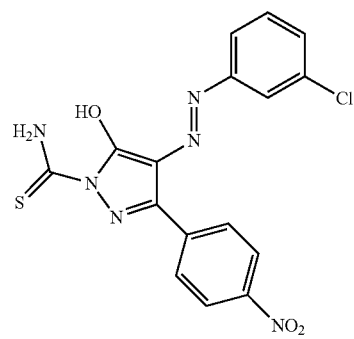

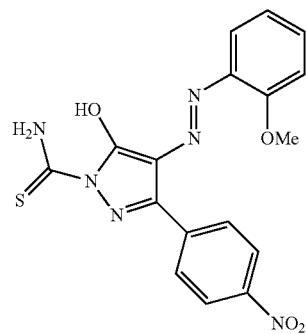

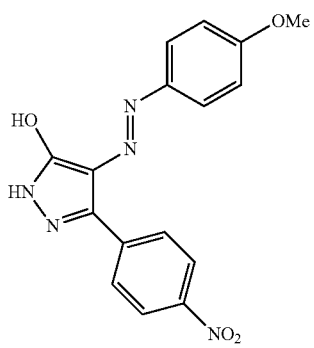

-continued
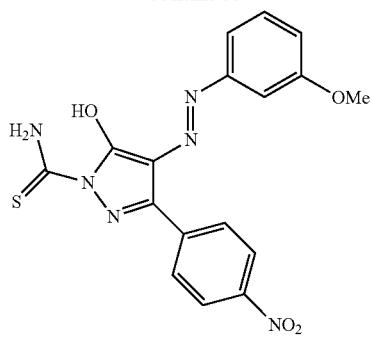
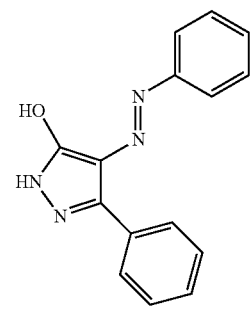
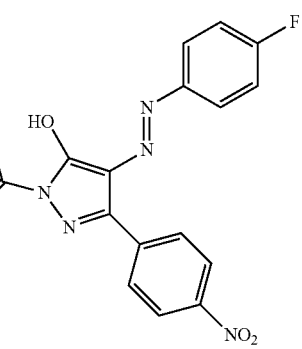
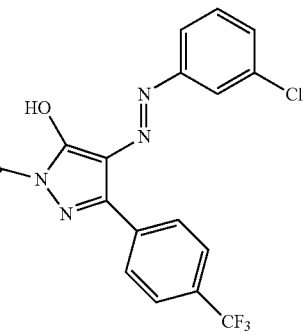
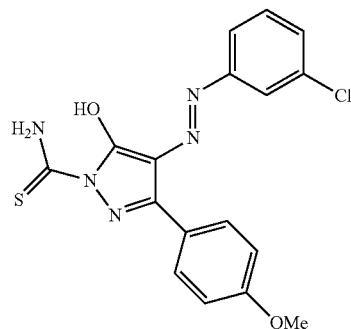
-continued
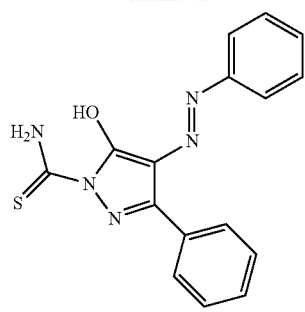
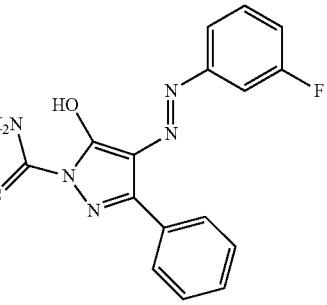
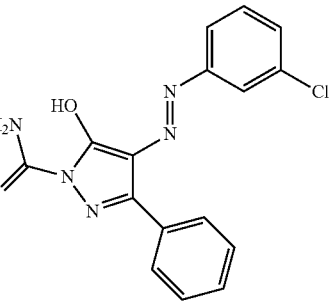
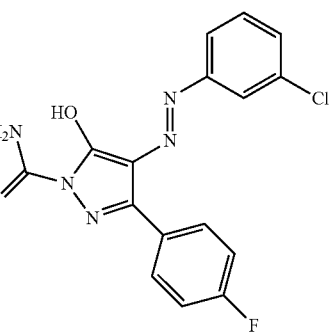
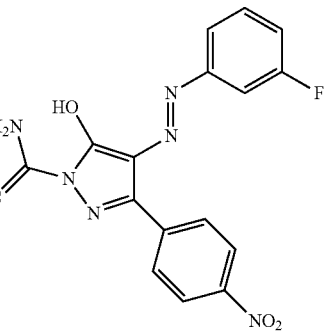

109
-continued
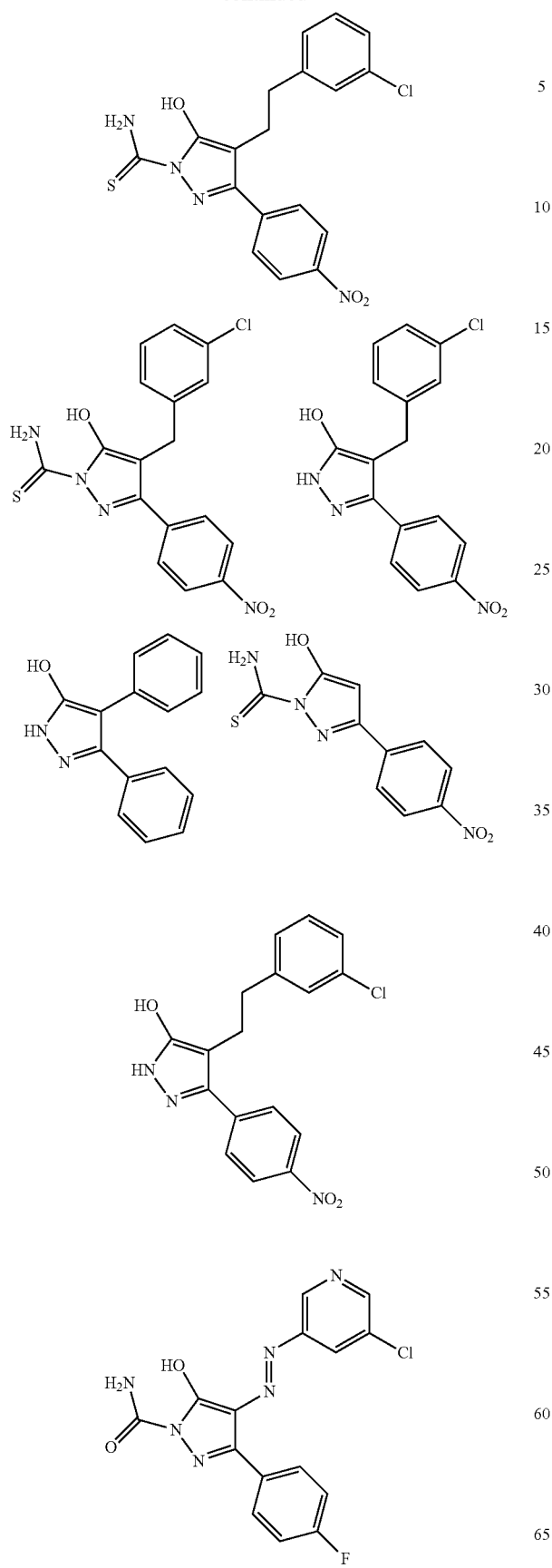
110
-continued
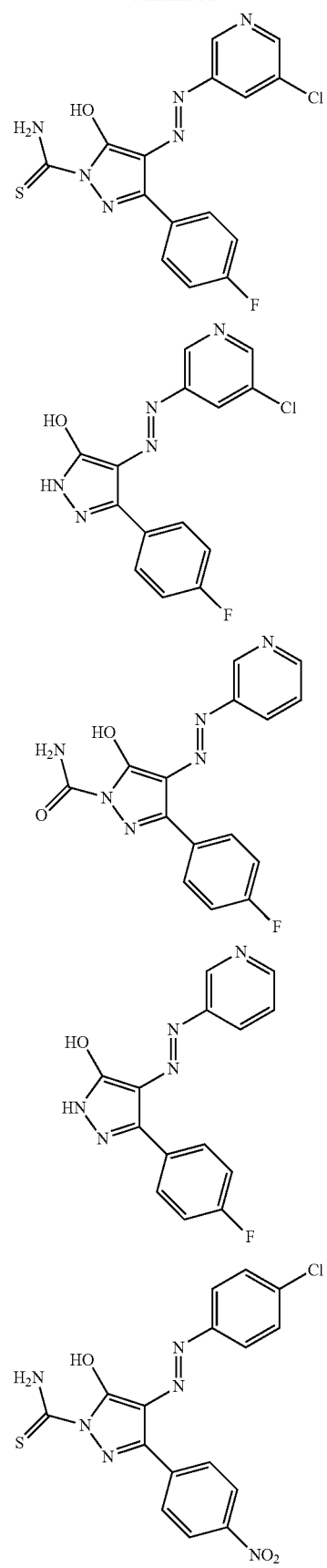

111
-continued
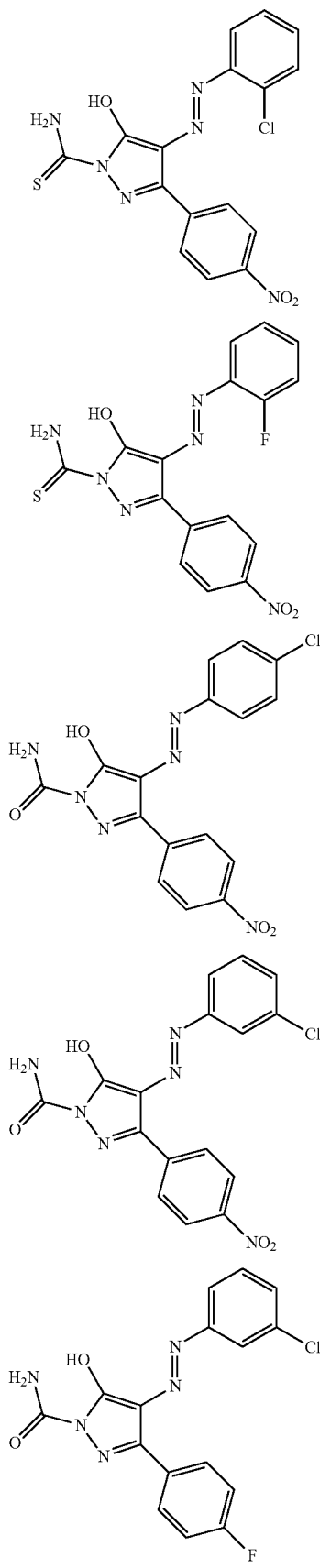
112
-continued
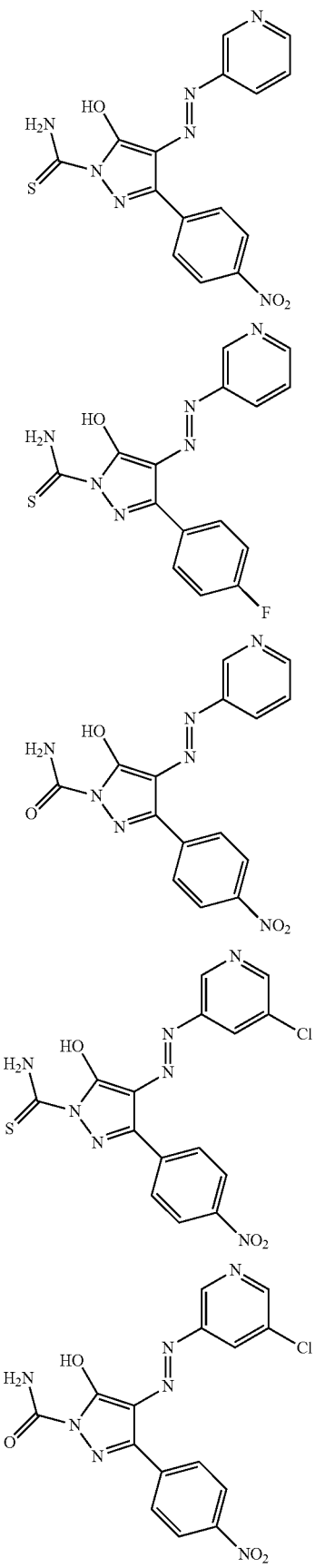

113
-continued
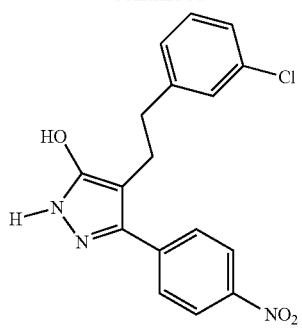
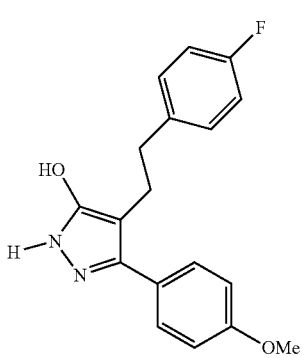
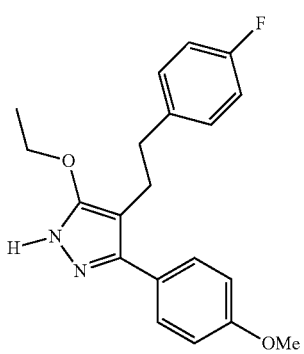
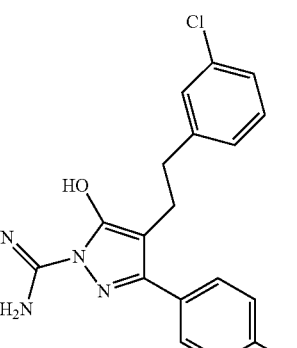
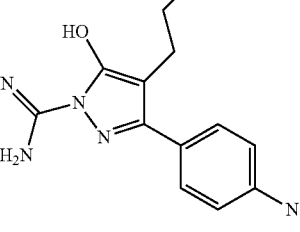
114
-continued
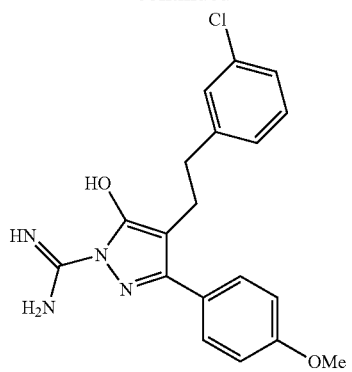
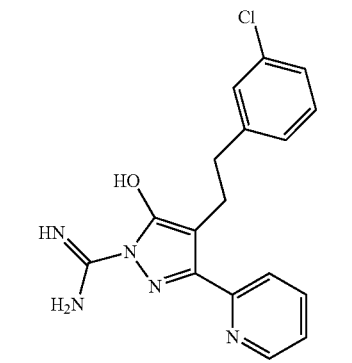
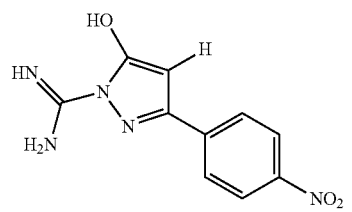
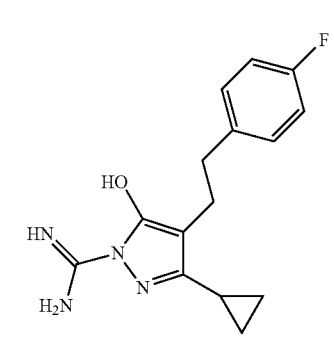
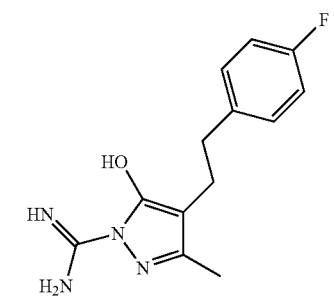

115
-continued
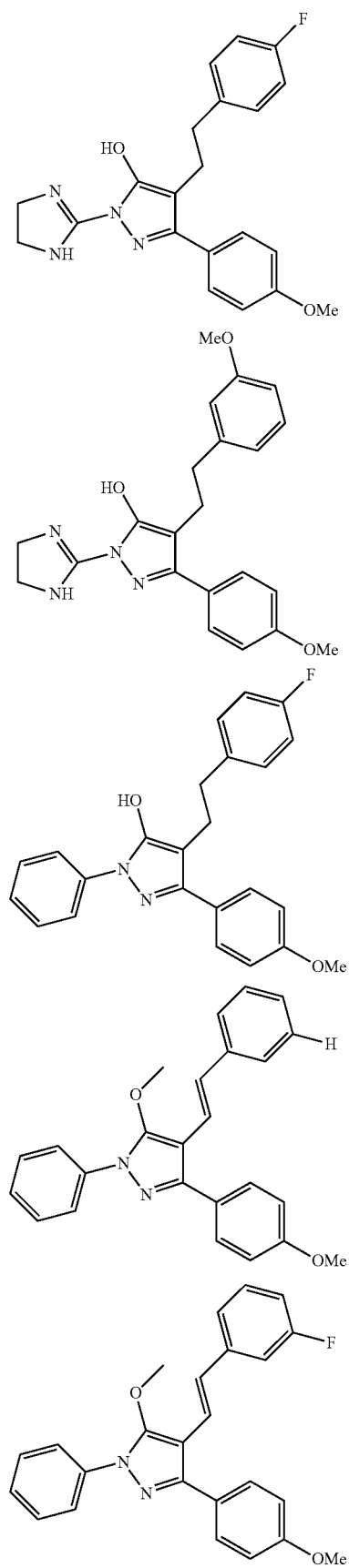
116
-continued
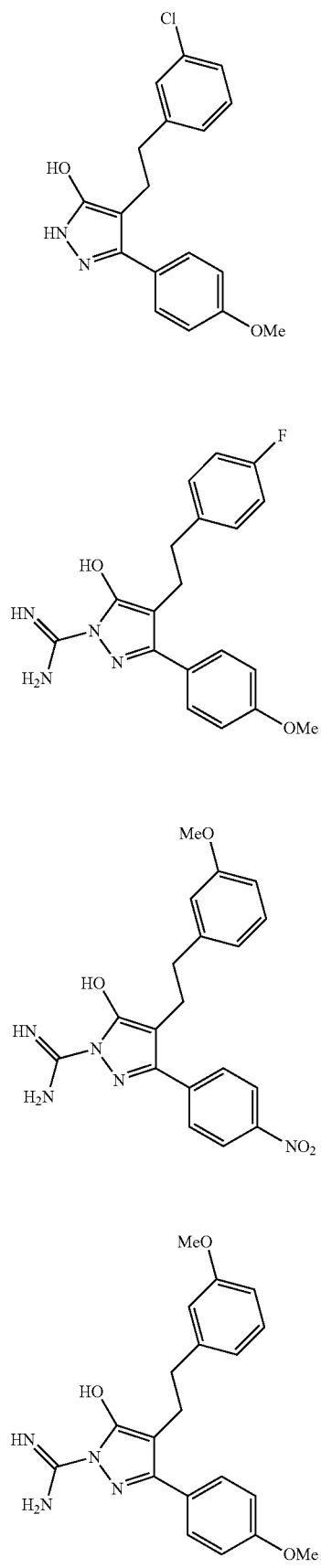

-continued

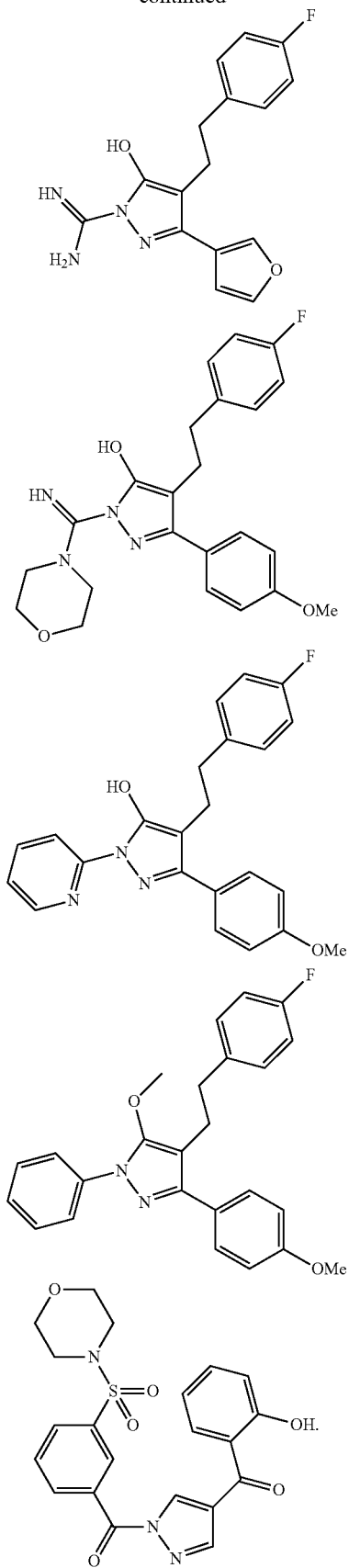

14. The method of claim 11 wherein the biological function of Nef is selected from HIV infectivity, HIV replication, or AIDS progression.

15. A method of inhibiting an activity of a Nef-dependent kinase comprising contacting the Nef-dependent kinase with an effective amount of a compound according to claim 11.

16. A method of treating a Nef-mediated disease, comprising administering to a subject an effective amount of a compound according to claim 11.

17. A method of treating HIV, comprising administering to a subject an effective amount of a compound according to claim 11.

18. The method according to claim 17 wherein the HIV-related condition is selected from HIV replication, HIV-associated CD4+ T-cell loss and immunodeficiency, HIV-induced infection, Kaposi's sarcoma, HIV-associated nephropathy, AIDS dementia complex, and combinations thereof.

19. The method of claim 17 wherein the subject is suffering from the HIV-related condition or the subject is administered the compound prophylactically or post-exposure prophylactically.

20. The method of claim 11 wherein the effective amount ranges from greater than zero to about 1000 mg/kg/day.

21. The method of claim 11 wherein the compound is administered as a formulation comprising the compound and a pharmaceutically acceptable carrier.

22. The method of claim 21 wherein the formulation further comprises at least one antiretroviral drug selected from an entry inhibitor, a CCR5 receptor antagonist, a nucleoside reverse transcriptase inhibitor, a non-nucleoside reverse transcriptase inhibitor, a protease inhibitor, an integrase inhibitor, a maturation inhibitor, or combinations thereof.

23. The method of claim 11 wherein the method is performed in vitro or in vivo.

24. A method for identifying antimicrobial agents, comprising:
coupling Nef with a kinase to form a complex; and
exposing the complex to one or more compounds having a Formula 2

Formula 2 wherein $R^1$ is selected from hydrogen, aliphatic, aryl, heteroaliphatic, oxo, heteroaryl, or combinations thereof; $R^2$ is selected from hydrogen, aliphatic, heteroaliphatic, hydroxyl, alkoxy, thiol, thioether, amine, or combinations thereof; $R^3$ is selected from hydrogen, aliphatic, heteroaliphatic, aryl, heteroaryl, or combinations thereof; $R^4$ is selected from hydrogen, aliphatic, heteroaliphatic, aryl, heteroaryl, and combinations thereof; $R^3$ and $R^4$ can be joined together to form a 5-, 6-, 7-, or 8-membered saturated or unsaturated ring, optionally comprising one or more heteroatoms and optionally substituted with one or more substituents selected from aliphatic, heteroaliphatic, halogen, aryl, or heteroaryl; X is selected from nitrogen, oxygen, or carbon, $CH_2$, or $CHR^1$; Y is selected from nitrogen or CH.

25. The method of claim 24 wherein the kinase is a Src-family kinase.

26. The method of claim 24 wherein the kinase is Hck.

27. A pharmaceutical formulation, comprising a compound having a Formula 2, or a pharmaceutically acceptable salt or ester thereof,

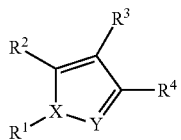

Formula 2 wherein $R^1$ is selected from hydrogen, aliphatic, aryl, heteroaliphatic, oxo, heteroaryl, or combinations thereof; $R^2$ is selected from hydroxyl, alkoxy, thiol, thioether, amine, or combinations thereof; $R^3$ is selected from —$(CH_2)_nR^6$ wherein n is zero to ten and $R^6$ is selected from aliphatic, heteroaliphatic, aryl, heteroaryl, or combinations thereof, —N=$NR^6R^7$ wherein each $R^6$ and $R^7$ independently are selected from hydrogen, aliphatic, heteroaliphatic, aryl, heteroaryl, or combinations thereof, and —C=$CR^6R^7$ wherein each $R^6$ and $R^7$ independently are selected from hydrogen, aliphatic, heteroaliphatic, aryl, heteroaryl, or combinations thereof; $R^4$ is selected from alkyl having from 5 to 10 carbon atoms, cycloalkyl, alkenyl, cycloalkenyl, alkynyl, cycloalkynyl, heteroaliphatic, aryl, heteroaryl, and combinations thereof; X is selected from nitrogen, oxygen, or carbon, $CH_2$, or $CHR^1$; Y is selected from nitrogen or CH;

and at least one pharmaceutically acceptable carrier, excipient, or combination thereof.

28. The pharmaceutical formulation of claim 27 wherein the compound is selected from

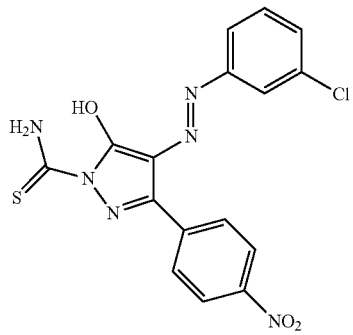

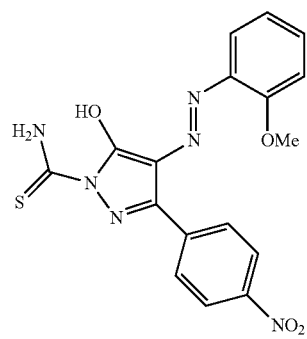

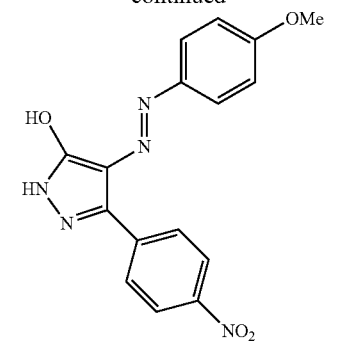

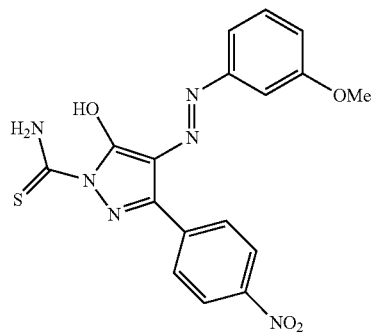

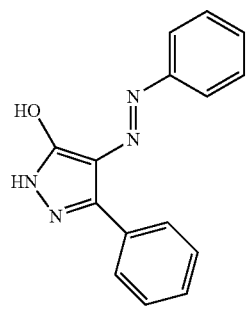

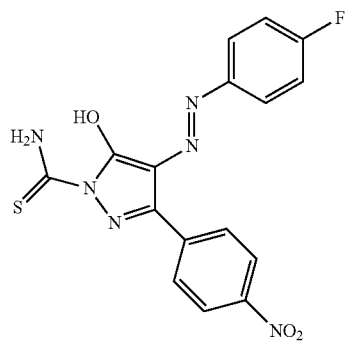

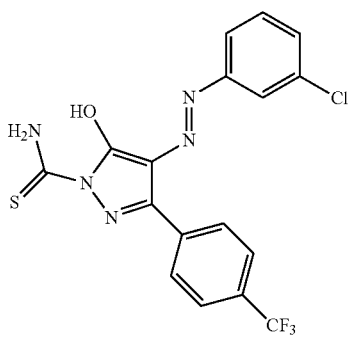

121
-continued
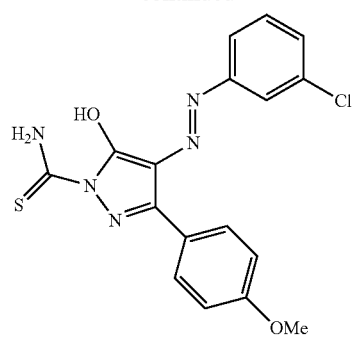
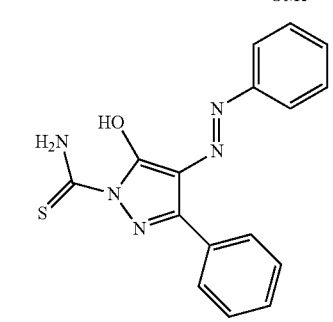
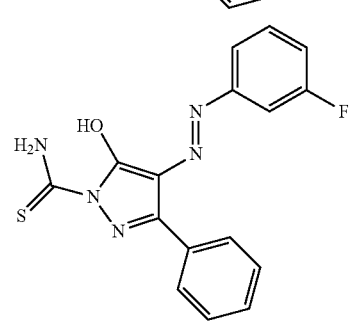
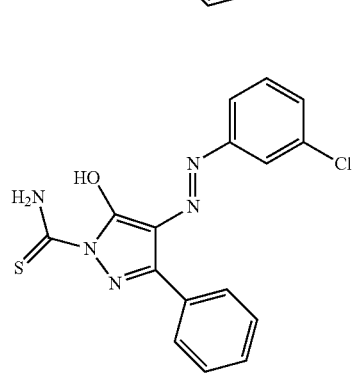
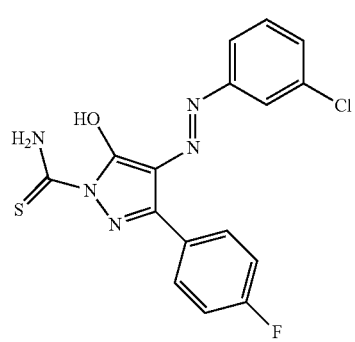
122
-continued
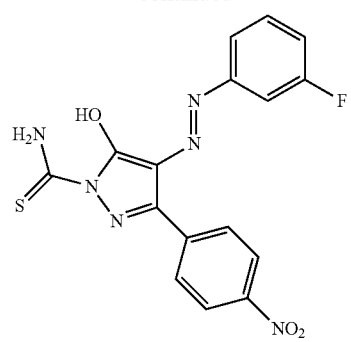
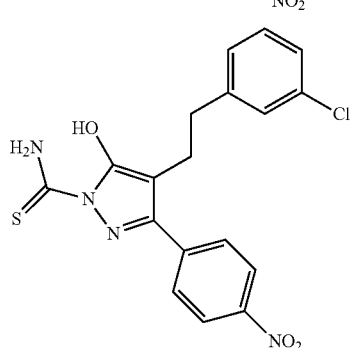
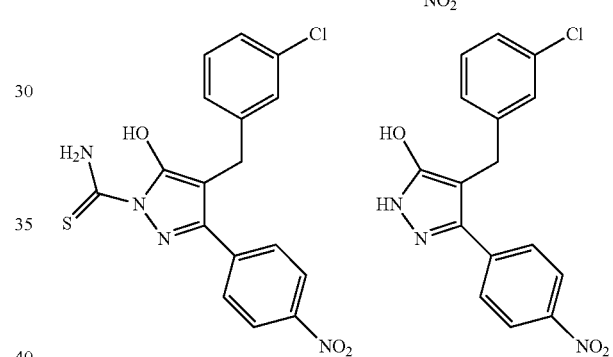
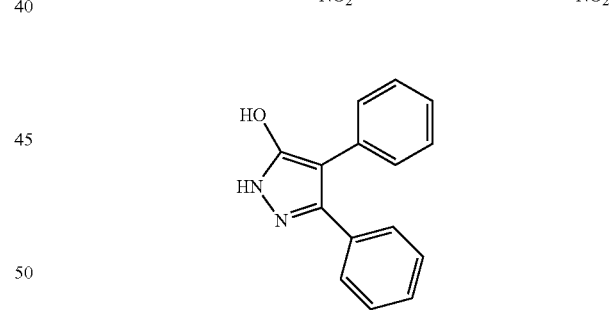
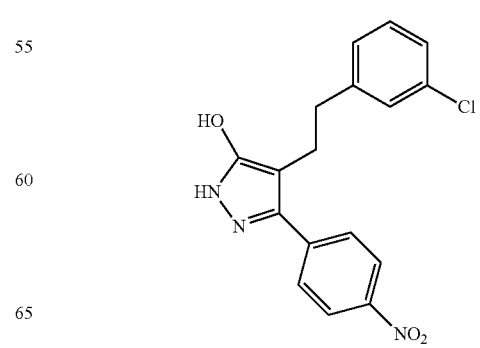

123
-continued
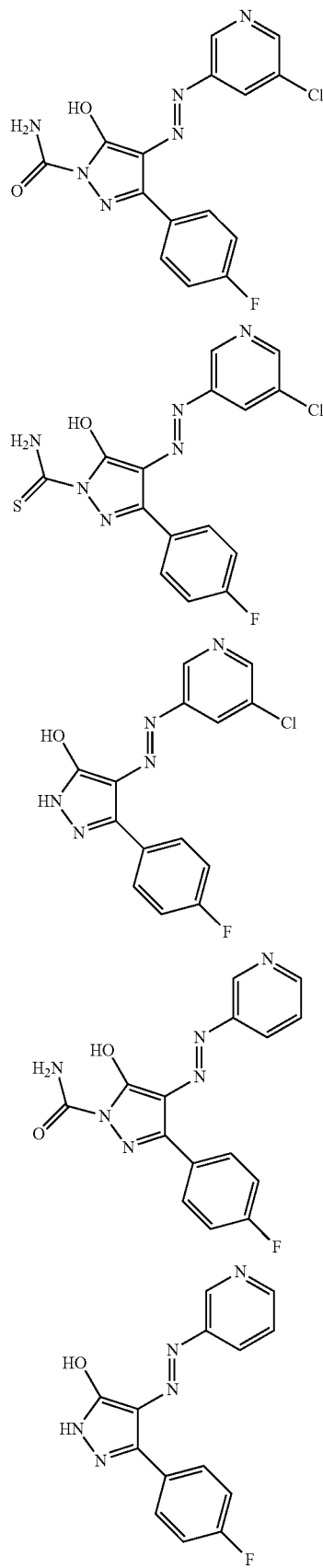
124
-continued
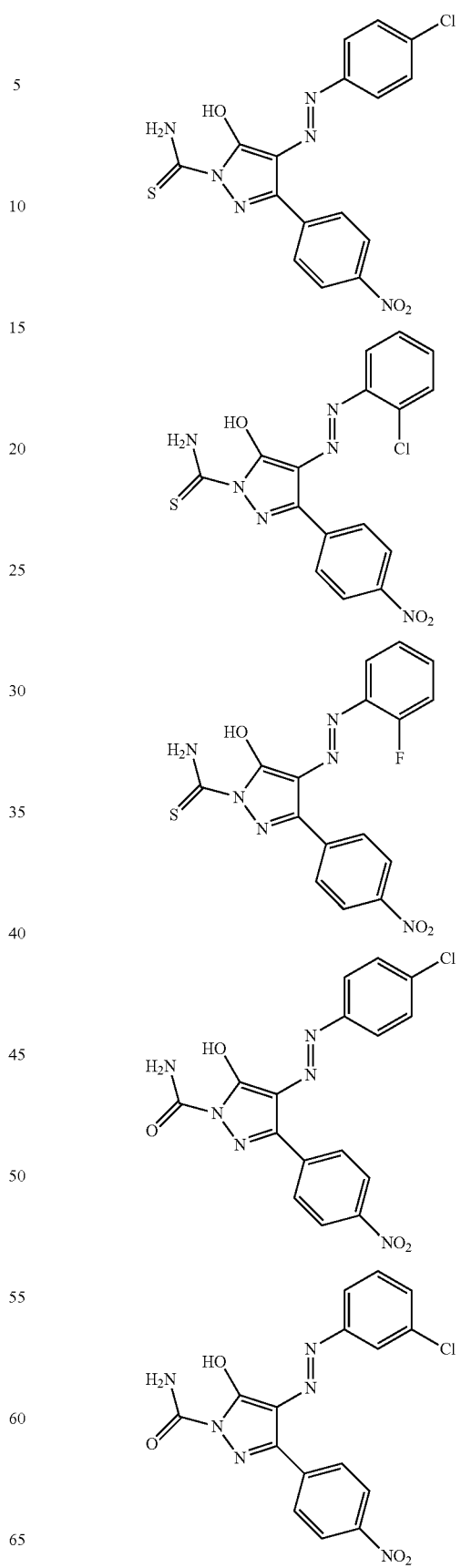

125
-continued
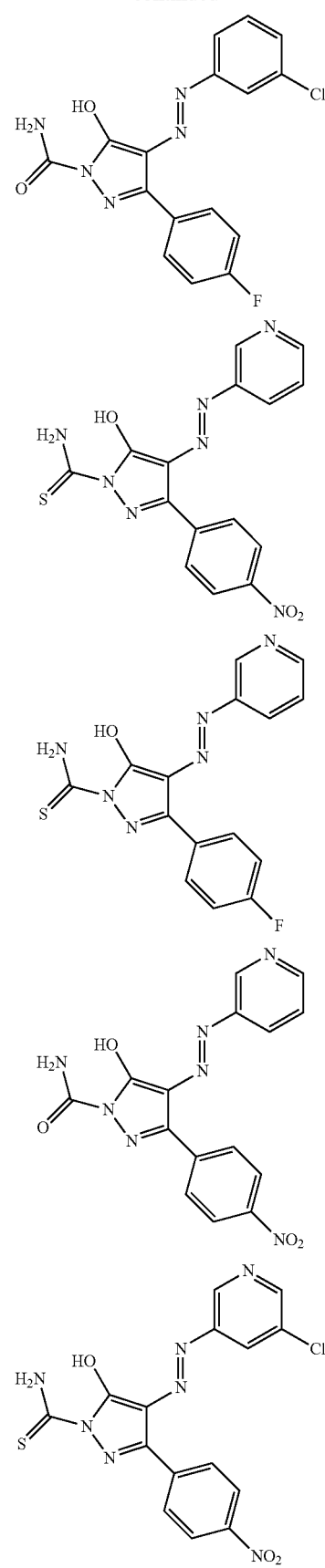
126
-continued
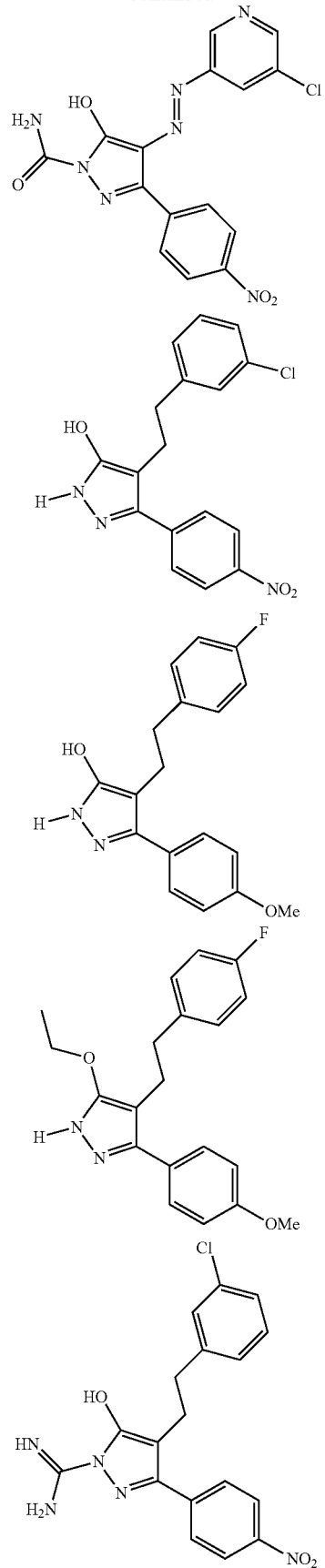

127
-continued
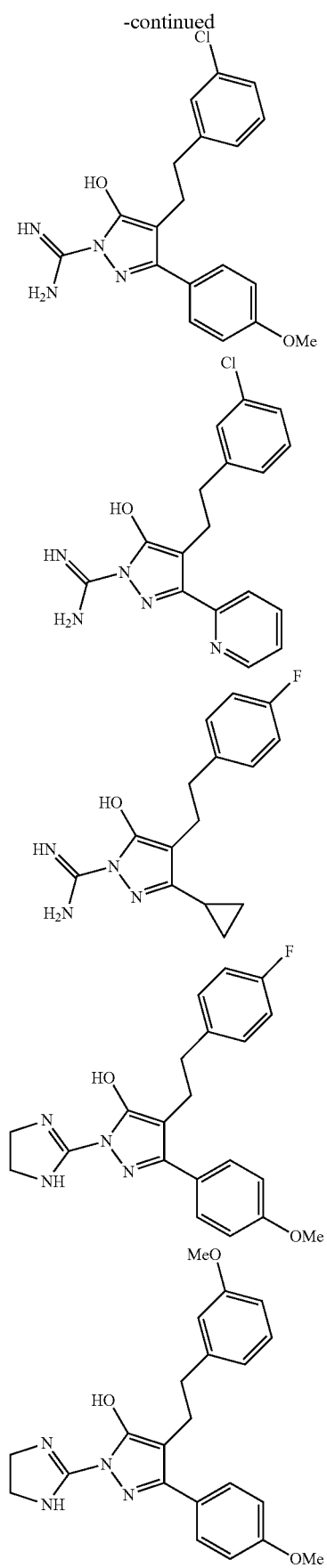
128
-continued
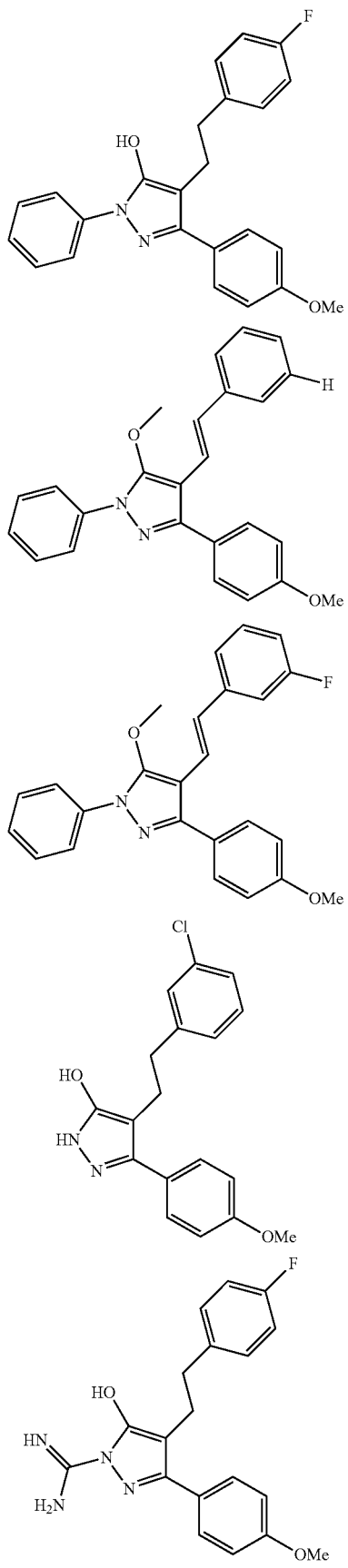

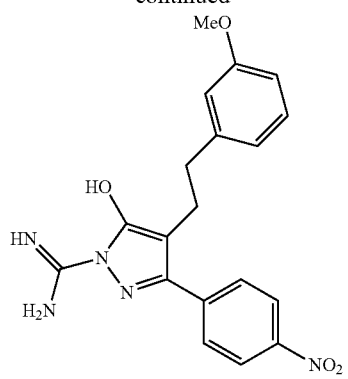

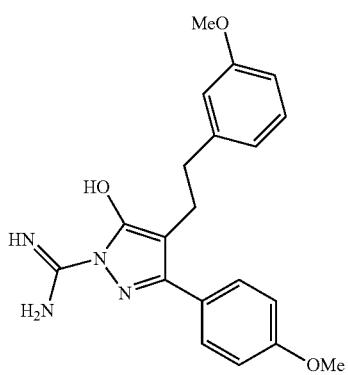

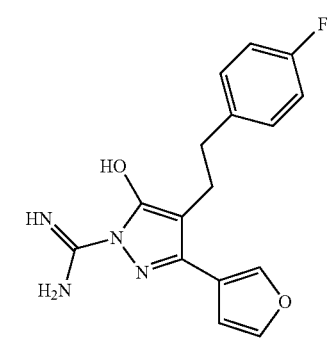

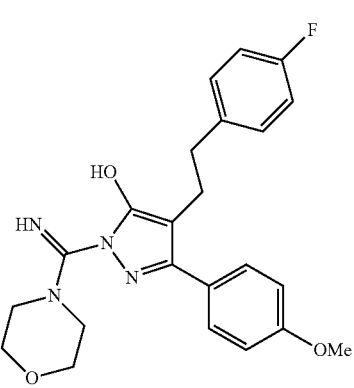

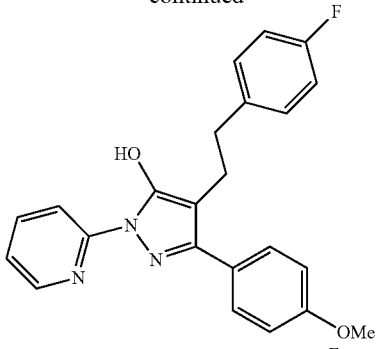

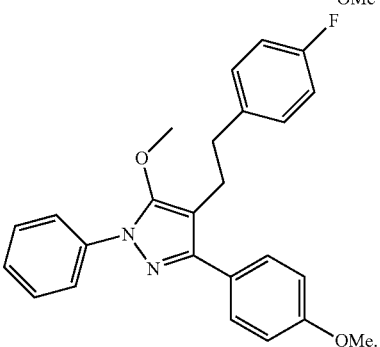

29. The pharmaceutical formulation of claim 27 further comprising a pharmacologically active agent other than the compound.

30. The pharmaceutical formulation of claim 29 wherein the pharmacologically active agent is an antiretroviral drug selected from entry inhibitor, a CCR5 receptor antagonist, a nucleoside reverse transcriptase inhibitor, a non-nucleoside reverse transcriptase inhibitor, a protease inhibitor, an integrase inhibitor, a maturation inhibitor, or combinations thereof.

31. The pharmaceutical formulation of claim 27 wherein the compound is not (E)-4-((3-chlorophenyl)diazenyl)-5-hydroxy-3-(4-nitrophenyl)-1H-pyrazole-1-carbothioamide.

32. A vaccine adjuvant having a Formula 2, or an ester or pharmaceutically acceptable salt thereof, Formula 2

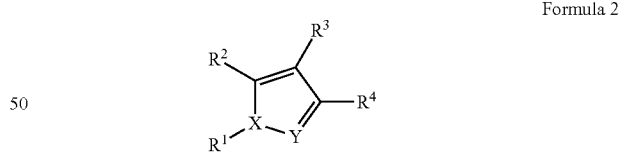

wherein $R^1$ is selected from hydrogen, aliphatic, aryl, heteroaliphatic, oxo, heteroaryl, or combinations thereof; $R^2$ is selected from hydrogen, aliphatic, heteroaliphatic, hydroxyl, alkoxy, thiol, thioether, amine, or combinations thereof; $R^3$ is selected from —$(CH_2)_n R^6$ wherein n is zero to ten and $R^6$ is selected from aliphatic, heteroaliphatic, aryl, heteroaryl, or combinations thereof, —N=$NR^6R^7$ wherein each $R^6$ and $R^7$ independently are selected from hydrogen, aliphatic, heteroaliphatic, aryl, heteroaryl, or combinations thereof, and —C=$CR^6R^7$ wherein each $R^6$ and $R^7$ independently are selected from hydrogen, aliphatic, heteroaliphatic, aryl, heteroaryl, or combinations thereof; $R^4$ is selected from alkyl having from 5 to 10 carbon atoms, cycloalkyl, alkenyl, cycloalkenyl, alkynyl, cycloalkynyl, heteroaliphatic, aryl, heteroaryl, and combinations thereof; X is selected from nitrogen, oxygen, or carbon, CH$_2$, or CHR$^1$; Y is selected from nitrogen or CH.
33. The vaccine adjuvant of claim 32 wherein the compound is not (E)-4-((3-chlorophenyl)diazenyl)-5-hydroxy-3-(4-nitrophenyl)-1H-pyrazole-1-carbothioamide.
34. The vaccine adjuvant of claim 32 selected from
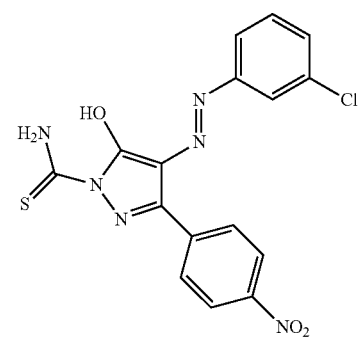
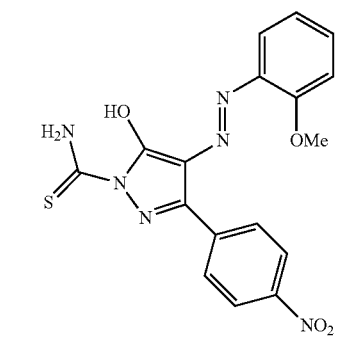
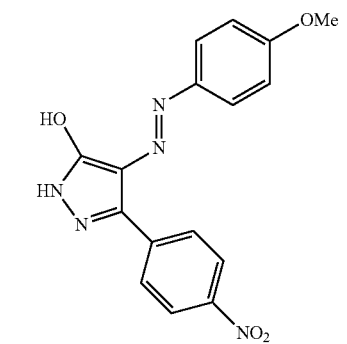
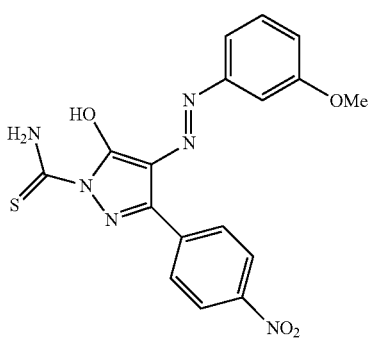
-continued
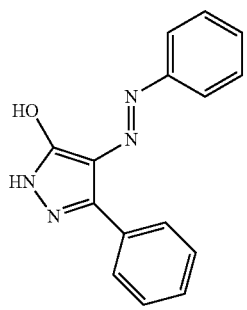
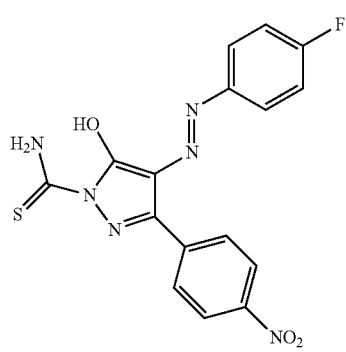
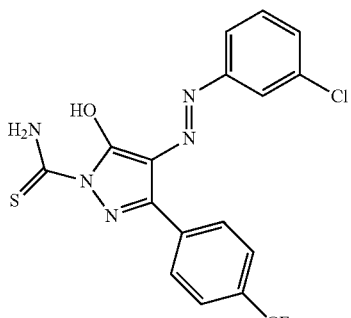
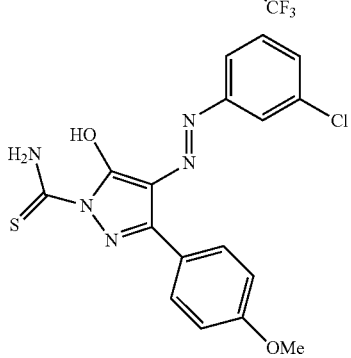
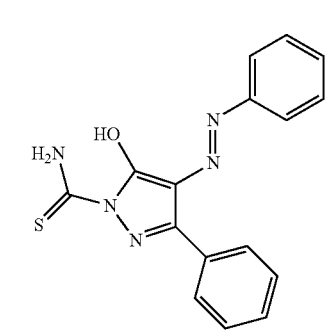

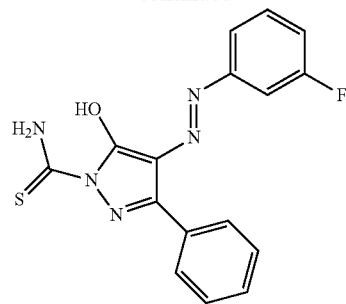
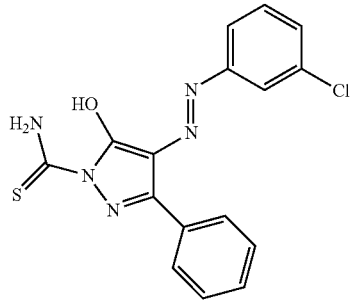
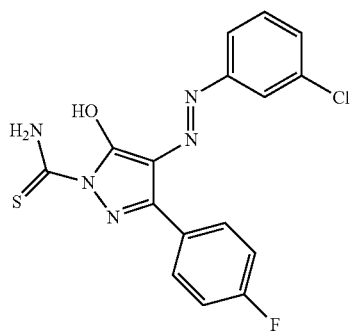
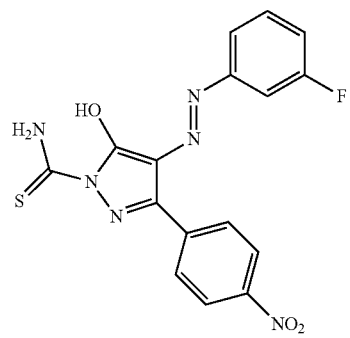
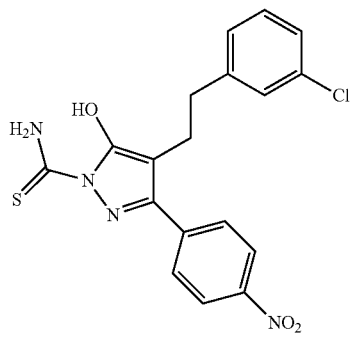
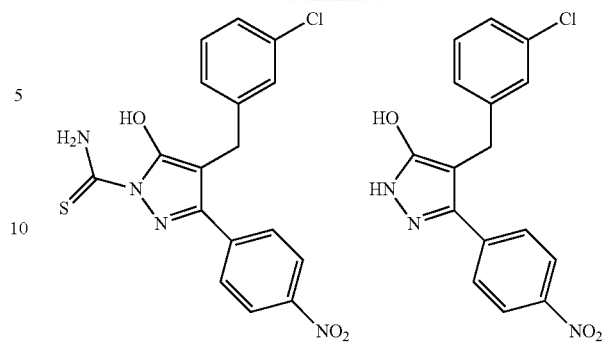
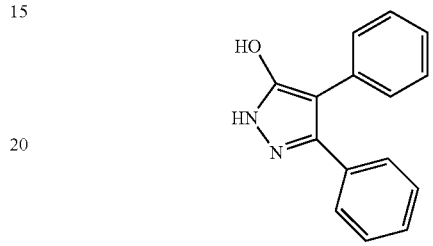
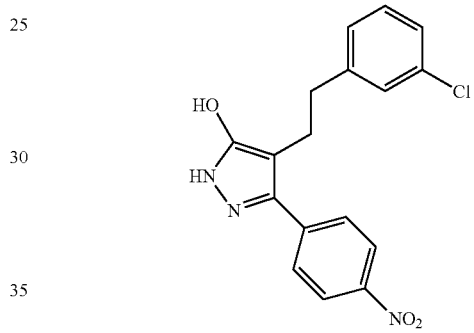
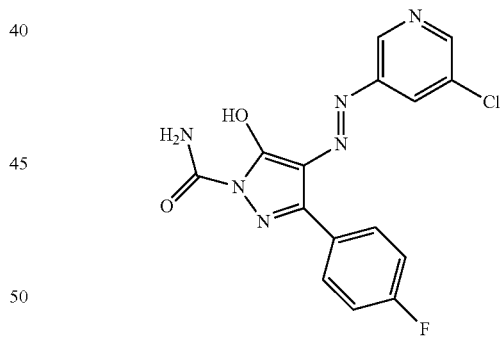
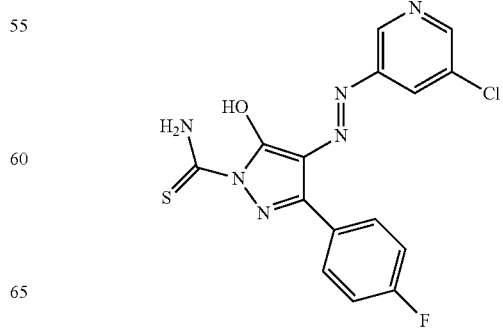

135
-continued
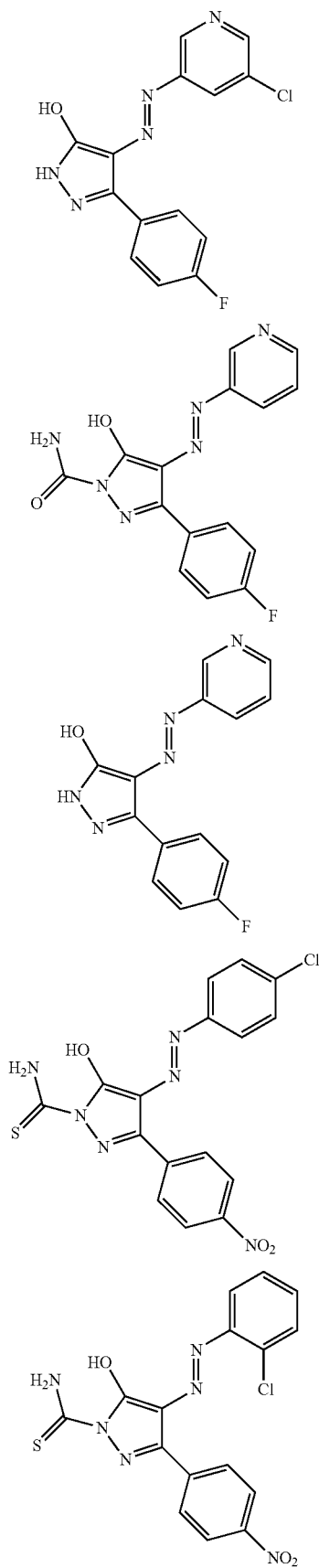
136
-continued
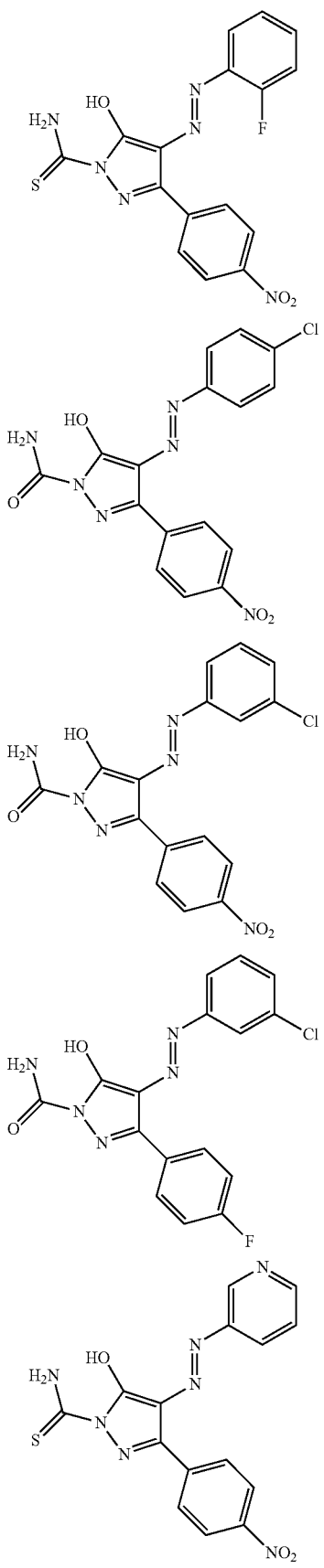

137
-continued
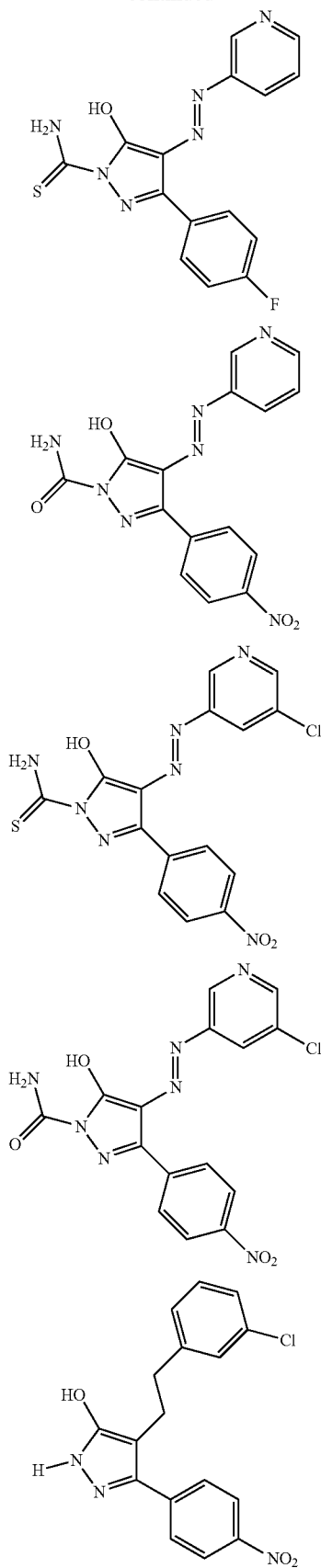
138
-continued
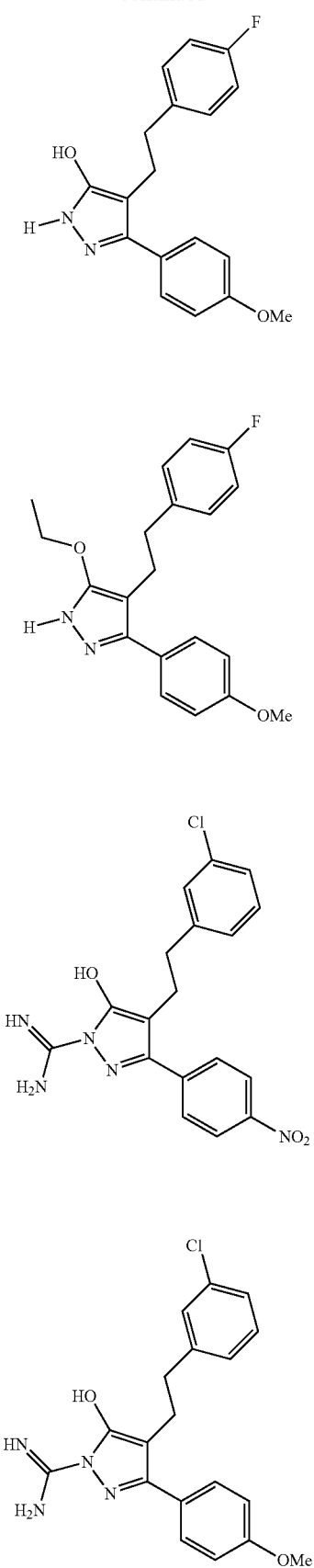

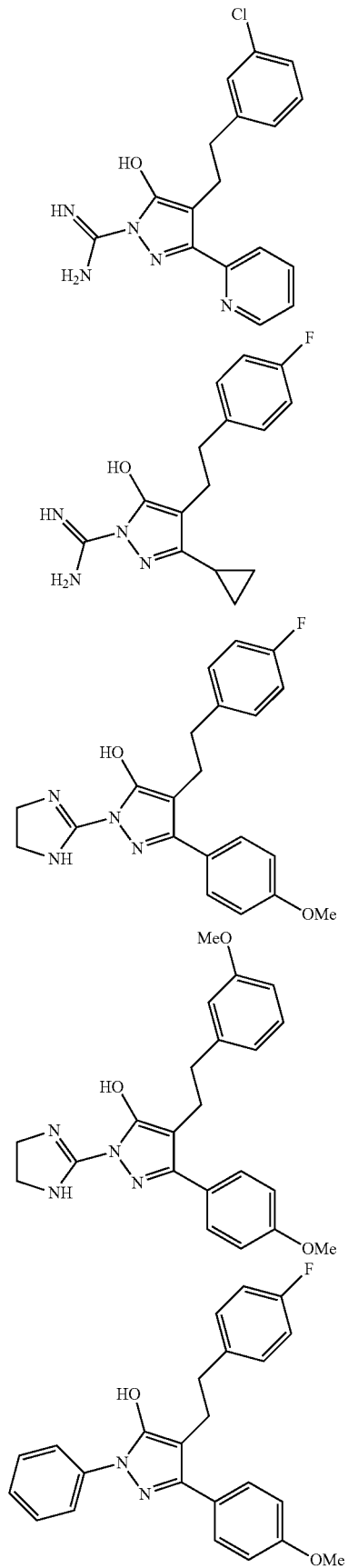
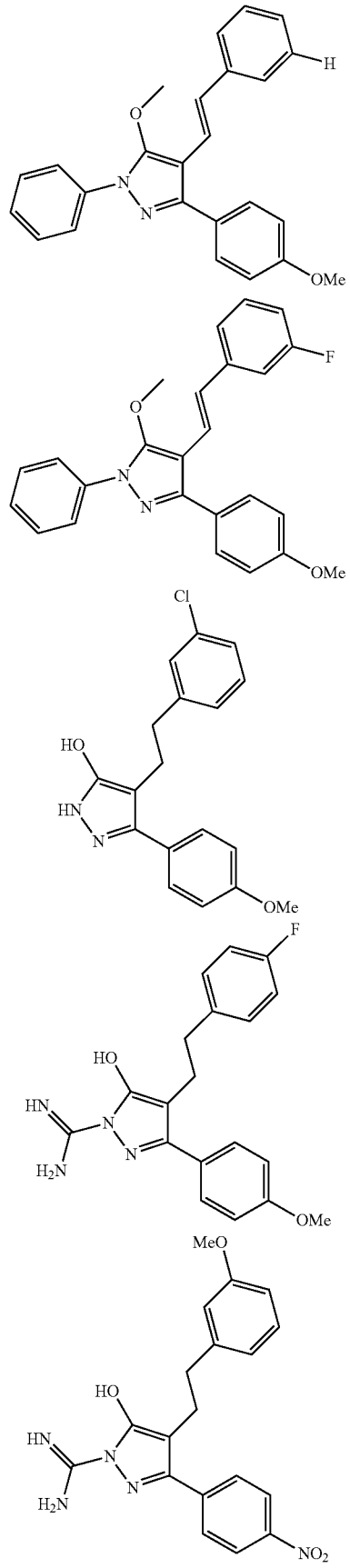

-continued

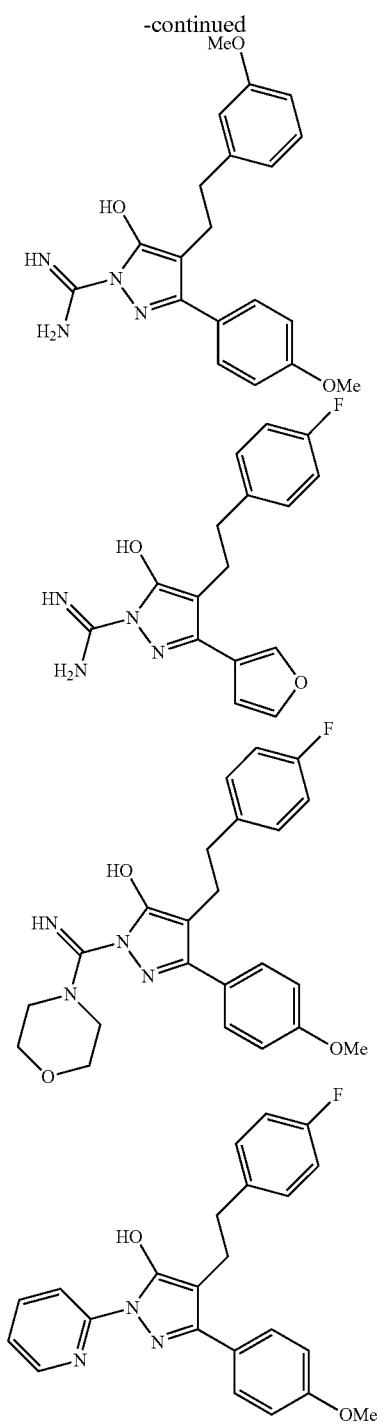

-continued

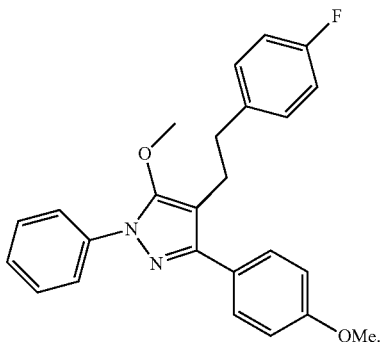

35. A pharmaceutical formulation, comprising a compound having a Formula 2, or a pharmaceutically acceptable salt or ester thereof,

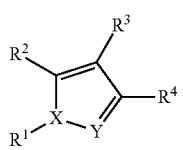

Formula 2 wherein $R^1$ is selected from hydrogen, aliphatic, aryl, heteroaliphatic, oxo, heteroaryl, or combinations thereof; $R^2$ is selected from hydrogen, aliphatic, heteroaliphatic, hydroxyl, alkoxy, thiol, thioether, amine, or combinations thereof; $R^3$ is selected from hydrogen, aliphatic, heteroaliphatic, aryl, heteroaryl, or combinations thereof; $R^4$ is selected from hydrogen, aliphatic, heteroaliphatic, aryl, heteroaryl, and combinations thereof; $R^3$ and $R^4$ can be joined together to form a 5-, 6-, 7-, or 8-membered saturated or unsaturated ring, optionally comprising one or more heteroatoms and optionally substituted with one or more substituents selected from aliphatic, heteroaliphatic, halogen, aryl, or heteroaryl; X is selected from nitrogen, oxygen, or carbon, $CH_2$, or $CHR^1$; Y is selected from nitrogen or CH;

at least one pharmaceutically acceptable carrier, excipient, or combination thereof; and an antiretroviral drug selected from entry inhibitor, a CCR5 receptor antagonist, a nucleoside reverse transcriptase inhibitor, a non-nucleoside reverse transcriptase inhibitor, a protease inhibitor, an integrase inhibitor, a maturation inhibitor, or combinations thereof.

* * * * *